(12) United States Patent
Jiao et al.

(10) Patent No.: US 11,696,949 B2
(45) Date of Patent: Jul. 11, 2023

(54) CORONAVIRUS-TARGETING UNIVERSAL DC CELL VACCINE, AND PREPARATION METHOD AND USE THEREOF

(71) Applicants: Beijing DCTY Biotech Co., Ltd., Beijing (CN); Shunchang Jiao, Beijing (CN)

(72) Inventors: Shunchang Jiao, Beijing (CN); Rong Zhang, Beijing (CN); Zishan Zhou, Beijing (CN)

(73) Assignees: Beijing DCTY Biotech Co., Ltd., Beijing (CN); Shunchang Jiao, Beijing (CN)

( * ) Notice: Subject to any disclaimer, the term of this patent is extended or adjusted under 35 U.S.C. 154(b) by 0 days.

(21) Appl. No.: 16/989,517

(22) Filed: Aug. 10, 2020

(65) Prior Publication Data

US 2021/0275663 A1 Sep. 9, 2021
US 2022/0096623 A9 Mar. 31, 2022

(30) Foreign Application Priority Data

Mar. 9, 2020 (CN) .......................... 202010156348.5

(51) Int. Cl.
*C12P 21/06* (2006.01)
*A61K 39/215* (2006.01)
(Continued)

(52) U.S. Cl.
CPC ............ *A61K 39/215* (2013.01); *A61P 31/14* (2018.01); *C07K 14/165* (2013.01); *C12N 15/86* (2013.01)

(58) Field of Classification Search
None
See application file for complete search history.

(56) References Cited

U.S. PATENT DOCUMENTS 10,030,252 B2 * 7/2018 Florkiewicz ........... A61K 39/00
2006/0286124 A1 * 12/2006 Burt ..................... A61K 39/215
435/456
(Continued)

FOREIGN PATENT DOCUMENTS

CN 1990042 A 7/2007
CN 110195042 B 9/2019
(Continued)

OTHER PUBLICATIONS

EPO translation of the specification of CN111088270-A (Year: 2020).*

(Continued)

*Primary Examiner* — M Franco G Salvoza
(74) *Attorney, Agent, or Firm* — Nelson Mullins Riley & Scarborough LLP; Anthony A Laurentano

(57) ABSTRACT

The present invention provides a method for preparing a coronavirus-targeting universal DC cell vaccine, and belongs to the technical field of virus vaccine preparation. The preparation method includes the following steps: ligating a fusion gene including a HLA gene and a coronavirus antigen gene onto an expression vector to obtain a recombinant vector; then transferring the recombinant vector into antigen-presenting cells to be transfected to obtain the coronavirus-targeting universal DC cell vaccine. The universal DC cell vaccine of the present invention has a targeting property against a coronavirus, can effectively stimulate a CTL, and has a killing effect on a target cell.

5 Claims, 44 Drawing Sheets

Specification includes a Sequence Listing.

(51) Int. Cl.
*A61P 31/14* (2006.01)
*C07K 14/165* (2006.01)
*C12N 15/86* (2006.01)

(56) References Cited

U.S. PATENT DOCUMENTS

2010/0291082 A1* 11/2010 Zurawski ................ A61P 37/04
  435/69.6
2021/0147799 A1* 5/2021 Zhang .................... A61K 35/17

FOREIGN PATENT DOCUMENTS

CN 110205298 B 9/2019
CN 111088270 A * 5/2020

OTHER PUBLICATIONS

Pless-Petig et al., "Aggravation of cold-induced injury in Vero-B4 cells by RPMI 1640 medium—Identification of the responsible medium components," BMC Biotechnol. 12:72 (Year: 2012).*

* cited by examiner

CORONAVIRUS-TARGETING UNIVERSAL DC CELL VACCINE, AND PREPARATION METHOD AND USE THEREOF

CROSS-REFERENCE TO RELATED APPLICATIONS

This application claims priority to Chinese Patent Application No 202010156348.5, filed Mar. 9, 2020. The Contents of the aforementioned application is hereby incorporated by reference.

SEQUENCE LISTING

The instant application contains a Sequence Listing which has been submitted electronically in ASCII format and is hereby incorporated by reference in its entirety. Said ASCII copy, created on Aug. 10, 2020, is named BGIM_002_Sequence_Listing.txt and is 14,755 bytes in size.

TECHNICAL FIELD

The present invention relates to the technical field of virus vaccine preparation, and in particular to a coronavirus-targeting universal DC cell vaccine, and a preparation method and use thereof.

BACKGROUND

A coronavirus belongs to the genus of Coronavirus of Coronaviridae in the systematic classification. The human diseases caused by the coronavirus are mainly respiratory system infection. At present, there are specific preventions for coronavirus prevention, i.e., targeted prevention measures (vaccines, the development of vaccines is possible, but it takes a long time, and solving the problem of virus reproduction is its problem) and non-specific prevention measures (i.e., measures for preventing infectious diseases of the respiratory tract in spring, such as keeping warm, washing hands, ventilating, avoiding excessive fatigue and contact with patients, and going less to crowded public places, etc.). The types of coronavirus vaccines in the prior art include inactivated coronavirus vaccines, coronavirus spike protein vaccines and adenovirus vector vaccines. However, currently there is no report or statement about the coronavirus-targeting universal DC cell vaccine in the prior art.

SUMMARY

An objective of the present invention is to provide a coronavirus-targeting universal DC cell vaccine, and a preparation method and use thereof. The universal DC cell vaccine of the present invention has a targeting property against a coronavirus, can effectively stimulate a CTL, and has a killing effect on a target cell.

In order to realize the objective of the present invention, the present invention provides the following technical solutions.

The present invention provides a method for preparing a coronavirus-targeting universal DC cell vaccine, including the following steps:

1) ligating a fusion gene onto an expression vector to obtain a recombinant vector, wherein the fusion gene includes a first fusion gene or a second fusion gene, the first fusion gene includes an HLA gene and a gene of coronavirus open reading frame protein connected by a linker sequence, and the second fusion gene includes an HLA gene and a gene of coronavirus structural protein connected by a linker sequence;

2) transferring the recombinant vector of the step 1) into antigen-presenting cells to be transfected, and screening antigen-presenting cells into which the recombinant vector has been successfully transferred with antibiotics, so as to obtain the coronavirus-targeting universal DC cell vaccine;

wherein in the step 1), the gene of coronavirus open reading frame protein is selected from one of ORF3a, ORF6, ORF7a and ORF8; the nucleotide sequence of the ORF3a is as shown in SEQ ID NO.1; the nucleotide sequence of the ORF6 is as shown in SEQ ID NO.2; the nucleotide sequence of the ORF7a is as shown in SEQ ID NO.3; and the nucleotide sequence of the ORF8 is as shown in SEQ ID NO.4;

the gene of the coronavirus structural protein in the step 1) is selected from one of a coronavirus E protein gene, a coronavirus S protein gene, a coronavirus PLP protein gene, a coronavirus M protein gene and a coronavirus N protein gene; the nucleotide sequence of the coronavirus E protein gene is as shown in SEQ ID NO.5; the nucleotide sequence of the coronavirus S protein gene is as shown in SEQ ID NO.6; the nucleotide sequence of the coronavirus PLP protein gene is as shown in SEQ ID NO.7; the nucleotide sequence of the coronavirus M protein gene is as shown in SEQ ID NO.8; and the nucleotide sequence of the coronavirus N protein gene is as shown in SEQ ID NO.9.

Preferably, the HLA gene of the step 1) is selected from one of HLA-A0201, HLA-A0207, HLA-A3303, HLA-A3001, HLA-A0206, HLA-A0101, HLA-A2601, HLA-A0301, HLA-A0203, HLA-B4601, HLA-B4001, HLA-B1501, HLA-B5801, HLA-B1302, HLA-B5101, HLA-B1301, HLA-B0702, HLA-B4006, HLA-B3501, HLA-B5401, HLA-B5502, HLA-B4403, HLA-B1502, HLA-B4801, HLA-C0304, HLA-C0801, HLA-C0302, HLA-C0303, HLA-C0102, HLA-C0702, HLA-C1402, HLA-C0602, HLA-C1202, HLA-C1502 and HLA-C1203.

Preferably, the nucleotide sequence of the linker sequence in the step 1) is as shown in SEQ ID NO.10.

Preferably, a method for preparing the antigen-presenting cells to be transfected in the step 2) includes the following steps:

S1. ligating a fusion gene of TAX and ST40 connected by a linker sequence onto an expression vector to obtain a recombinant vector, wherein the nucleotide sequence of the TAX is as shown in SEQ ID NO. 11, and the nucleotide sequence of the ST40 is as shown in SEQ ID NO.12;

S2. packaging a lentivirus with the recombinant vector of the step S1 to obtain a packaged virus;

S3. infecting DC cells with the packaged virus of the step S2 to obtain infected DC cells;

S4. inoculating trophoblast cells in an upper culture chamber of a cell incubator, inoculating the infected DC cells obtained in the step S3 in a lower culture chamber of the cell incubator, conducting first culture for 4-6 weeks, conducting second culture for 1-2 weeks after removing CD3+ cells, then conducting third culture for more than 2 months after removing CD3+ cells, and taking antigen-presenting cell lines of limited amplification generations to obtain the antigen-presenting cells to be transfected.

Preferably, the nucleotide sequence of the fusion gene of the TAX and the ST40 connected by the linker sequence in the step S1 is as shown in SEQ ID NO.13.

Preferably, the trophoblast cells in the step S4 are prepared by the following method: culturing peripheral blood mononuclear cells in a 1640 medium containing fetal bovine serum for 9-14 h to obtain the trophoblast cells; and the percentage mass content of the fetal bovine serum in the 1640 medium is 8%-12%.

Preferably, the inoculation amount of the trophoblast cells in the step S4 is $0.5 \times 10^6$-$1.5 \times 10^6$ cells/well; and the inoculation amount of the infected DC cells is $0.5 \times 10^6$-$1.5 \times 10^6$ cells/well.

Beneficial effects of the present invention: the present invention provides a method for preparing a coronavirus-targeting universal DC cell vaccine, which includes the following steps: ligating a fusion gene including a HLA gene and a coronavirus antigen gene onto an expression vector to obtain a recombinant vector; then transferring the recombinant vector into antigen-presenting cells to be transfected to obtain the coronavirus-targeting universal DC cell vaccine. The universal DC cell vaccine of the present invention has a targeting property against a coronavirus, can effectively stimulate a CTL, and has a killing effect on a target cell. When the specific CTLs cultured with the universal DC cell vaccine of the present invention are used for killing target cells infected with the corresponding viruses of HLA type, the results show that: the DC vaccine of the present invention has a specific killing effect on cells infected with a virus having any of the HLA genes A0201, A0207, A3303, A3001, A2402, A1101, A0206, A0101, A2601, A0301, A0203, B1505, B1511, B4601, B4001, B1501, B5801, B1302, B5101, B1301, B0702, B4006, B3501, B5401, B5502, B4403, B1502, B4801, C0304, C0801, C0302, C0303, C0102, C0702, C1402, C0602, C1202, C1502, C1203, C0301.

DESCRIPTION OF THE EMBODIMENTS

Figure 1:
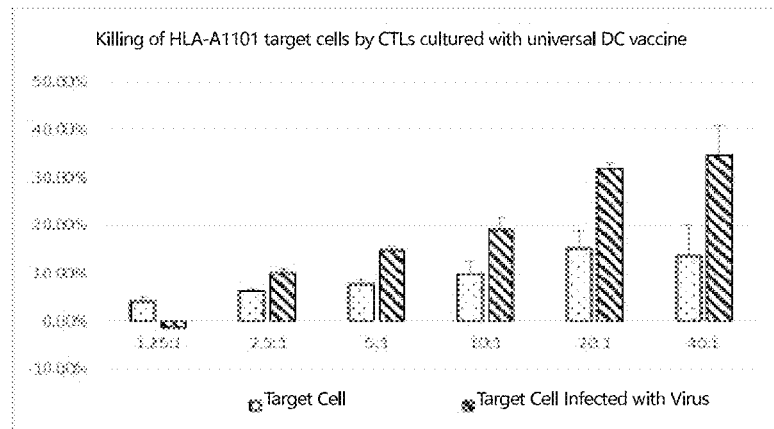
FIG. 1 shows the killing effect of CTLs cultured with the universal DC vaccine of Example 3 on HLA-A1101 target cells in Example 4.

The present invention provides a method for preparing a coronavirus-targeting universal DC cell vaccine, including the following steps:

1) ligating a fusion gene onto an expression vector to obtain a recombinant vector, wherein the fusion gene comprises a first fusion gene or a second fusion gene, the first fusion gene comprises an HLA gene and a gene of coronavirus open reading frame protein connected by a linker sequence, and the second fusion gene comprises an HLA gene and a gene of coronavirus structural protein connected by a linker sequence;

2) transferring the recombinant vector of the step 1) into antigen-presenting cells to be transfected, and screening antigen-presenting cells into which the recombinant vector has been successfully transferred with antibiotics, so as to obtain the coronavirus-targeting universal DC cell vaccine.

In the present invention, firstly the fusion gene is ligated onto the expression vector to obtain the recombinant vector, wherein the fusion gene includes a first fusion gene or a second fusion gene, the first fusion gene includes an HLA gene and a gene of coronavirus open reading frame protein connected by a linker sequence, and the second fusion gene includes an HLA gene and a gene of coronavirus structural protein connected by a linker sequence; and the gene of coronavirus open reading frame protein is selected from one of ORF3a, ORF6, ORF7a and ORFS; the nucleotide sequence of the ORF3a is as shown in SEQ ID NO.1, and is specifically: ATGGATTTGTTTATGAGAATCTT-CACAATTGGAACTGTAACTTTGAAGCAAGGT-GAAAT CAAGGATGCTACTCCTTCAGAT-TTTGTTCGCGCTACTGCAACGATACCGATACAAGC-CT CACTCCCTTTCGGATGGCTTAT-TGTTGGCGTTGCACTTCTTGCTGTTTTTCAGAGCG-CTT CCAAAAATCATAACCCT-CAAAAAGAGATGGCAACTAGCACTCTC-CAAGGGTGTTCACTT TGTTTGCAACTTGCTGTTGTTGTTTGTAACAGTT-TACTCACACCTTTTGCTCGTTGCTGC TGGCCTT-GAAGCCCCTTTTCTCTATCTTTATGCTTTAGTC-TACTTCTTGCAGAGTATAAAC TTTGTAAGAATAATAATGAGGCTTTGGCTTTGCTG-GAAATGCCGTTCCAAAAACCCATT ACTTTAT-GATGCCAACTATTTTCTTTGCTGGCATACTAATTGT-TACGACTATTGTATACCTT ACAATAGTGTAACTTCTTCAATTGTCAT-TACTTCAGGTGATGGCACAACAAGTCCTATTT CTGAACATGACTACCAGATTGGTGGTTATACT-GAAAAATGGGAATCTGGAGTAAAAGA CTGTGTTGTATTACACAGTTACTTCACTTCAGACT-ATTACCAGCTGTACTCAACTCAATT GAGTACA-GACACTGGTGTTGAACATGTTACCTTCTTCATCTA-CAATAAAATTGTTGATGA GCCTGAAGAACATGTCCAAATT-CACACAATCGACGGTTCATCCGGAGTTGT-TAATCCAG TAATGGAACCAATTTATGAT-GAACCGACGACGACTACTAGCGTGCCTTTG; the nucleotide sequence of the ORF6 is as shown in SEQ ID NO.2, and is specifically: ATGTTT-CATCTCGTTGACTTTCAGGTTACTATAGCAGAGAT-ATTACTAATTATTATGAGGA CTTTTAAAGTTTCCAT-TTGGAATCTTGATTACATCATAAACCTCATAATTAA-AAATTTATC TAAGTCACTAACTGAGAATAAATAT-TCTCAATTAGATGAAGAGCAACCAATGGAGATTG AT; the nucleotide sequence of the ORF7a is as shown in SEQ ID NO.3, and is specifically: ATGAAAATTAT-TCTTTTCTTGGCACTGATAACACTCGCTACTTGT-GAGCTTTATCACTAC CAAGAGTGTGTTAGAGGTA-CAACAGTACTTTTAAAAGAACCTTGCTCTTCTGGA-ACATA CGAGGGCAATTCACCATTT-CATCCTCTAGCTGATAACAAAT-TTGCACTGACTTGCTTTAG CACTCAAT-TTGCTTTTGCTTGTCCTGACGGCGTAAAACACGTC-TATCAGTTACGTGCCA GATCAGTTT-CACCTAAACTGTTCATCAGACAAGAGGAAGTT-CAAGAACTTTACTCTCCA ATTTTTCTTAT-TGTTGCGGCAATAGTGTTTATAACACTTTGCTTCAC-ACTCAAAAGAAAG ACAGAA; and the nucleotide sequence of the ORF8 is as shown in SEQ ID NO.4, and is specifically:

ATGAAATTTCTTGTTTTCTTAGGAATCATCACAACTGTAGCTGCATTTCA

CCAAGAATGTAGTTTACAGTCATGTACTCAACATCAACCATATGTAGTTG

ATGACCCGTGTCCTATTCACTTCTATTCTAAATGGTATATTAGAGTAGGA

GCTAGAAAATCAGCACCTTTAATTGAATTGTGCGTGGATGAGGCTGGTTC

TAAATCACCCATTCAGTACATCGATATCGGTAATTATACAGTTTCCTGTT

TACCTTTTACAATTAATTGCCAGGAACCTAAATTGGGTAGTCTTGTAGTG

CGTTGTTCGTTCTATGAAGACTTTTTAGAGTATCATGACGTTCGTGTTGT

TTTAGATTTCATC.

In the present invention, the coronavirus structural protein gene is selected from one of a coronavirus E protein gene, a coronavirus S protein gene, a coronavirus PLP protein gene, a coronavirus M protein gene and a coronavirus N protein gene; the nucleotide sequence of the coronavirus E protein gene is as shown in SEQ ID NO.5, and is specifically: ATGTACTCATTCGTTTCGGAAGA-GACAGGTACGTTAATAGT-TAATAGCGTACTTCTTTTT CTTGCTTTCGTGGTATTCTTGCTAGTTACACTAGC-CATCCTTACTGCGCTTCGATTGTGT GCGTACTGCTGCAATATTGTTAACGT-GAGTCTTGTAAAACCTTCTTTTTACGTTTACTCT CGTGTTAAAAATCTGAATTCTTCTAGAGTTCCT-GATCTTCTGGTC; the nucleotide sequence of the corona-virus S protein gene is as shown in SEQ ID NO.6, and is specifically: ATGGCAGATTCCAACGGTACTATTACCGTTGAAGAGCTTAAAAAGCTCCTTGAACAATG GAACCTAGTAATAGGTTTCCTATTCCTTACATGGATTTGTCTTCTACAATTTGCCTATGCCAACAGGAATAGGTTTTTGTATATAATTAAGTTAATTTTCCTCTGGCTGTTATGGCCAGTA ACTTTAGCTTGTTTTGTGCTTGCTGCTGTTTACAGAATAAATTGGATCACCGGTGGAATTGCTATCGCAATGGCTTGTCTTGTAGGCTTGATGTGGCTCAGCTACTTCATTGCTTCTTTCAGACTGTTTGCGCGTACGCGTTCCATGTGGTCATTCAATCCAGAAACTAACATTCTTCT CAACGTGCCACTCCATGGCACTATTCTGACCAGACCGCTTCTAGAAAGTGAACTCGTAATCGGAGCTGTGATCCTTCGTGGACATCTTCGTATTGCTGGACACCATCTAGGACGCTGT GACATCAAGGACCTGCCTAAAGAAATCACTGTTGCTACATCACGAACGCTTTCTTATTA CAAATTGGGAGCTTCGCAGCGTGTAGCAGGTGACTCAGGTTTTGCTGCATACAGTCGCT ACAGGATTGGCAACTATAAATTAAACACAGACCATTCCAGTAGCAGTGACAATATTGCT TTGCTTGTACAG; the nucleotide sequence of the coronavirus PLP protein gene is as shown in SEQ ID NO.7, and is specifically: ATGGAGGTGCGGACCATCAAGGTGTTCACCACAGTGGACAACATCAATCTGCACACAC AGGTGGTGGATATGTCCATGACCTACGGCCAGCAGTTTGGCCCTACATATCTGGACGGC GCCGATGTGACCAAGATCAAGCCACACAACTCTCACGAGGGCAAGACATTCTACGTGC TGCCCAATGACGATACCCTGAGGGTGGAGGCCTTCGAGTACTATCACCACAGACCCATCCTTTCTGGGCCGCTACATGTCTGCCCTGAACCACACAAAGAAGTGGAAGTATCCCC AAGTGAATGGCCTGACCTCTATCAAGTGGGCCGACAACAATTGCTACCTGGCCACAGC CCTGCTGACCCTGCAGCAGATCGAGCTGAAGTTCAACCCCCCTGCCCTGCAGGATGCA TACTATAGGGCAAGAGCAGGAGAGGCAGCAAACTTTTGCGCACTGATCCTGGCCTACTGTAATAAGACAGTGGGAGAGCTGGGCGACGTGCGGGAGACCATGAGCTATCTGTTCCA GCACGCCAACCTGGATTCCTGTAAGAGGGTGCTGAATGTGGTGTGCAAGACATGTGGC CAGCAGCAGACCACACTGAAGGGCGTGGAGGCCGTGATGTACATGGGCACCCTGAGC TATGAGCAGTTTAAGAAGGGCGTGCAGATCCCTTGCACATGTGGCA AGCAGGCCACCA AGTACCTGGTGCAGCAGGAGTCTCCATTCGTGATGATGAGCGCCCCACCCGCCCAGTAT GAGCTGAAGCACGGCACCTTCACCTGCGCCTCTGAGTACACCGGCAACTATCAGTGTG GCCACTACAAGCACATCACAAGCAAGGAGACCCTGTATTGCATCGACGGCGCCCTGCT GACAAAGAGCTCCGAGTACAAGGGCCCCATCACCGACGTGTTCTACAAGGAGAACAG CTATACCACAACCATCAAGCCTGTGACC; the nucleotide sequence of the coronavirus M protein gene is as shown in SEQ ID NO.8, and is specifically: ATGGCAGATTCCAACGGTACTATTACCGTTGAAGAGCTTAAAAAGCTCCTTGAACAATG GAACCTAGTAATAGGTTTCCTATTCCTTACATGGATTTGTCTTCTACAATTTGCCTATGCC AACAGGAATAGGTTTTTGTATATAATTAAGTTAATTTTCCTCTGGCTGTTATGGCCAGTA ACTTTAGCTTGTTTTGTGCTTGCTGCTGTTTACAGAATAAATTGGATCACCGGTGGAATTGCTATCGCAATGGCTTGTCTTGTAGGCTTGATGTGGCTCAGCTACTTCATTGCTTCTTTC AGACTGTTTGCGCGTACGCGTTCCATGTGGTCATTCAATCCAGAAACTAACATTCTTCT CAACGTGCCACTCCATGGCACTATTCTGACCAGACCGCTTCTAGAAAGTGAACTCGTAA TCGGAGCTGTGATCCTTCGTGGACATCTTCGTATTGCTGGACACCATCTAGGACGCTGT GACATCAAGGACCTGCCTAAAGAAATCACTGTTGCTACATCACGAACGCTTTCTTATTA CAAATTGGGAGCTTCGCAGCGTGTAGCAGGTGACTCAGGTTTTGCTGCATACAGTCGCT ACAGGATTGGCAACTATAAATTAAACACAGACCATTCCAGTAGCAGTGACAATATTGCT TTGCTTGTACAG; and the nucleotide sequence of the coronavirus N protein gene is as shown in SEQ ID NO.9, and is specifically:

ATGTCTGATAATGGACCCCAAAATCAGCGAAATGCACCCCGCATTACGTT

TGGTGGACCCTCAGATTCAACTGGCAGTAACCAGAATGGAGAACGCAGTG

GGGCGCGATCAAAACAACGTCGGCCCCAAGGTTTACCCAATAATACTGCG

TCTTGGTTCACCGCTCTCACTCAACATGGCAAGGAAGACCTTAAATTCCC

TCGAGGACAAGGCGTTCCAATTAACACCAATAGCAGTCCAGATGACCAAA

TTGGCTACTACCGAAGAGCTACCAGACGAATTCGTGGTGGTGACGGTAAA

ATGAAAGATCTCAGTCCAAGATGGTATTTCTACTACCTAGGAACTGGGCC

AGAAGCTGGACTTCCCTATGGTGCTAACAAAGACGGCATCATATGGGTTG

CAACTGAGGGAGCCTTGAATACACCAAAAGATCACATTGGCACCCGCAAT

CCTGCTAACAATGCTGCAATCGTGCTACAACTTCCTCAAGGAACAACATT

GCCAAAAGGCTTCTACGCAGAAGGGAGCAGAGGCGGCAGTCAAGCCTCTT

CTCGTTCCTCATCACGTAGTCGCAACAGTTCAAGAAATTCAACTCCAGGC

AGCAGTAGGGGAACTTCTCCTGCTAGAATGGCTGGCAATGGCGGTGATGC

TGCTCTTGCTTTGCTGCTGCTTGACAGATTGAACCAGCTTGAGAGCAAAA

TGTCTGGTAAAGGCCAACAACAACAAGGCCAAACTGTCACTAAGAAATCT

GCTGCTGAGGCTTCTAAGAAGCCTCGGCAAAAACGTACTGCCACTAAAGC

ATACAATGTAACACAAGCTTTCGGCAGACGTGGTCCAGAACAAACCCAAG

GAAATTTTGGGGACCAGGAACTAATCAGACAAGGAACTGATTACAAACAT

TGGCCGCAAATTGCACAATTTGCCCCCAGCGCTTCAGCGTTCTTCGGAAT

GTCGCGCATTGGCATGGAAGTCACACCTTCGGGAACGTGGTTGACCTACA

CAGGTGCCATCAAATTGGATGACAAAGATCCAAATTTCAAAGATCAAGTC

ATTTTGCTGAATAAGCATATTGACGCATACAAAACATTCCCACCAACAGA

GCCTAAAAAGGACAAAAAGAAGAAGGCTGATGAAACTCAAGCCTTACCGC

AGAGACAGAAGAAACAGCAAACTGTGACTCTTCTTCCTGCTGCAGATTTG

GATGATTTCTCCAAACAATTGCAACAATCCATGAGCAGTGCTGACTCAAC

TCAGGCC.

In the present invention, the HLA gene is selected from one of HLA-A0201, HLA-A0207 (HLA00012), HLA-A3303 (HLA00106), HLA-A3001 (HLA00089), HLA-A0206 (HLA00011), HLA-A0101 (HLA00001), HLA-A2601 (HLA00073), HLA-A0301 (HLA00037), HLA- A0203 (HLA00008), HLA-B4601 (HLA00331), HLA-B4001 (HLA00291), HLA-B1501 (HLA00162), HLA-B5801 (HLA00386), HLA-B1302 (HLA00153), HLA-B5101 (HLA00344), HLA-B1301 (HLA00152), HLA-B0702 (HLA00132), HLA-B4006 (HLA00297), HLA-B3501 (HLA00237), HLA-B5401 (HLA00367), HLA-B5502 (HLA00369), HLA-B4403 (HLA00319), HLA-B1502 (HLA00165), HLA-B4801 (HLA00335), HLA-C0304 (HLA00413), HLA-C0801 (HLA00445), HLA-C0302 (HLA00410), HLA-C0303 (HLA00411), HLA-C0102 (HLA00401), HLA-C0702 (HLA00434), HLA-C1402 (HLA00462), HLA-C0602 (HLA00430), HLA-C1202 (HLA00453), HLA-C1502 (HLA00467) and HLA-C1203 (HLA00455); the nucleotide sequence of the HLA-A0201 is as shown in SEQ ID NO.14, and is specifically: GCTAGCGCCACCATGGCCACCATGGCCGTCATGGCGCCCCGAACCCTCGTCCTGCTACTCTCGGGGGCTCTGGCCCTGACCCAGACCTGGGCGGGCTCTCACTCCATGAGGTATTTCTTCACATCCGTGTCCCGGCCCGGCCGCGGGGAGCCCCGCTTCATCGCAGTGGGCTACGTGGACGACACGCAGTTCGTGCGGTTCGACAGCGACGCCGCGAGCCAGAGGATGGAGCCGCGGGCGCCGTGGATAGAGCAGGAGGGTCCGGAGTATTGGGACGGGGAGACACGGAA AGTGAAGGCCCACTCACAGACTCACCGAGTGGACCTGGGGACCCTGCGCGGCTACTACAACCAGAGCGAGGCCGGTTCTCACACCGTCCAGAGGATGTATGGCTGCGACGTGGGGTCGGACTGGCGCTTCCTCCGCGGGTACCACCAGTACGCCTACGACGGCAAGGATTACATCGCCCTGAAAGAGGACCTGCGCTCTTGGACCGCGGCGGACATGGCAGCTCAGACC ACCAAGCACAAGTGGGAGGCGGCCCATGTGGCGGAGCAGTTGAGAGCCTACCTGGAG GGCACGTGCGTGGAGTGGCTCCGCAGATACCTGGAGAACGGGAAGGAGACGCTGCAGCGCACGGACGCCCCCAAAACGCATATGACTCACCACGCTGTCTCTGACCATGAAGCCA CCCTGAGGTGCTGGGCCCTGAGCTTCTACCCTGCGGAGATCACACTGACCTGGCAGCGGGATGGGGAGGACCAGACCCAGGACACGGAGCTCGTGGAGACCAGGCCTGCAGGGG ATGGAACCTTCCAGAAGTGGGCGGCTGTGGTGGTGCCTTCTGGACAGGAGCAGAGATA CACCTGCCATGTGCAGCATGAGGGTTTGCCCAAGCCCCTCACCCTGAGATGGGAGCCG TCTTCCCAGCCCACCATCCCCATCGTGGGCATCATTGCTGGCCTGGTTCT CTTTGGAGCT GTGATCACTGGAGCTGTGGTCGCTGCTGTGATGTGGAGGAGGAAGAGCTCAGATAGAA AAGGAGGGAGCTACTCTCAGGCTGCAAGCAGTGACAGTGCCCAGGGCTCTGATGTGT CTCTCACAGCTTGTAAAGTGGATTACAAGGATGACGACGATAAGGAGGGCAGAGGAAGTCTTCTAACATGCGGTGACGTGGAGGAGAATCCCGGCCCTGCCACCATGTCTCGCTCCGTGGCCTTAGCTGTGCTCGCGCTACTCTCTCTTTCTGGCCTGGAGGCTATCCAGCGTAC TCCAAAGATTCAGGTTTACTCACGTCATCCAGCAGAGAATGGAAAGTCAAATTTCCTG AATTGCTATGTGTCTGGGTTTCATCCATCCGACATTGAAGTTGACTTACTGAAGAATGGAGAGAGAATTGAAAAAGTGGAGCATTCAGACTTGTCTTTCAGCAAGGACTGGTCTTTCTATCTCTTGTACTACACTGAATTCACCCCCACTGAAAAAGATGAGTATGCCTGCCGTGT GAACCATGTGACTTTGTCACAGCCCAAGATAGTTAAGTGGGATCG AGACATGTAAGGATCC, and other sequences can be searched in data published at https://www.ebi.ac.uk/ipd/imgt/hla/dictionary.html.

In the present invention, the nucleotide sequence of the linker sequence is as shown in SEQ ID NO.10, and is specifically:

GCCACGAACTTCTCTCTGTTAAAGCAAGCAGGAGATGTTGAAGAAAACCC
CGGGCCT.

In the present invention, the expression vector preferably includes a plasmid (lentiviral vector) for preparing immortalized dendritic cells.

In the present invention, after the recombinant vector is obtained, the recombinant vector is transferred into the antigen-presenting cells to be transfected, and antigen-presenting cells into which the recombinant vector has been successfully transferred are screened with antibiotics, so as to obtain the coronavirus-targeting universal DC cell vaccine.

In the present invention, a method for preparing the antigen-presenting cells to be transfected preferably includes the following steps:

S1. ligating a fusion gene of TAX and ST40 connected by a linker sequence onto an expression vector to obtain a recombinant vector, wherein the nucleotide sequence of the TAX is as shown in SEQ ID NO. 11, and the nucleotide sequence of the ST40 is as shown in SEQ ID NO.12;

S2. packaging a lentivirus with the recombinant vector of the step S1 to obtain a packaged virus;

S3. infecting DC cells with the packaged virus of the step S2 to obtain infected DC cells;

S4. inoculating trophoblast cells in an upper culture chamber of a cell incubator, inoculating the infected DC cells obtained in the step S3 in a lower culture chamber of the cell incubator, conducting first culture for 4-6 weeks, conducting second culture for 1-2 weeks after removing CD3+ cells, then conducting third culture for more than 2 months after removing CD3+ cells, and taking antigen-presenting cell lines of limited amplification generations to obtain the antigen-presenting cells to be transfected.

In the present invention, firstly the fusion gene of TAX and ST40 connected by a linker sequence is ligated onto an expression vector to obtain a recombinant vector; the nucleotide sequence of the TAX is as shown in SEQ ID NO. 11, and is specifically: ATGAACATCAAAGACGAATGGTACTGGGGTAAGAGTAAGCACGCGGTGACTGAGCTCA ACGCGGAGGGATGGATCTTTACTCTCCCGCCAAGTGACAACTACATCGGACGTCACCG GTTGCCGGACGTCCGATTCAGCCAGGAGCTACCCGACGGGACGGTCTACTGGTCGGTG AACCGGAAGAACTTCTTCCGCCGGGACGACAGCCTCCCCTCGGGATGGGTGCAGCGCA TCTACCCGCGTGTAGCTACCAGCTTCAGGACCGCGGAATGA; and the nucleotide sequence of the ST40 is as shown in SEQ ID NO.12, and is specifically: GCCCATTTCCCAGGATTTGGACAGAGCCTCCTATATGGATACCCCGTCTACGTGTTTGGC GATTGTGTACAGGCCGATTGGTGTCCCGTCTCAGGTGGTCTATGTTCCACCCGCCTACA TCGACATGCCCTCCTGGCCACCTGTCCAGAGCACCAACTCACCTGGGACCCCATCGAT GGACGCGTTGTCAGCTCTCCTCTCCAATACCTTATCCCTCGCCTCCCCTCCTTCCCCACC CAGAGAACCTCAAGGACCCTCAAGGTCCT-TACCCCTCCCACCACTCCTGTCTCCCCCA AGGTTC-CACCTGCCTTCTTTCAAT-CAATGCGAAAGCACACCCCCTACCGAAATGGATGCCTGGAACCAACCCTCGGG-GATCAGCTCCCCTCCCTCGCCTTCCCCGAACCTGG-CCTCC GTCCCCAAAACATCTACACCACCTGGG-GAAAAACCGTAGTATGCCTATACCTATACCAGCTTTCCCCACCCATGACATGGCCACTTATACCC-CATGTCATATTCTGCCACCCCAGACAA TTAG-GAGCCTTCCTCACCAAGGTGCCTCTAAAACGATT-AGAAGAACTTCTATACAAAAT GTTCCTACACACAGGGACAGTCATAGTCCTCCCG-GAGGACGACCTACCCACCACAATG TTC-CAACCCGTGAGGGCT; and preferably, the nucleotide sequence of the fusion gene of TAX and ST40 is as shown in SEQ ID NO.13, and is specifically:

ATGAACATCAAAGACGAATGGTACTGGGGTAAGAGTAAGCACGCGGTGAC

TGAGCTCAACGCGGAGGGATGGATCTTTACTCTCCCGCCAAGTGACAACT

ACATCGGACGTCACCGGTTGCCGGACGTCCGATTCAGCCAGGAGCTACCC

GACGGGACGGTCTACTGGTCGGTGAACCGGAAGAACTTCTTCCGCCGGGA

CGACAGCCTCCCCTCGGGATGGGTGCAGCGCATCTACCCGCGTGTAGCTA

CCAGCTTCAGGACCGCGGAATGAGCCACGAACTTCTCTCTGTTAAAGCAA

GCAGGAGATGTTGAAGAAAACCCCGGGCCTGCCCATTTCCCAGGATTTGG

ACAGAGCCTCCTATATGGATACCCCGTCTACGTGTTTGGCGATTGTGTAC

AGGCCGATTGGTGTCCCGTCTCAGGTGGTCTATGTTCCACCCGCCTACAT

CGACATGCCCTCCTGGCCACCTGTCCAGAGCACCAACTCACCTGGGACCC

CATCGATGGACGCGTTGTCAGCTCTCCTCTCCAATACCTTATCCCTCGCC

TCCCCTCCTTCCCCACCCAGAGAACCTCAAGGACCCTCAAGGTCCTTACC

CCTCCCACCACTCCTGTCTCCCCCAAGGTTCCACCTGCCTTCTTTCAATC

AATGCGAAAGCACACCCCCTACCGAAATGGATGCCTGGAACCAACCCTCG

GGGATCAGCTCCCCTCCCTCGCCTTCCCCGAACCTGGCCTCCGTCCCCAA

AACATCTACACCACCTGGGAAAAACCGTAGTATGCCTATACCTATACCA

GCTTTCCCCACCCATGACATGGCCACTTATACCCCATGTCATATTCTGCC

ACCCCAGACAATTAGGAGCCTTCCTCACCAAGGTGCCTCTAAAACGATTA

GAAGAACTTCTATACAAAATGTTCCTACACACAGGGACAGTCATAGTCCT

CCCGGAGGACGACCTACCCACCACAATGTTCCAACCCGTGAGGGCT.

In the present invention, after the recombinant vector is obtained, a lentivirus is packaged with the recombinant vector to obtain a packaged virus. The present invention has no special limitation on the method for packaging the lentivirus, and a conventional method in the art can be adopted.

In the present invention, after the packaged virus is obtained, DC cells are infected with the packaged virus to obtain infected DC cells. The present invention has no special limitation on the method for infecting the DC cells with the packaged virus, and a conventional method in the art can be adopted.

In the present invention, after the infected DC cells are obtained, the trophoblast cells are inoculated into the upper culture chamber of the cell incubator, the infected DC cells obtained in the step S3 are inoculated into the lower culture chamber of the cell incubator, first culture is conducted for 4-6 weeks, second culture is conducted for 1-2 weeks after CD3+ cells are removed, then third culture is conducted for more than 2 months after CD3+ cells are removed, and the antigen-presenting cell lines of limited amplification generations are taken to obtain the antigen-presenting cells to be transfected. The trophoblast cells are preferably prepared by using the following method: culturing peripheral blood mononuclear cells in a 1640 medium containing fetal bovine serum for 9-14 h, and preferably 12 h, to obtain the trophoblast cells; wherein the percentage mass content of the fetal bovine serum in the 1640 medium is 8%-12%, and preferably 10%; the inoculation amount of the trophoblast cells is preferably $0.5 \times 10^6$-$1.5 \times 10^6$/well, and more preferably $1 \times 10^6$/well; and the inoculation amount of the infected DC cells is $0.5 \times 10^6$-$1.5 \times 10^6$/well, and more preferably $1 \times 10^6$/well.

The antigen-presenting cells to be transfected of the present invention can be stably expanded, which can solve the problem that it is difficult to obtain, culture and genetically operate the patient's own DCs; and for cell lines, the limited amplification generations are safer.

The technical solutions in the present invention will be clearly and completely described below in conjunction with the embodiments of the present invention. Apparently, the described embodiments are merely a part rather than all of the embodiments of the present invention. All other embodiments obtained by a person of ordinary skill in the art based on the embodiments of the present invention without creative efforts shall fall within the protection scope of the present invention.

See Table 1 for formulation of relevant reagents in the following examples.

TABLE 1

| Reagent Formula | |
| --- | --- |
| Name | Formulation |
| AP | AIMV containing 2.5% FBS and 0.1% polybrene |
| 1640F | 1640 containing 10% FBS and 250 U/ml IL-2 |
| AF | AIMV containing 10% FBS and 250 U/ml IL-2 |

Example 1 Establishment of Antigen-Presenting Cell Lines with Limited Amplification Generations 1) a fusion gene of TAX and ST40 was synthesized;

2) the fusion gene synthesized in the step 1) was ligated onto an expression vector to obtain a recombinant vector;

3) a lentivirus was packaged with the vector of 2) to obtain a packaged virus according to the instructions of a lentivirus packaging kit (available from Beijing Syngentech Co., LTD.), and DC cells were infected with the packaged virus to obtain infected DC cells;

4) trophoblast cells were inoculated in an upper culture chamber of a cell incubator, the infected DC cells obtained in the step 3) were inoculated in a lower culture chamber of the cell incubator, culture was conducted for 4-6 weeks, then culture was continually conducted for 1-2 weeks after CD3+ cells were removed, and then culture was continually conducted for more than 2 months after CD3+ cells were removed, so as to obtain antigen-presenting cell lines of limited amplification generations.

Implementation Steps

1. Isolation of peripheral blood-derived dendritic cells by adherent method, and activation thereof 1) apheresis blood collection was conducted to isolate PBMCs;

2) the PBMCs were adjusted to $1\times10^6$ cells/mL with the 1640 medium+10% FBS, placed into a Petri dish, and allowed to stand overnight in an incubator containing 5% $CO_2$ at 37° C.; the suspended cells were collected and marked as T+B for later use;

3) the cells attached to the bottom of the Petri dish were pipetted up and down with the 1640 medium+10% FBS+100 IU/mL IL-2, so as to collect adherent monocytes as peripheral blood-derived DCs;

4) the cells were added with 35 μg/mL PHA for stimulation, and cultured for 24 h for later use.

2. Plasmids Preparation 1) shaking protocol: bacterial glycerol stocks were thawed on ice, each 100 μl of the cells were taken and added into 3 ml of a LB medium containing 100 μg/ml of ampicillin, and then activated at 220 rpm and 37° C. for 6 h, the bacterial solutions were respectively cultured in 100 ml of the LB medium containing 100 μg/ml of ampicillin overnight at 220 rpm and 37° C. for culture expansion. The next day, centrifuging was conducted at 4000×g for 10 min to collect precipitate of each bacterial solution.

2) Preparation Works:

a) A solution I was added with RNase A and stored at 4° C.

b) A DNA Wash Buffer was added with 180 ml of ethanol.

c) A HBC Buffer was added with 76 ml of isopropanol.

d) A Buffer N3 was placed on ice, and a 42° C. water bath was prepared.

3) a DNA chromatographic column was added with 3 ml of a GPS Buffer, placed at room temperature for 4 min, centrifuged at 4000×g for 3 min, and then was read for use after the waste solution was discarded.

4) Each 100 ml of the bacteria precipitate was taken and added with 10 ml of Solution I/RNase, inverted up and down, and pipetted up and down for uniform mixing.

5) The solution was added with 10 ml of Solution II, and inverted gently for 8-10 times, and allowed to stand at room temperature for 3 min.

6) The solution was added with 5 ml of pre-chilled Buffer N3, inverted gently for 8-10 times until a white flocculent precipitate formed, and allowed to stand at room temperature for 2 min.

7) The above liquid was transferred into a new 50 ml centrifuge tube using a filter syringe, and measured for its volume.

8) The liquid was added with 0.1 times the volume of a ETR Solution, and inverted gently for 8-10 times.

9) The liquid was placed on ice for 10 min, during which the solution was inverted continuously (the liquid changed from turbid to clear).

10) The liquid was placed in the 42° C. water bath for 5 min, and the liquid turned turbid again.

11) The liquid was centrifuged at 4000×g for 3 min, and the ETR Solution formed a layer at the bottom of the tube.

12) The supernatant was transferred into another new 50 ml centrifuge tube, and measured for its volume.

13) The supernatant was added with 0.5 times the volume of alcohol, inverted gently for 8-10 times, and allowed to stand at room temperature for 2 min.

14) a DNA chromatographic column was added with 20 ml of the above liquid, and centrifuged at 4000×g for 3 min, and then the waste solution was discarded.

15) the step 14 was repeated.

16) the column was added with 10 ml of the HBC Buffer, and centrifuged at 4000×g for 3 min, and then the waste solution was discarded.

17) the column was added with 15 ml of the DNA Wash Buffer, and centrifuged at 4000×g for 3 min, and then the waste solution was discarded.

18) the column was added with 10 ml of the DNA Wash Buffer, and centrifuged at 4000×g for 3 min, and then the waste solution was discarded.

19) After 10 minutes of vacuum centrifugation at 4000×g, the chromatographic column was placed into a new 50 ml centrifuge tube, dropwise added with 800 μl of $dH_2O$ on the central membrane, placed at room temperature for 5 min, and centrifuged at 4000×g for 5 min, such that the plasmid solution was collected into the centrifuge tube.

20) the plasmid solution was added back into the column, and the column was placed at room temperature for 5 min and centrifuged at 4000×g for 5 min, such that the plasmid solution was re-collected into the centrifuge tube, and then the plasmid solution was sub-packaged and then cryopreserved.

2 μl of the sample was taken, 2 μl of $dH_2O$ was used as a control, and their concentrations were determined.

Example 2 Construction of Lentiviral Vector and Transformation of DCs 1) lentivirus packaging: plating density of 293T cells: $1.8\times10^7$, and the cells were cultured in 20 mL of a OPTI-MEM medium at 37° C. under 5% $CO_2$. The dosage of the transfection plasmid obtained in Example 1: the dosage of a plasmid for packaging: 15 μg of a P-ST40-TAX2 plasmid (the plasmid used for preparing immortalized dendritic cells): 15 μg of the plasmid was added into a buffer and mixed uniformly by shaking for 5 s, added with 60 μL of a transfection reagent, mixed uniformly with a pipette for 5 times, and incubated at room temperature for 10 min. The transfection mixture was evenly distributed and added dropwise into the cells, and then the cells were incubated at 37° C. with 5% $CO_2$. 3 h after the transfection, the medium was replaced with a fresh medium, and 37 mL of a OPTI-MEM (6% FBS) medium was added into each T175 culture flask. At 96 h, the supernatant was harvested and added with a concentrated virus solution (SyngenTech Co., LTD.), subjected to sedimentation for 24 h, and centrifuged at 4000 g for 30 min to harvest the viruses for later use.

2) infection of DCs with lentivirus: the peripheral blood-derived DCs obtained in Method 1 were added into a 6-well plate at $3\times10^5$ per well by using 1 mL 1640+10% FBS+0.1% polybrene+100 μL virus supernatant, incubated at 32° C. for 4-6 h, then placed into a $CO_2$ incubator for culture, and supplemented with 2 mL of 1640+10% FBS 4 h later. When cultured to the third day, the cells was transferred to the lower layer of a cell culture insert and marked as Day 0.

3) the T+ B cells obtained in Example 1 were resuspended with 1640+10% FBS+100 IU/mL IL-2, and added into the upper culture chamber of the cell culture insert (12-well plate) as trophoblast cells, with the number of seeded cells being $1\times10^6$ cells/well;

4) the cell culture insert was placed into an incubator containing 5% $CO_2$ at 37° C. for culture, the state of the cells in the lower layer was observed every day, and half of the cell solution was replaced when the cell solution turned yellow;

5) the cells in the upper layer were counted and detected for viability every day, and the cells were replaced with new trophoblast cells when the viability of the trophoblasts in the upper layer was less than 50%;

6) the cells were transferred according to the growth situation, the number of the transferred cells being consistent with the initial number of cells.

a) upon 4-6 weeks of culture, all of the cells in the lower layer were collected, and treated with CD3+ sorting magnetic beads available from Miltenyi Biotec to remove the CD3+ cells;

b) the remaining cells were resuspended with 1640+10% FBS+100 IU/mL IL-2, and placed into an incubator containing 5% CO₂ at 37° C. for culture for 1-2 weeks;

c) the phenotypes of the cells were detected by a flow cytometer, and the aforementioned steps were repeated if there were still CD3+ cells; and the cells were continually cultured in the 1640+10% FBS+100 IU/mL IL-2C medium for 2 months if there were no CD3+ cell, so as to obtain the universal DCs.

Example 3 Construction of Coronavirus-Targeting Universal DC Vaccines (ORF3a, ORF6, ORF7a and ORF8)

1) A fusion gene of HLA-A0201 molecules common in Chinese and the gene of coronavirus open reading frame was synthesized;

2) the fusion gene synthesized in the step 1) was ligated onto an expression vector to obtain a recombinant vector;

3) the recombinant vector of the step 2) was transferred into the universal antigen-presenting cells obtained in the Method 1, and added with puromycin for screening;

4) then the antigen-presenting cells expressing HLA and the protein of coronavirus were obtained after the screening was stable.

Gene of coronavirus open reading frame protein:

The nucleotide sequence of the ORF3a was as shown in SEQ ID NO.1:

ATGGATTTGTTTATGAGAATCTTCACAATTGGAACTGTAACTTTGAAGCA
AGGTGAAATCAAGGATGCTACTCCTTCAGATTTTGTTCGCGCTACTGCAA
CGATACCGATACAAGCCTCACTCCCTTTCGGATGGCTTATTGTTGGCGTT
GCACTTCTTGCTGTTTTTCAGAGCGCTTCCAAAATCATAACCCTCAAAAA
GAGATGGCAACTAGCACTCTCCAAGGGTGTTCACTTTGTTTGCAACTTGC
TGTTGTTGTTTGTAACAGTTTACTCACACCTTTTGCTCGTTGCTGCTGGC
CTTGAAGCCCCTTTTCTCTATCTTTATGCTTTAGTCTACTTCTTGCAGAG
TATAAACTTTGTAAGAATAATAATGAGGCTTTGGCTTTGCTGGAAATGCC
GTTCCAAAAACCCATTACTTTATGATGCCAACTATTTTCTTTGCTGGCAT
ACTAATTGTTACGACTATTGTATACCTTACAATAGTGTAACTTCTTCAAT
TGTCATTACTTCAGGTGATGGCACAACAAGTCCTATTTCTGAACATGACT
ACCAGATTGGTGGTTATACTGAAAAATGGGAATCTGGAGTAAAAGACTGT
GTTGTATTACACAGTTACTTCACTTCAGACTATTACCAGCTGTACTCAAC
TCAATTGAGTACAGACACTGGTGTTGAACATGTTACCTTCTTCATCTACA
ATAAAATTGTTGATGAGCCTGAAGAACATGTCCAAATTCACACAATCGAC
GGTTCATCCGGAGTTGTTAATCCAGTAATGGAACCAATTTATGATGAACC
GACGACGACTACTAGCGTGCCTTTG;

The nucleotide sequence of the ORF6 was as shown in SEQ ID NO.2:

ATGTTTCATCTCGTTGACTTTCAGGTTACTATAGCAGAGATATTACTAAT
TATTATGAGGACTTTTAAAGTTTCCATTTGGAATCTTGATTACATCATAA
ACCTCATAATTAAAAATTTATCTAAGTCACTAACTGAGAATAAATATTCT
CAATTAGATGAAGAGCAACCAATGGAGATTGAT;

The nucleotide sequence of the ORF7a was as shown in SEQ ID NO.3:

ATGAAAATTATTCTTTTCTTGGCACTGATAACACTCGCTACTTGTGAGCT
TTATCACTACCAAGAGTGTGTTAGAGGTACAACAGTACTTTTAAAAGAAC
CTTGCTCTTCTGGAACATACGAGGGCAATTCACCATTTCATCCTCTAGCT
GATAACAAATTTGCACTGACTTGCTTTAGCACTCAATTTGCTTTTGCTTG
TCCTGACGGCGTAAAACACGTCTATCAGTTACGTGCCAGATCAGTTTCAC
CTAAACTGTTCATCAGACAAGAGGAAGTTCAAGAACTTTACTCTCCAATT
TTTCTTATTGTTGCGGCAATAGTGTTTATAACACTTTGCTTCACACTCAA
AAGAAAGACAGAA;

The nucleotide sequence of the ORF8 was as shown in SEQ ID NO.4:

ATGAAATTTCTTGTTTTCTTAGGAATCATCACAACTGTAGCTGCATTTCA
CCAAGAATGTAGTTTACAGTCATGTACTCAACATCAACCATATGTAGTTG
ATGACCCGTGTCCTATTCACTTCTATTCTAAATGGTATATTAGAGTAGGA
GCTAGAAAATCAGCACCTTTAATTGAATTGTGCGTGGATGAGGCTGGTTC
TAAATCACCCATTCAGTACATCGATATCGGTAATTATACAGTTTCCTGTT
TACCTTTTACAATTAATTGCCAGGAACCTAAATTGGGTAGTCTTGTAGTG
CGTTGTTCGTTCTATGAAGACTTTTTAGAGTATCATGACGTTCGTGTTGT
TTTAGATTTCATC;

the linker sequence was as shown in SEQ ID NO.10, and was specifically:

GCCACGAACTTCTCTCTGTTAAAGCAAGCAGGAGATGTTGAAGAAAACCC
CGGGCCT;

The nucleotide sequence of the HLA-A0201 was as shown in SEQ ID NO.14, and was specifically: GCTAGCGCCA CCATGGCCACCATGGCCGT-CATGGCGCCCCGAACCCTCGTCCTGC-TACTCTCGGGGGCT CTGGCCCTGACCCA-GACCTGGGCGGGCTCTCACTCCATGAGGTATTTCTT-CACATCCGT GTCCCGGCCCGGCCGCGGGGAGCCCCGCTT-CATCGCAGTGGGCTACGTGGACGACAC GCAGTTCGTGCGGTTCGACAGCGACGCCGCGAGC-CAGAGGATGGAGCCGCGGGCGCC GTGGA-TAGAGCAGGAGGGTCCGGAGTATTGGGACGGGGA-GACACGGAAAGTGAAGGC CCACTCACAGACT-CACCGAGTGGACCTGGGGACCCTGCGCGGCTACTA-CAACCAGAG CGAGGCCGGTTCT- CACACCGTCCAGAGGATGTATGGCTGCGACGTGGGGTCGGACTGG CGCTTCCTCCGCGGGTAC-CACCAGTACGCCTACGACGGCAAGGATTA-CATCGCCCTGA
AAGAGGACCTGCGCTCTTGGACCGCGGCGGA-CATGGCAGCTCAGACCACCAAGCACA AGTGG-GAGGCGGCCCATGTGGCGGAGCAGTTGAGAGCC-TACCTGGAGGGCACGTGCG
TGGAGTGGCTCCGCAGATACCTGGAGAACGG-GAAGGAGACGCTGCAGCGCACGGACG CCCC-CAAAACGCATATGACTCACCACGCTGTCTCTGAC-CATGAAGCCACCCTGAGGTG
CTGGGCCCTGAGCTTCTACCCTGCGGAGAT-CACACTGACCTGGCAGCGGGATGGGGAG GACCA-GACCCAGGACACGGAGCTCGTGGA-GACCAGGCCTGCAGGGGATGGAACCTTC
CAGAAGTGGGCGGCTGTGGTGGTGCCTTCTGGACAGGAGCAGAGATACACCTGCCATG TGCAGCAT-GAGGGTTTGCCCAAGCCCCTCACCCTGAGATGG-GAGCCGTCTTCCCAGCC CACCATCCC-CATCGTGGGCATCATTGCTGGCCTGGTTCTCTTTGG-AGCTGTGATCACTG GAGCTGTGGTCGCTGCTGT-GATGTGGAGGAGGAAGAGCTCAGA-TAGAAAAGGAGGGA
GCTACTCTCAGGCTGCAAGCAGTGACAGTGCCCA-GGGCTCTGATGTGTCTCTCACAGC TTGTAAAGTG-GATTACAAGGATGACGACGATAAGGAGGGCAGAG-GAAGTCTTCTAACA TGCGGTGACGTGGAG-GAGAATCCCGGCCCTGCCACCATGTCTCGCTCCGT-GGCCTTAG CTGTGCTCGCGC-TACTCTCTCTTTCTGGCCTGGAGGC-TATCCAGCGTACTCCAAAGATT CAGGTTTACT-CACGTCATCCAGCAGAGAATGGAAAGTCAAATTT-CCTGAATTGCTATGT GTCTGGGTTTCATC-CATCCGACATTGAAGTTGACTTACTGAAGAATG-GAGAGAGAATTG AAAAAGTGGAGCATTCA-GACTTGTCTTTCAGCAAGGACTGGTCTTTCTATCT-CTTGTAC TACACTGAATTCACCCCCACTGAAAAA-GATGAGTATGCCTGCCGTGTGAACCATGTGAC TTTGTCACAGCCCAAGATAGTTAAGTGGGATCGA-GACATGTAAGGATCC.

Method: the methods for plasmid extraction and lentivirus packaging were as above;

1. Infection of Cells with Lentivirus

The desired viruses were taken out and thawed in a refrigerator at 4° C. The antigen-presenting cells of limited amplification generations were taken, transferred into a 50 ml centrifuge tube, and centrifuged at 900 rpm for 5 min; then resuspended in 10 ml AP after the centrifugation, and counted; and plated in a 12-well plate according to $1\times10^6$ per well. The culture supernatant was pipetted and mixed with the viruses uniformly, and added into the corresponding wells. The challenged cells were incubated at a temperature of 32° C. for 4-6 h.

2. Cell Culture

Day 1: the state of the cells was observed under a microscope; the challenged suspension cells were supplemented with 2 ml of an AF solution in each well, and then placed into an incubator containing 5% $CO_2$ at 37° C. for continued culture;

Day 3: the cells in each well were transferred into a 15 ml centrifuge tube by a pipette, and centrifuged at 1000 rpm for 5 min; the supernatant was discarded after the centrifugation, the residue was resuspended in 5 ml of the AF medium, the resuspended cells were transferred into a T25 culture flask and then added with the corresponding antibiotic (puromycin), mixed uniformly and placed into an incubator containing 5% $CO_2$ at 37° C. for culture;

Day 5: each flask was supplemented with 7 ml of the AF medium and the corresponding antibiotic (puromycin);

Day 6: the cells were expanded, transferred into a 50 ml centrifuge tube by a pipette, and centrifuged at 600 rpm for 5 min; the supernatant was discarded after the centrifugation, the residue was resuspended in 20-30 ml of the 1640 F medium, and the resuspended cells were transferred into a T75 culture flask and then added with the corresponding antibiotic (puromycin), shaken uniformly, and placed into an incubator containing 5% $CO_2$ at 37° C. for culture;

Day 8: the cells were expanded. the cells were transferred into a 50 ml centrifuge tube by a pipette and centrifuged at 600 rpm for 5 min; the supernatant was discarded after the centrifugation, the residue was resuspended in 50 ml of the 1640 F medium, the resuspended cells were transferred into a T75 culture flask and then added with the corresponding antibiotic (puromycin), shaken uniformly and placed into an incubator containing 5% $CO_2$ at 37° C. for culture;

Day 10: the cells were expanded. the cells were transferred into a 50 ml centrifuge tube by a pipette and centrifuged at 900 rpm for 5 min; the supernatant was discarded after the centrifugation, the residue was resuspended in the 1640 F medium, the resuspended cells were transferred into a T75 culture flask (200 ml/flask), shaken uniformly and placed into an incubator containing 5% $CO_2$ at 37° C. for culture;

the cells were taken to extract the genome, the genome was detected for the transferred gene, and the coronavirus-targeting universal DC cell vaccine was obtained after the sequencing was correct.

Example 4 Induced Culture of Killer T Cells of the Coronavirus-Targeting Universal DC Vaccine of Example 3

1) CD3+ T cells or CD8+ T cells were adjusted to $1\times10^6$ cells/mL by a X-VIVO medium, 2 mL of the adjusted cells were plated into a 6-well plate, the resultant coronavirus-targeting universal antigen-presenting cells were added into the wells according to a ratio of 1:100-1:500, and preferably 1:200, and marked as Day 0.

2) After co-cultured for 48 h, the cells were added with IL-2 every day according to the volume of the medium from Day 2, with the final concentration being 50-1000 IU/mL, and preferably 50 IU/mL;

3) upon Day 5, half of the solution was replaced (X-VIVO+50 IU/mL IL-2) when the medium turned yellow. The medium was supplemented according to the growth situation of the cells to maintain the cell density at $0.5\times10^6$-$1\times10^6$ cells/mL;

4) the cells were harvested on Day 21 as the CTLs;

Killing Experiment-LDH Method 1) the target cells were collected and centrifuged at 1000 rpm for 5 min;

2) the cells were washed once with PBS and centrifuged at 1000 rpm for 5 min; 3) the cells were resuspended with 1640+2% FBS, then counted and adjusted to $8\times10^4$ cells/mL, and divided into each well of a 96-well plate (with a U-shaped bottom) at 50 μL/well for later use;

4) effector cells were collected and centrifuged at 1000 rpm for 5 min;

5) the cells were washed once with PBS and centrifuged at 1000 rpm for 5 min;

6) the cells were resuspended with 1640+2% FBS and counted, and then divided into each well of a 96-well plate (with a U-shaped bottom) at 50 μL/well, with the multiplicity of infection (MOI) being set at 10:1, 5:1, 2.5:1 and 1.25:1;

7) after the cells were co-incubated at 37° C. under 5% $CO_2$ for 3.5 h, a LDH test was conducted;

Analysis of specific cell ratio in killer T cells:

a) the obtained CTL cells were added with the corresponding universal antigen-presenting cells according to a ratio of 200:1, and co-cultured for 24 h;

b) the culture was centrifuged at 300 g for 5 min;

c) the supernatant was discarded, and the residue was added with 1 mL 1×PBS, and centrifuged at 300 g for 5 min;

d) 1×10$^6$ cells were added into a tube, and co-stained with CD3, CD8, CD4 and CD137 antibodies, and then incubated at room temperature with protection from light for 30 min;

e) the cells were washed twice with PBS, and centrifuged at 1,000 rpm for 5 min;

f) the precipitate was resuspended in PBS and tested on the machine;

g) the TCR frequency analysis and TCR sequencing analysis of killer T cells were carried out by Hangzhou Repugene Technology Co., Ltd.

See Table 2 for the original HLA typing results of the universal DC vaccine.

TABLE 2

HLA typing results of universal DC vaccine

| HLA-A | | HLA-B | | HLA-C | |
|---|---|---|---|---|---|
| A2402 | A1101 | B1511 | B1505 | C0303 | C0401 |

The specific CTLs were cultured with the universal DC cell vaccine constructed in Example 3 and used for killing the target cells infected with the corresponding HLA and coronavirus protein virus-vector, and the results showed that: the universal DC vaccine had a specific killing effect on target cells infected with the viruses of A1101, C0301, A0207, A0201, B4601, C0304, B1501, and B5101, which indicated that the different HLA genes that can be introduced by genetic engineering means had the same function as the original A1101, could effectively stimulate the CTLs when combined with different ORFs, and had a certain killing effect on the target cells. Therefore, universal DC cell vaccines suitable for more HLAs could be constructed by introducing other HLAs through an exogenous gene introduction method based on the universal DC cell vaccine.

Figure 2:
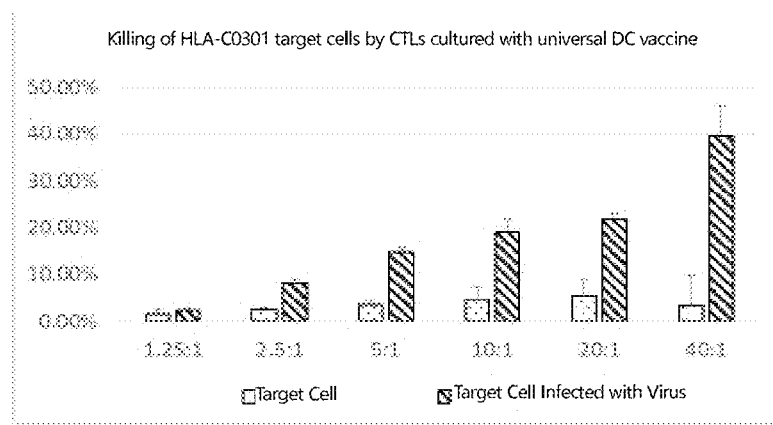
FIG. 2 shows the killing effect of CTLs cultured with the universal DC vaccine of Example 3 on HLA-C0301 target cells in Example 4.
Figure 3:
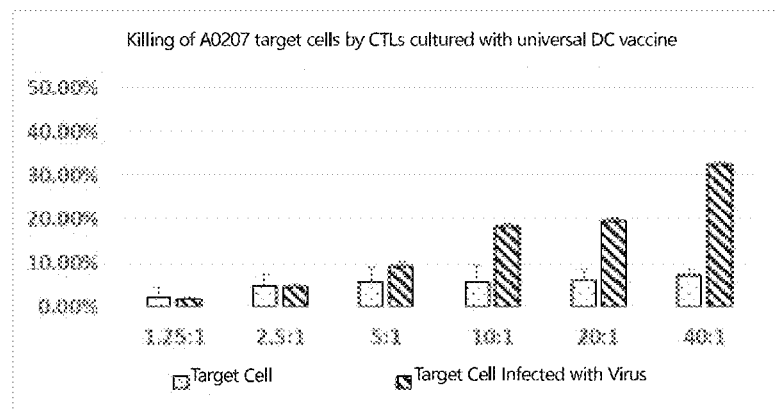
FIG. 3 shows the killing effect of CTLs cultured with the universal DC vaccine of Example 3 on HLA-A0207 target cells in Example 4.
Figure 4:
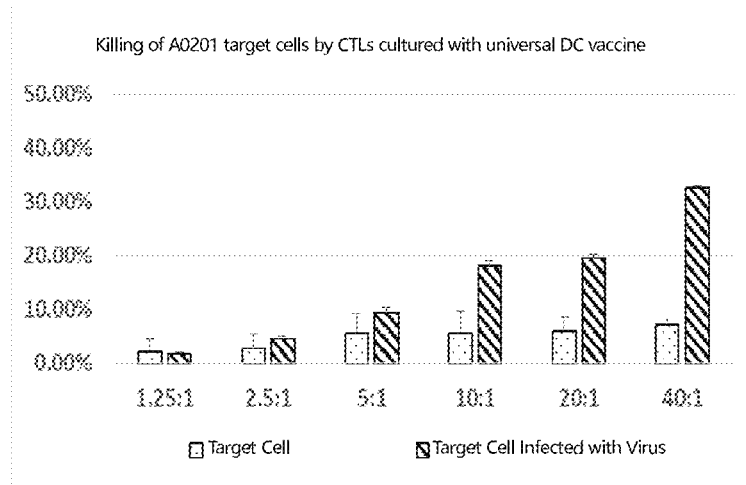
FIG. 4 shows the killing effect of CTLs cultured with the universal DC vaccine of Example 3 on HLA-A0201 target cells in Example 4.
Figure 5:
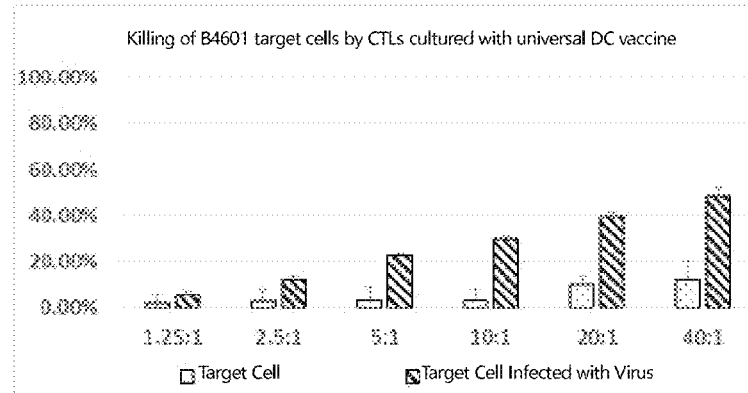
FIG. 5 shows the killing effect of CTLs cultured with the universal DC vaccine of Example 3 on HLA-B4601 target cells in Example 4.
Figure 6:
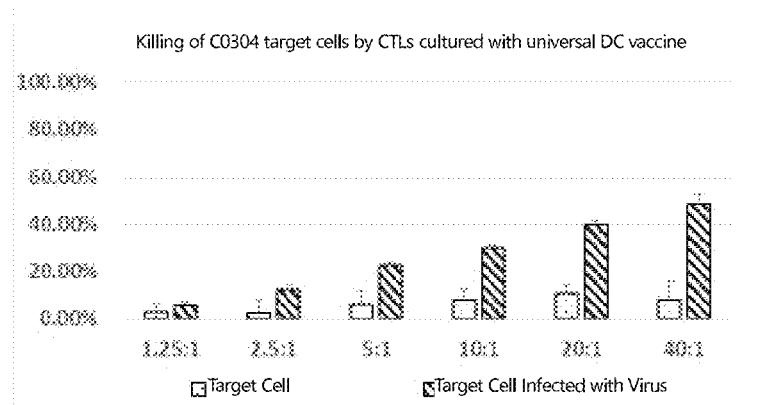
FIG. 6 shows the killing effect of CTLs cultured with the universal DC vaccine of Example 3 on HLA-C0304 target cells in Example 4.
Figure 7:
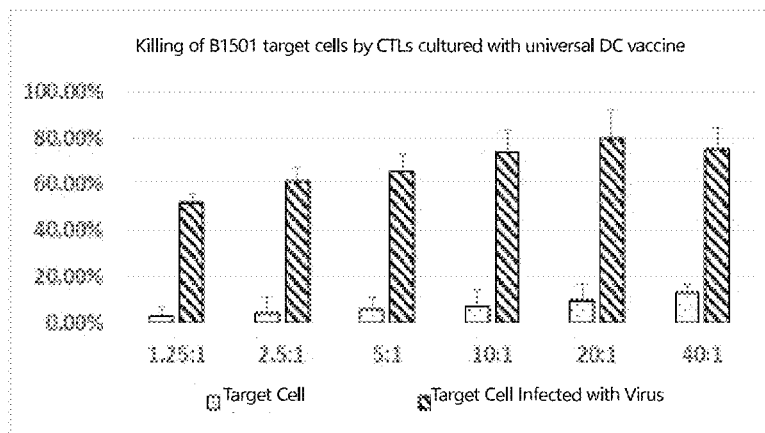
FIG. 7 shows the killing effect of CTLs cultured with the universal DC vaccine of Example 3 on HLA-B1501 target cells in Example 4.
Figure 8:
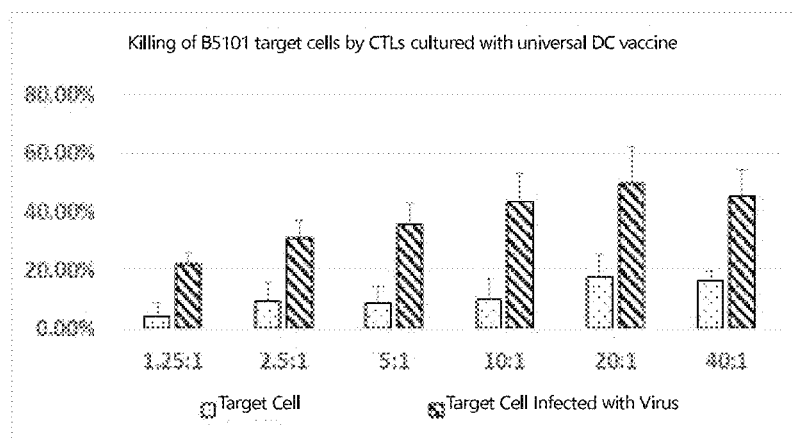
FIG. 8 shows the killing effect of CTLs cultured with the universal DC vaccine of Example 3 on B5101 target cells in Example 4.

The killing effect of the CTLs cultured with the universal DC vaccine of Example 3 on the HLA-A1101 target cells was shown in FIG. 1; the killing effect of the CTLs cultured with the universal DC vaccine of Example 3 on the HLA-C0301 target cells was shown in FIG. 2; the killing effect of the CTLs cultured with the universal DC vaccine of Example 3 on the HLA-A0207 target cells was shown in FIG. 3; the killing effect of the CTLs cultured with the universal DC vaccine of Example 3 on the HLA-A0201 target cells was shown in FIG. 4; the killing effect of the CTLs cultured with the universal DC vaccine of Example 3 on the HLA-B4601 target cells was shown in FIG. 5; the killing effect of the CTLs cultured with the universal DC vaccine of Example 3 on the HLA-C0304 target cells was shown in FIG. 6. The killing effect of the CTLs cultured with the universal DC vaccine of Example 3 on the HLA-B1501 target cells was shown in FIG. 7; and the killing effect of the CTLs cultured with the universal DC vaccine of Example 3 on the HLA-B5101 target cells was shown in FIG. 8.

Example 5

Figure 9:
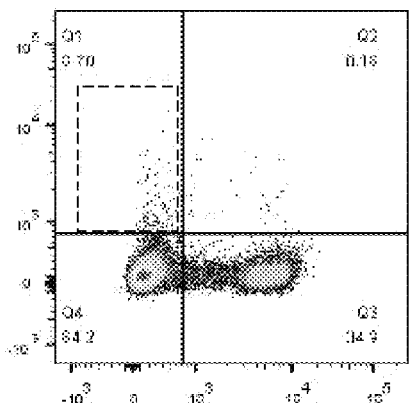
FIG. 9 shows the ratio of activated cells in control in Example 5.
Figure 10:
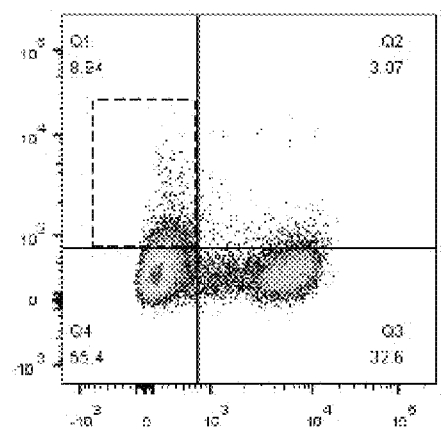
FIG. 10 shows the ratio of activated cells in CTLs against ORF3a in Example 5.
Figure 11:
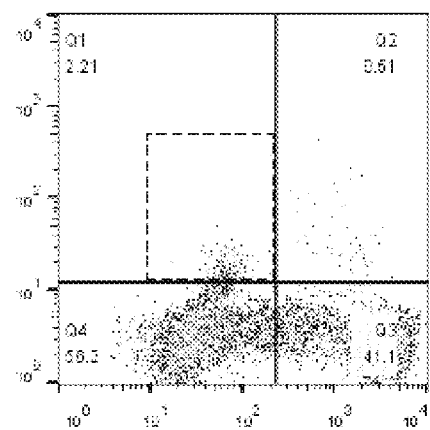
FIG. 11 shows the ratio of activated cells in CTLs against ORF6 in Example 5.
Figure 12:
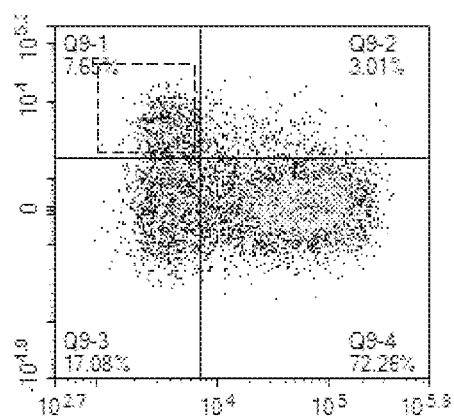
FIG. 12 shows the ratio of activated cells in CTLs against ORF7a in Example 5.
Figure 13:
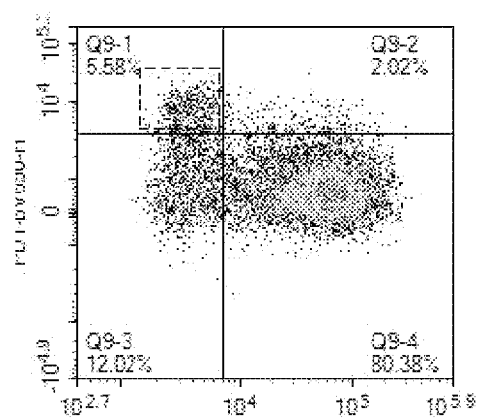
FIG. 13 shows the ratio of activated cells in CTLs against ORF8 in Example 5.
Figure 14:
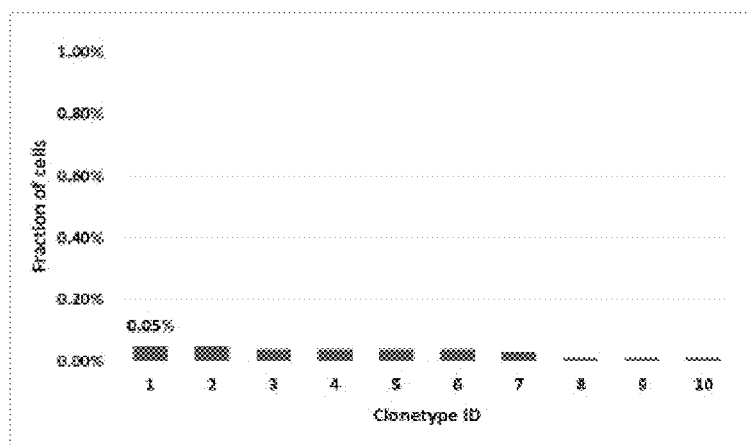
FIG. 14 shows the analysis result of TCR distribution frequency of cells cultured without stimulation by universal DC cells in Example 5.
Figure 15:
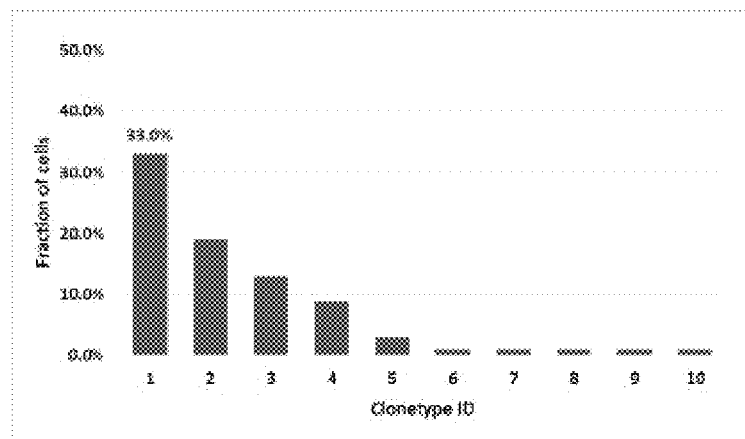
FIG. 15 shows the analysis result of TCR distribution frequency of CTL cells against ORF3a in Example 5.
Figure 16:
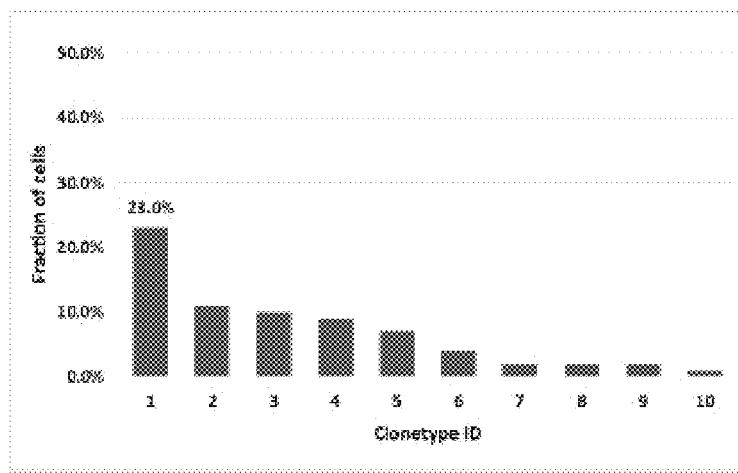
FIG. 16 shows the analysis result of TCR distribution frequency of CTL cells against ORF6 in Example 5.
Figure 17:
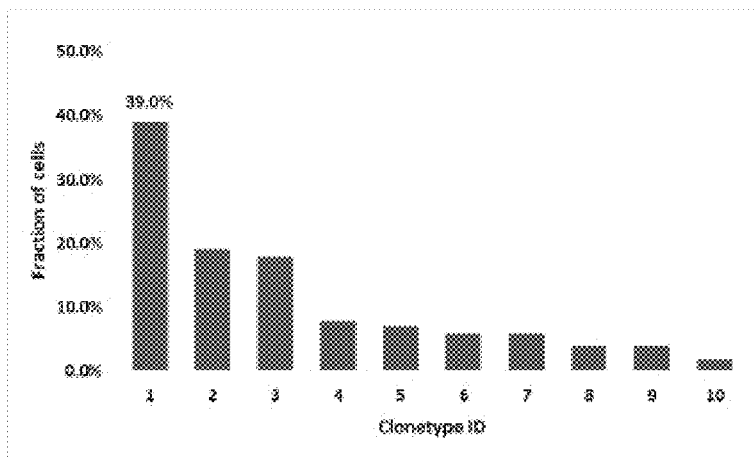
FIG. 17 shows the analysis result of TCR distribution frequency of CTL cells against ORF7a in Example 5.
Figure 18:
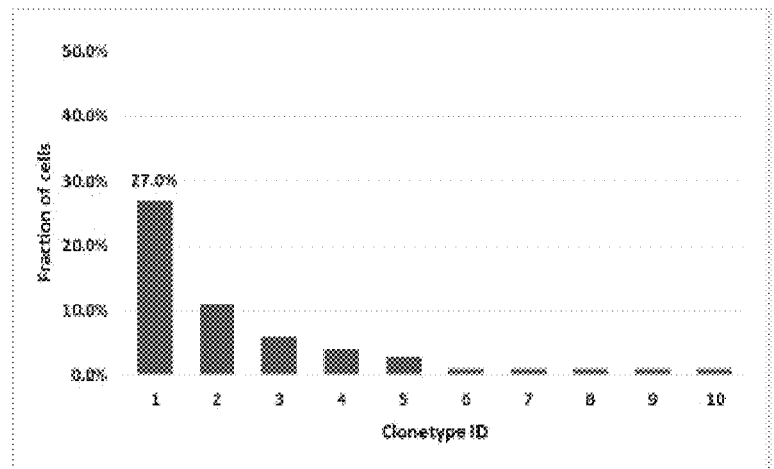
FIG. 18 shows the analysis result of TCR distribution frequency of CTL cells against ORF8 in Example 5.

The CTLs were cultured with stimulation by the universal DC cell vaccine constructed in Example 3, then added with the universal DC cells for secondary stimulation, and detected for the expression of CD137. The results were shown in FIGS. 9-10, wherein FIG. 9 showed the ratio of activated cells in control, FIG. 10 showed the ratio of activated cells in CTLs against ORF3a, FIG. 11 showed the ratio of activated cells in CTLs against ORF6, FIG. 12 showed the ratio of activated cells in CTLs against ORF7a, and FIG. 13 showed the ratio of activated cells in CTLs against ORF8. The results showed that: 8.94%, 2.21%, 7.65%, and 5.58% of the cells were in the activated state (in the dotted box). Sequencing analysis of 10×transcriptomes and VDJ was conducted on the CTL cells, and the results were shown in FIGS. 14-18, wherein FIG. 14 showed the analysis result of TCR distribution frequency of cells cultured without stimulation by the universal DC cells, FIG. 15 showed the analysis result of TCR distribution frequency of CTL cells against ORF3a, FIG. 16 showed the analysis result of TCR distribution frequency of CTL cells against ORF6, FIG. 17 showed the analysis result of TCR distribution frequency of CTL cells against ORF7a, and FIG. 18 showed the analysis result of TCR distribution frequency of CTL cells against ORF8. The results showed that: in the TCR distribution of CD137+ T cells, there were 33%, 23%, 39% and 27% of high-frequency clones, compared with the cells cultured without stimulation by the universal DC cell vaccine having the highest TCR frequency of only 0.05%. Therefore, it could be proved that the universal DC cell vaccine can effectively stimulate specific T cells.

Example 6 Construction of Universal DC Cell Vaccine Targeting Coronavirus E Protein This example was the same as Example 3 except that the gene of coronavirus open reading frame protein in Example 3 was replaced with the gene encoding the coronavirus E protein, and the fused HLA molecules were: A3303, A3001, B5401, B4006, and C0801; the nucleotide sequence of the gene of coronavirus E protein was as shown in SEQ ID NO.5, and was specifically:

```
ATGTACTCATTCGTTTCGGAAGAGACAGGTACGTTAATAGTTAATAGCGT
ACTTCTTTTTCTTGCTTTCGTGGTATTCTTGCTAGTTACACTAGCCATCC
TTACTGCGCTTCGATTGTGTGCGTACTGCTGCAATATTGTTAACGTGAGT
CTTGTAAAACCTTCTTTTTACGTTTACTCTCGTGTTAAAAATCTGAATTC
TTCTAGAGTTCCTGATCTTCTGGTC.
```

Example 7

The E-protein-specific CTLs were cultured with the universal DC cell vaccine targeting the coronavirus E protein as constructed in Example 6 and used for killing the target cells infected with the corresponding HLA virus, and the results showed that: the universal DC vaccine had a specific killing effect on target cells infected with the viruses of A3303, A3001, B5401, B4006, C0801 and C0401, which indicated that the specific HLA molecules that can be introduced by genetic engineering means had the same function as the original C0401, could effectively stimulate the CTLs, and had a certain killing effect on the target cells. Therefore, universal DC cell vaccines suitable for more HLAs could be constructed by introducing other HLAs through a exogenous gene introduction method based on the universal DC cell vaccine.

Figure 19:
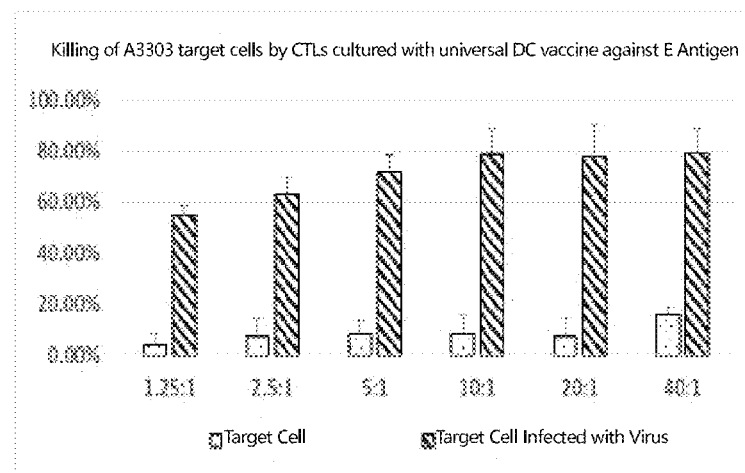
FIG. 19 shows the killing effect of CTLs cultured with the universal DC vaccine of Example 6 on HLA-A3303 target cells in Example 7.
Figure 20:
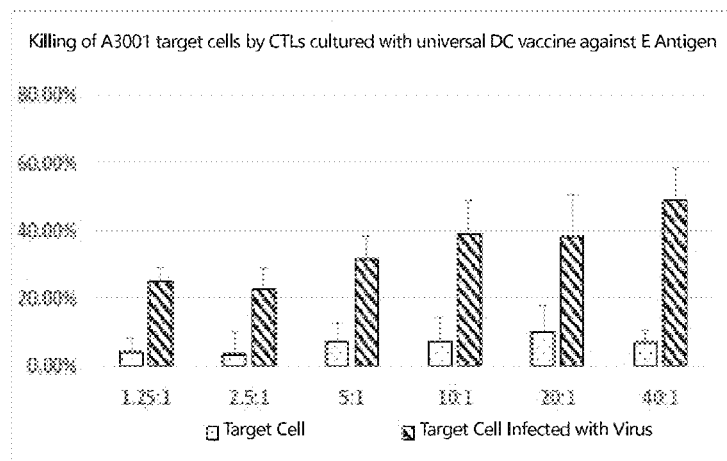
FIG. 20 shows the killing effect of CTLs cultured with the universal DC vaccine of Example 6 on HLA-A3001 target cells in Example 7.
Figure 21:
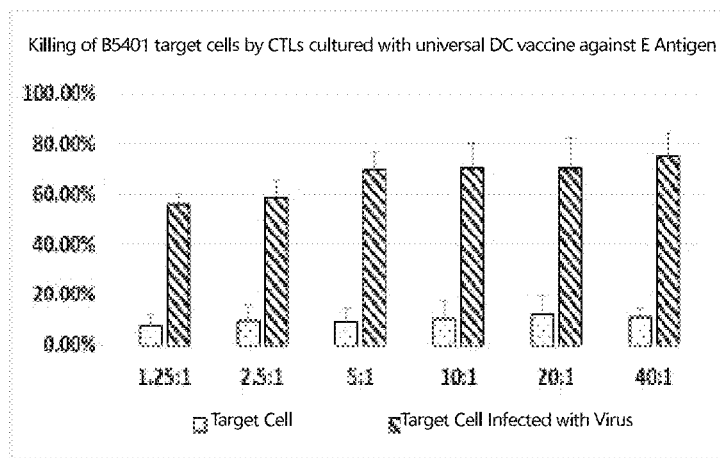
FIG. 21 shows the killing effect of CTLs cultured with the universal DC vaccine of Example 6 on HLA-B4006 target cells in Example 7.
Figure 22:
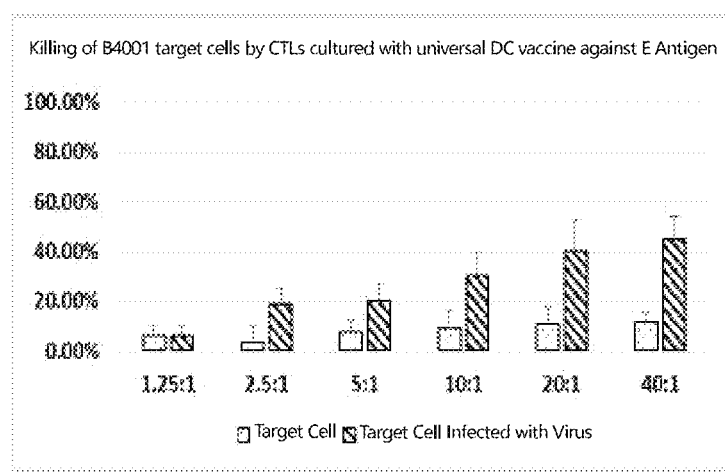
FIG. 22 shows the killing effect of CTLs cultured with the universal DC vaccine of Example 6 on HLA-B5401 target cells in Example 7.
Figure 23:
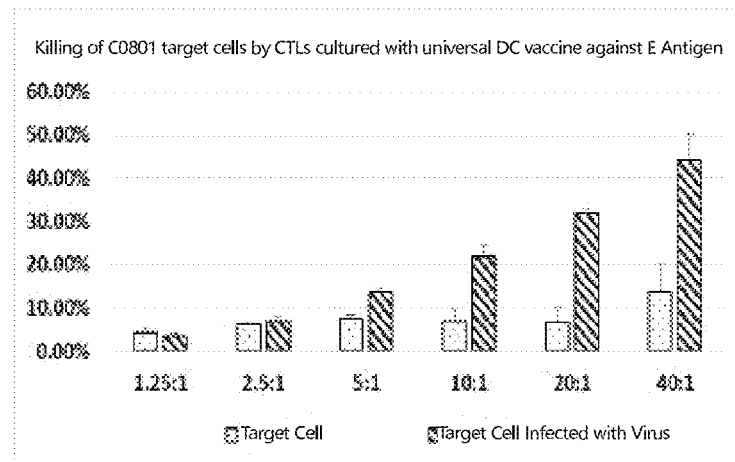
FIG. 23 shows the killing effect of CTLs cultured with the universal DC vaccine of Example 6 on HLA-C0801 target cells in Example 7.
Figure 24:
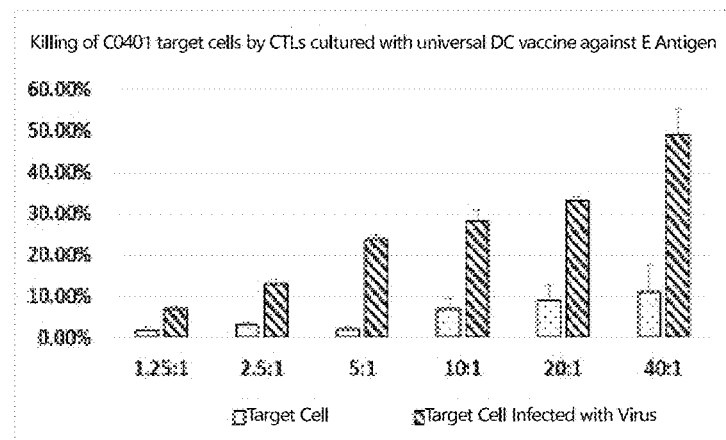
FIG. 24 shows the killing effect of CTLs cultured with the universal DC vaccine of Example 6 on HLA-C0401 target cells in Example 7.
Figure 25:
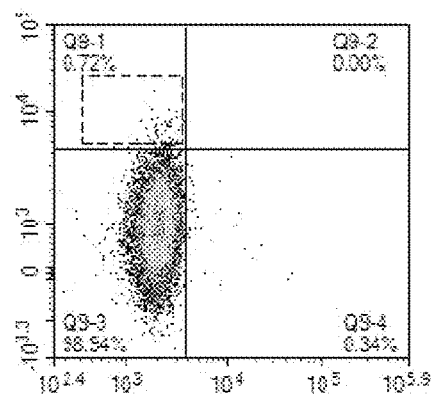
FIG. 25 shows the ratio of activated ones in cells cultured without stimulation by universal DC cells in Example 8.
Figure 26:
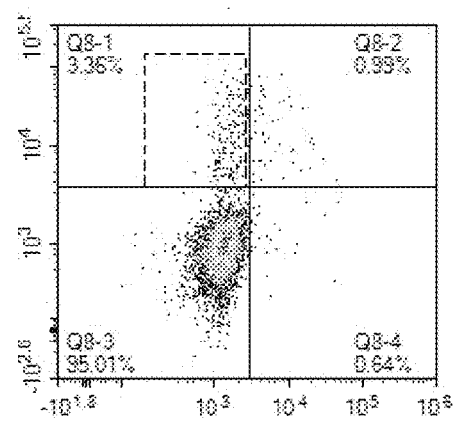
FIG. 26 shows the ratio of activated cells in CTLs cultured with stimulation by the HLA-A3303 universal DC cells of Example 6 in Example 8.
Figure 27:
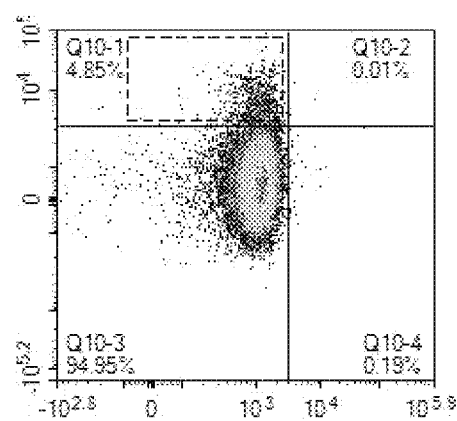
FIG. 27 shows the ratio of activated cells in CTLs cultured with stimulation by the HLA-A3001 universal DC cells of Example 6 in Example 8.
Figure 28:
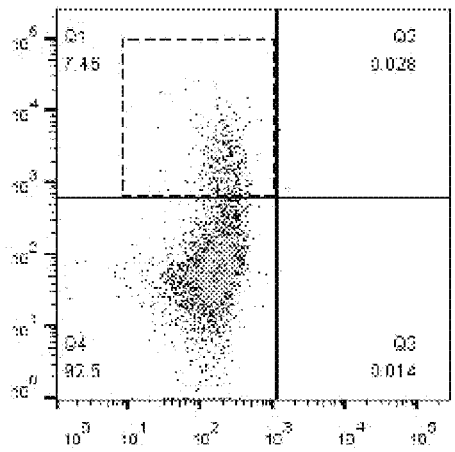
FIG. 28 shows the ratio of activated cells in CTLs cultured with stimulation by the HLA-B4006 universal DC cells of Example 6 in Example 8.
Figure 29:
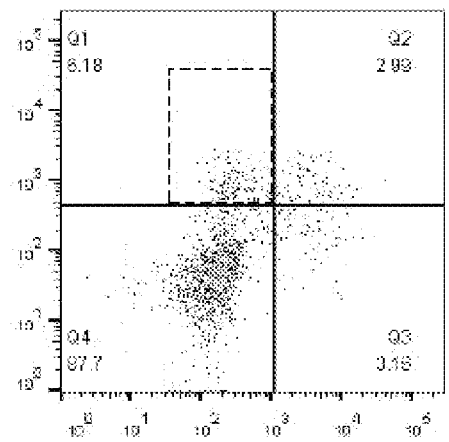
FIG. 29 shows the ratio of activated cells in CTLs cultured with stimulation by the HLA-B5401 universal DC cells of Example 6 in Example 8.
Figure 30:
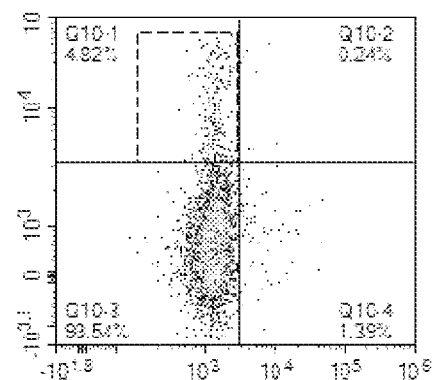
FIG. 30 shows the ratio of activated cells in CTLs cultured with stimulation by the HLA-C0801 universal DC cells of Example 6 in Example 8.
Figure 31:
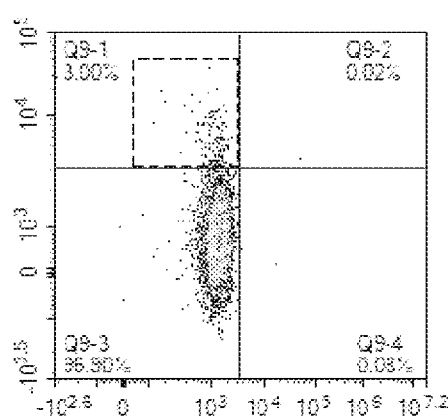
FIG. 31 shows the ratio of activated cells in CTLs cultured with stimulation by the HLA-C0401 universal DC cells of Example 6 in Example 8.
Figure 32:
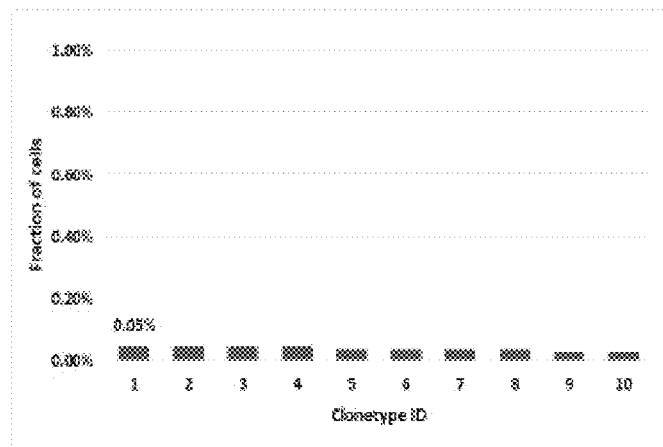
FIG. 32 shows the analysis result of TCR distribution frequency of cells cultured without universal DC cells in Example 8.
Figure 33:
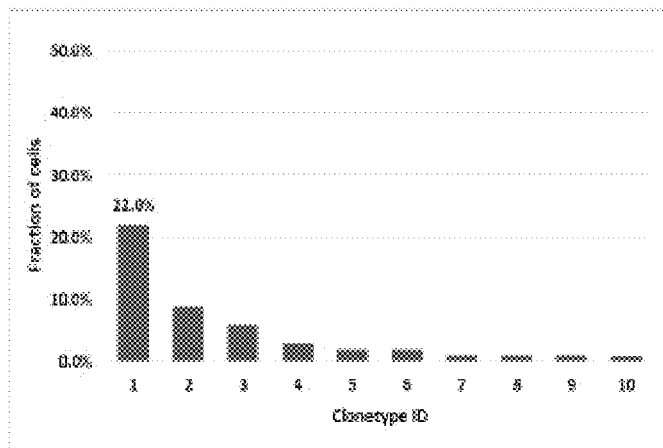
FIG. 33 shows the analysis result of TCR distribution frequency of CTL cells cultured with stimulation by the HLA-A3303 universal DC cells of Example 6 in Example 8.
Figure 34:
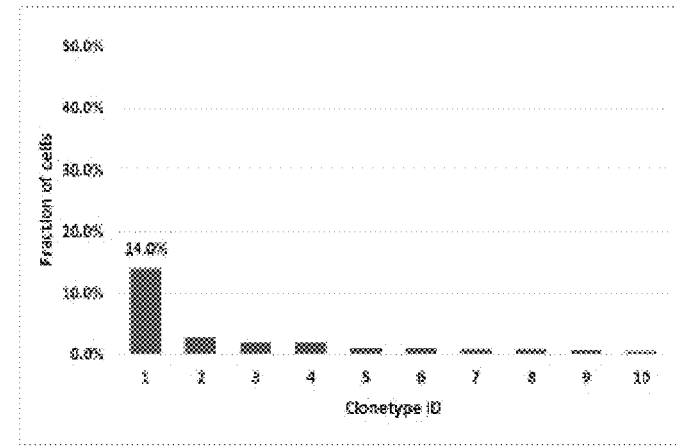
FIG. 34 shows the analysis result of TCR distribution frequency of CTL cells cultured with stimulation by the HLA-A3001 universal DC cells of Example 6 in Example 8.
Figure 35:
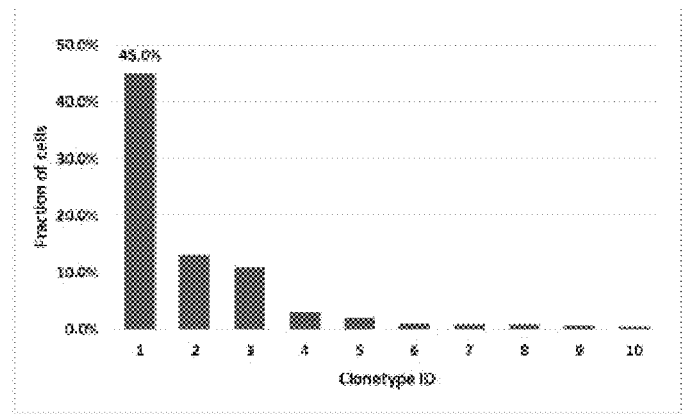
FIG. 35 shows the analysis result of TCR distribution frequency of CTL cells cultured with stimulation by the HLA-B4006 universal DC cells of Example 6 in Example 8.
Figure 36:
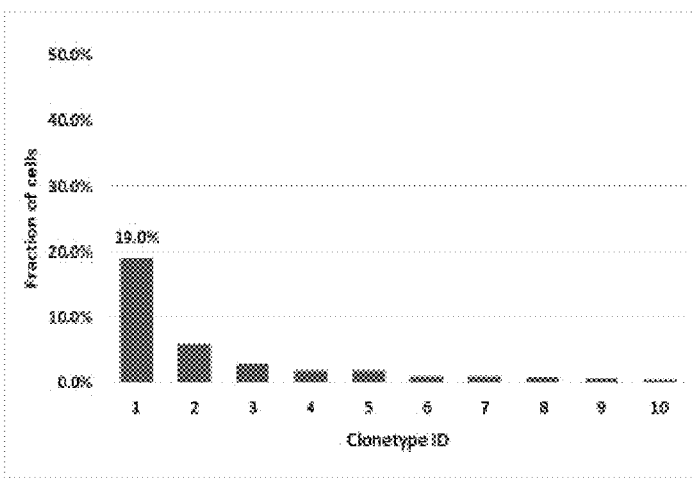
FIG. 36 shows the analysis result of TCR distribution frequency of CTL cells cultured with stimulation by the HLA-B5401 universal DC cells of Example 6 in Example 8.
Figure 37:
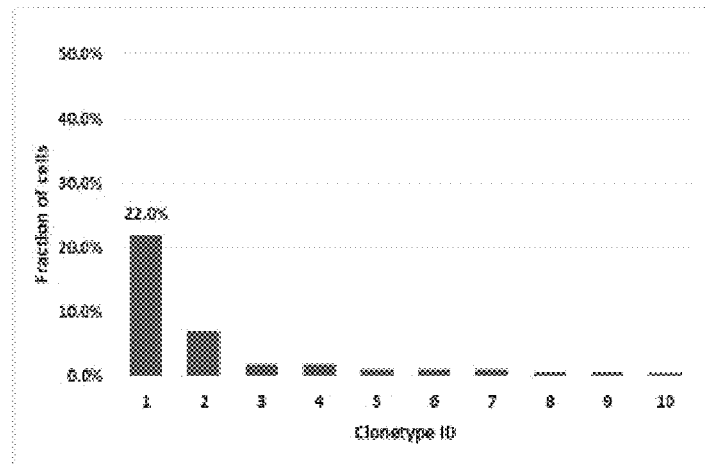
FIG. 37 shows the analysis result of TCR distribution frequency of CTL cells cultured with stimulation by the HLA-C0801 universal DC cells of Example 6 in Example 8.
Figure 38:
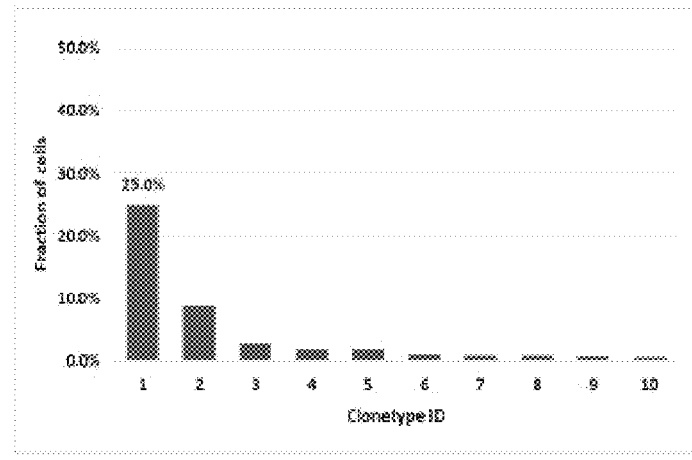
FIG. 38 shows the analysis result of TCR distribution frequency of CTL cells cultured with stimulation by the HLA-C0401 universal DC cells of Example 6 in Example 8.
Figure 39:
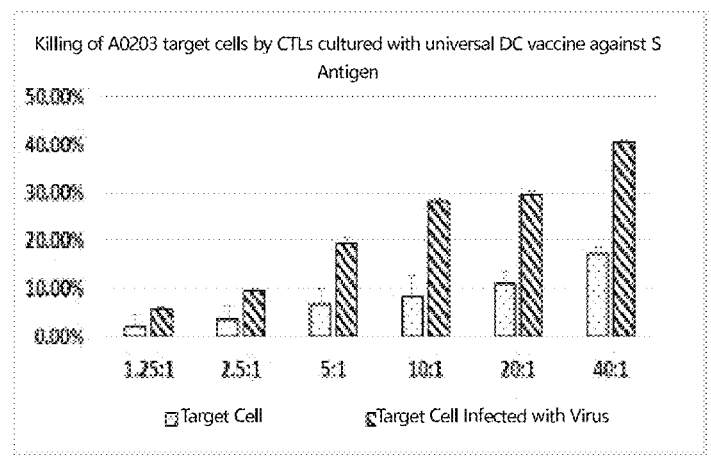
FIG. 39 shows the killing effect of CTLs cultured with the universal DC vaccine of Example 9 on HLA-A0203 target cells in Example 10.

The killing effect of the CTLs cultured with the universal DC vaccine of Example 6 on the HLA-A3303 target cells was shown in FIG. 19; the killing effect of the CTLs cultured with the universal DC vaccine of Example 6 on the HLA-A3001 target cells was shown in FIG. 20; the killing effect of the CTLs cultured with the universal DC vaccine of Example 6 on the HLA-B4006 target cells was shown in FIG. 21; the killing effect of the CTLs cultured with the universal DC vaccine of Example 6 on the HLA-B5401 target cells was shown in FIG. 22; the killing effect of the CTLs cultured with the universal DC vaccine of Example 6 on the HLA-C0801 target cells was shown in FIG. 23; and the killing effect of the CTLs cultured with the universal DC vaccine of Example 6 on the HLA-C0401 target cells was shown in FIG. 24.

Example 8

Figure 40:
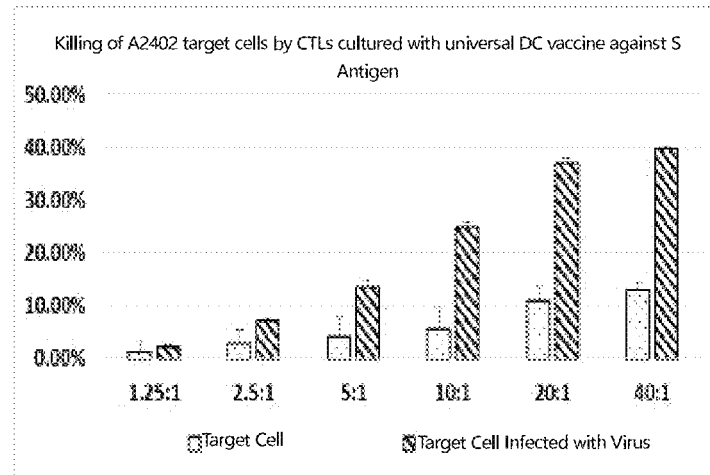
FIG. 40 shows the killing effect of CTLs cultured with the universal DC vaccine of Example 9 on HLA-A2402 target cells in Example 10.
Figure 41:
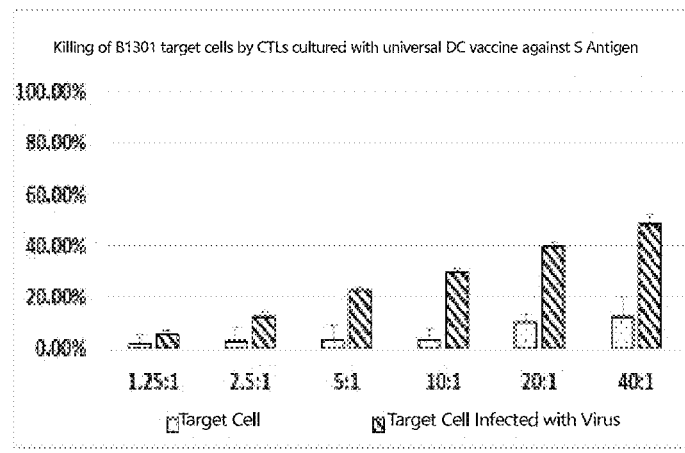
FIG. 41 shows the killing effect of CTLs cultured with the universal DC vaccine of Example 9 on HLA-B1301 target cells in Example 10.
Figure 42:
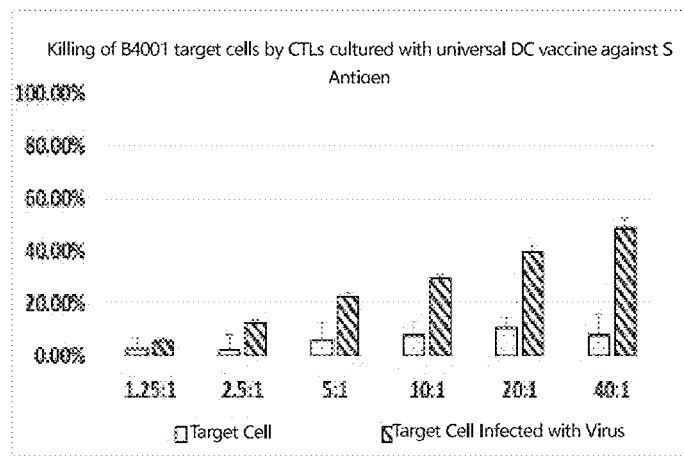
FIG. 42 shows the killing effect of CTLs cultured with the universal DC vaccine of Example 9 on HLA-B4001 target cells in Example 10.
Figure 43:
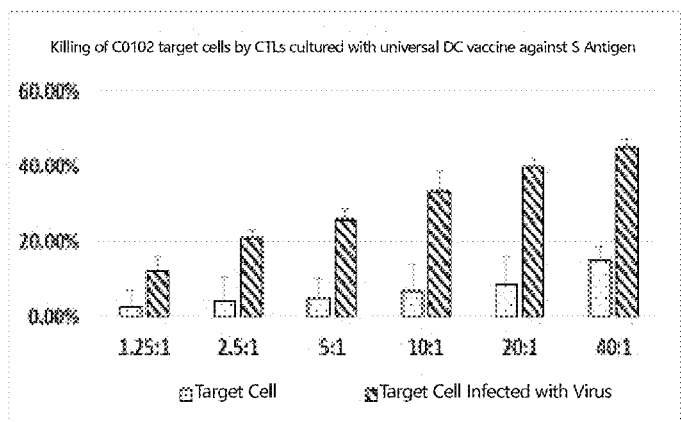
FIG. 43 shows the killing effect of CTLs cultured with the universal DC vaccine of Example 9 on HLA-C0102 target cells in Example 10.
Figure 44:
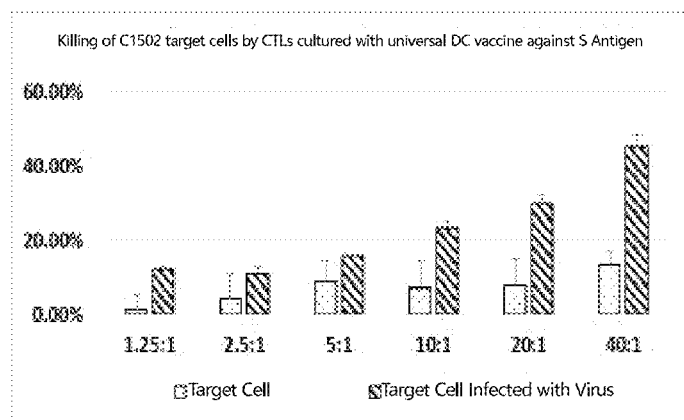
FIG. 44 shows the killing effect of CTLs cultured with the universal DC vaccine of Example 9 on HLA-C1502 target cells in Example 10.

The CTLs were cultured with stimulation by the universal DC cell vaccine targeting the coronavirus E protein as constructed in Example 6, then added with the universal DC cells for secondary stimulation, and detected for the expression of CD137. The results were shown in FIGS. 25-31, wherein FIG. 25 showed the ratio of activated ones in cells cultured without stimulation by the universal DC cells, FIG. 26 showed the ratio of activated cells in CTLs cultured with stimulation by the A3303 universal DC cells of Example 6, FIG. 27 showed the ratio of activated cells in CTLs cultured with stimulation by the A3001 universal DC cells of Example 6, FIG. 28 showed the ratio of activated cells in CTLs cultured with stimulation by the B4006 universal DC cells of Example 6, FIG. 29 showed the ratio of activated cells in CTLs cultured with stimulation by the B5401 universal DC cells of Example 6, FIG. 30 showed the ratio of activated cells in CTLs cultured with stimulation by the C0401 universal DC cells of Example 6, and FIG. 31 showed the ratio of activated cells in CTLs cultured with stimulation by the C0801 universal DC cells of Example 6. The results showed that: among the CTLs cultured with stimulation by the universal DC cell vaccine targeting coronavirus E proteins of different HLA typings as constructed in Example 6, 3.36%, 4.85%, 7.45%, 6.18%, 4.82% and 3.00% of the cells were in the activated state (in the dotted box). Sequencing analysis of 10×transcriptomes and VDJ was conducted on the CTLs, and the results were shown in FIGS. 32-38, wherein FIG. 32 showed the analysis result of TCR distribution frequency of cells cultured without stimulation by the universal DC cells, FIG. 33 showed the analysis result of TCR distribution frequency of CTL cells cultured with stimulation by the universal DC cells against A3303 of Example 6, FIG. 34 showed the analysis result of TCR distribution frequency of CTL cells cultured with stimulation by the universal DC cells against A3001 of Example 6, FIG. 35 showed the analysis result of TCR distribution frequency of CTL cells cultured with stimulation by the universal DC cells against B4006 of Example 6, FIG. 36 showed the analysis result of TCR distribution frequency of CTL cells cultured with stimulation by the universal DC cells against B5401 of Example 6, FIG. 37 showed the analysis result of TCR distribution frequency of CTL cells cultured with stimulation by the universal DC cells against C0401 of Example 6, and FIG. 38 showed the analysis result of TCR distribution frequency of CTL cells cultured with stimulation by the universal DC cells against C0801 of Example 6. The results showed that: in the TCR distribution of CD137+ T cells among the CTLs cultured with stimulation by the universal DC cell vaccine targeting the coronavirus E protein as constructed in Example 6, there were 22%, 12%, 45%, 19%, 22% and 25% of high-frequency clones, compared with the cells cultured without stimulation by the universal DC cell vaccine having the highest TCR frequency of only 0.05%. Therefore, it could be proved that the universal DC vaccine could effectively stimulate specific T cells.

Example 9 Construction of Universal DC Cell Vaccine Targeting Coronavirus S Protein This example was the same as Example 3 except that the gene of coronavirus open reading frame protein in Example 3 was replaced with the gene encoding the coronavirus S protein, and the fused HLAs were respectively: A0203, B1301, B4001, C0102, and C1502; the nucleotide sequence of the gene of coronavirus S protein was as shown in SEQ ID NO.6, and was specifically:

```
ATGGCAGATTCCAACGGTACTATTACCGTTGAAGAGCTTAAAAAGCTCCT
TGAACAATGGAACCTAGTAATAGGTTTCCTATTCCTTACATGGATTTGTC
TTCTACAATTTGCCTATGCCAACAGGAATAGGTTTTTGTATATAATTAAG
TTAATTTTCCTCTGGCTGTTATGGCCAGTAACTTTAGCTTGTTTTGTGCT
TGCTGCTGTTTACAGAATAAATTGGATCACCGGTGGAATTGCTATCGCAA
TGGCTTGTCTTGTAGGCTTGATGTGGCTCAGCTACTTCATTGCTTCTTTC
AGACTGTTTGCGCGTACGCGTTCCATGTGGTCATTCAATCCAGAAACTAA
CATTCTTCTCAACGTGCCACTCCATGGCACTATTCTGACCAGACCGCTTC
TAGAAAGTGAACTCGTAATCGGAGCTGTGATCCTTCGTGGACATCTTCGT
ATTGCTGGACACCATCTAGGACGCTGTGACATCAAGGACCTGCCTAAAGA
AATCACTGTTGCTACATCACGAACGCTTTCTTATTACAAATTGGGAGCTT
CGCAGCGTGTAGCAGGTGACTCAGGTTTTGCTGCATACAGTCGCTACAGG
ATTGGCAACTATAAATTAAACACAGACCATTCCAGTAGCAGTGACAATAT
TGCTTTGCTTGTACAG.
```

Example 10

The S-protein-specific CTLs were cultured with the universal DC cell vaccine targeting the coronavirus S protein as constructed in Example 9 and used for killing the target cells infected with the corresponding HLA virus, and the results showed that: the universal DC vaccine had a specific killing effect on target cells infected with the viruses of A0203, A2402, B1301, B4001, C0102, and C1502, which indicated that the different HLA molecules that can be introduced by genetic engineering means had the same function as the original A2402, could effectively stimulate the CTLs, and had a certain killing effect on the target cells. Therefore, universal DC cell vaccines suitable for more HLAs could be constructed by introducing other HLAs through a exogenous gene introduction method based on the universal DC cell vaccine.

The killing effect of the CTLs cultured with the universal DC vaccine of Example 9 on the HLA-A0203 target cells was shown in FIG. 39; the killing effect of the CTLs cultured with the universal DC vaccine of Example 9 on the HLA-A2402 target cells was shown in FIG. 40; the killing effect of the CTLs cultured with the universal DC vaccine of Example 9 on the HLA-B1301 target cells was shown in FIG. 41; the killing effect of the CTLs cultured with the universal DC vaccine of Example 9 on the HLA-B4001 target cells was shown in FIG. 42; the killing effect of the CTLs cultured with the universal DC vaccine of Example 9 on the HLA-C0102 target cells was shown in FIG. 43; and the killing effect of the CTLs cultured with the universal DC vaccine of Example 9 on the HLA-C1502 target cells was shown in FIG. 44.

Example 11

Figure 45:
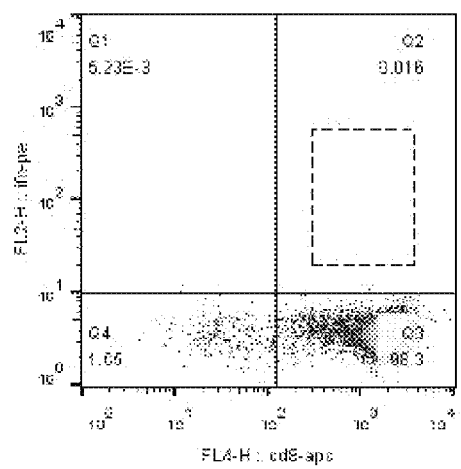
FIG. 45 shows the ratio of activated ones in cells cultured without stimulation by universal DC cells in Example 11.
Figure 46:
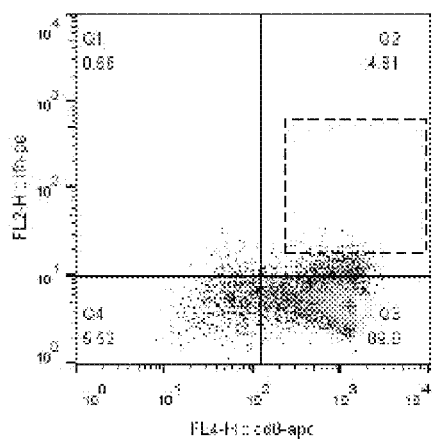
FIG. 46 shows the ratio of activated cells in CTL cells cultured with stimulation by the constructed universal DC cell vaccine against the HLA-A0203 coronavirus S protein of Example 8 in Example 11.
Figure 47:
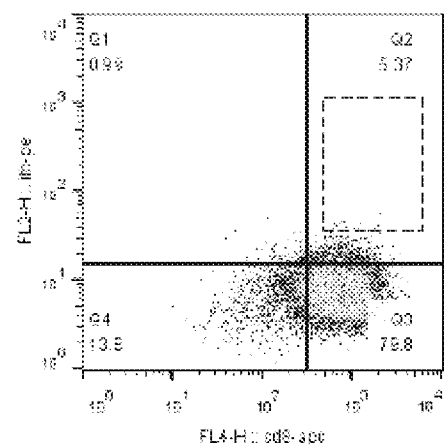
FIG. 47 shows the ratio of activated cells in CTL cells cultured with stimulation by the constructed universal DC cell vaccine against the HLA-A2402 coronavirus S protein of Example 8 in Example 11.
Figure 48:
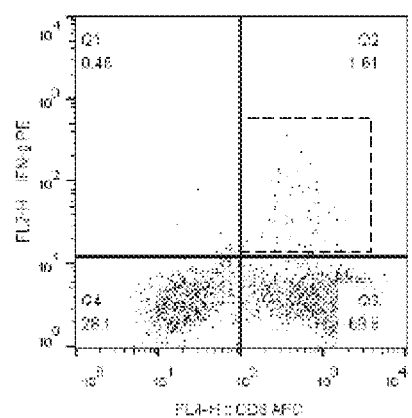
FIG. 48 shows the ratio of activated cells in CTL cells cultured with stimulation by the constructed universal DC cell vaccine against the HLA-B1301 coronavirus S protein of Example 8 in Example 11.
Figure 49:
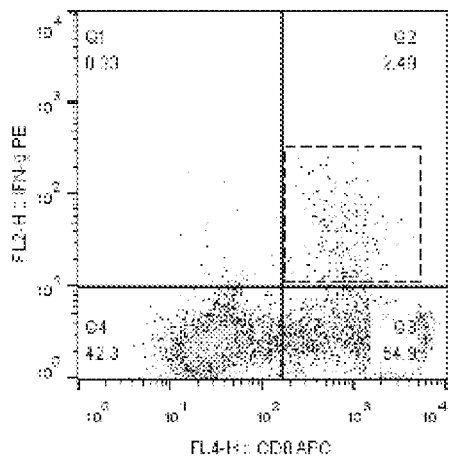
FIG. 49 shows the ratio of activated cells in CTL cells cultured with stimulation by the constructed universal DC cell vaccine against the HLA-B4001 coronavirus S protein of Example 8 in Example 11.
Figure 50:
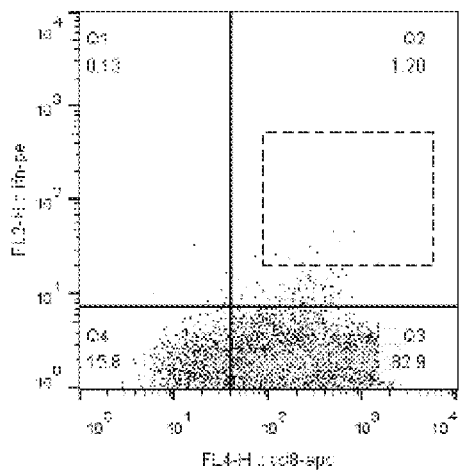
FIG. 50 shows the ratio of activated cells in CTL cells cultured with stimulation by the constructed universal DC cell vaccine against the HLA-C0102 coronavirus S protein of Example 8 in Example 11.
Figure 51:
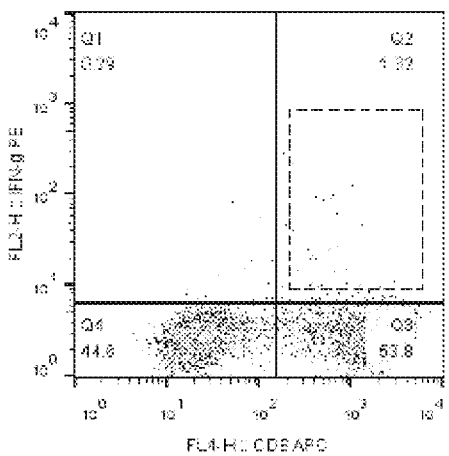
FIG. 51 shows the ratio of activated cells in CTL cells cultured with stimulation by the constructed universal DC cell vaccine against the HLA-C1502 coronavirus S protein of Example 8 in Example 11.
Figure 52:
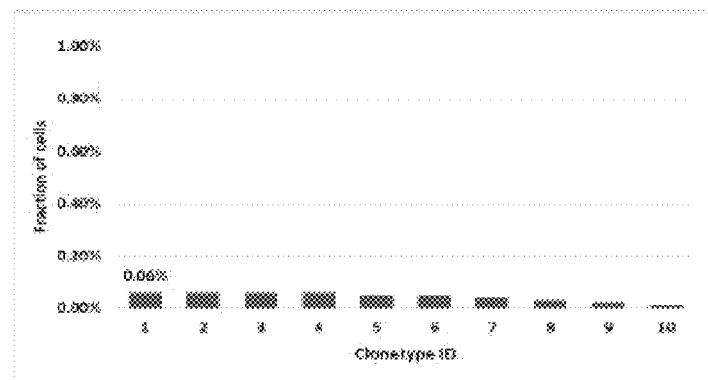
FIG. 52 shows the analysis result of TCR distribution frequency of cells cultured without universal DC cells in Example 11.
Figure 53:
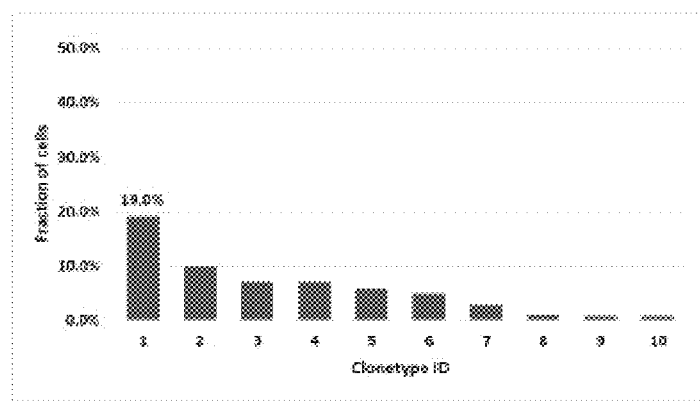
FIG. 53 shows the analysis result of TCR distribution frequency of cells cultured with stimulation by the universal DC cell vaccine against the HLA-A0203 coronavirus S protein in Example 11.
Figure 54:
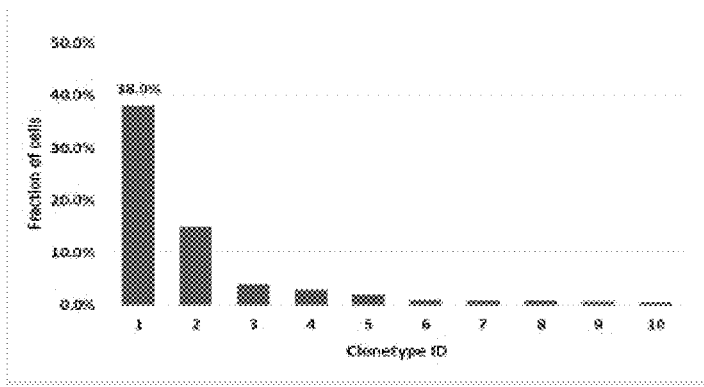
FIG. 54 shows the analysis result of TCR distribution frequency of cells cultured with stimulation by the universal DC cell vaccine against the HLA-A2402 coronavirus S protein in Example 11.
Figure 55:
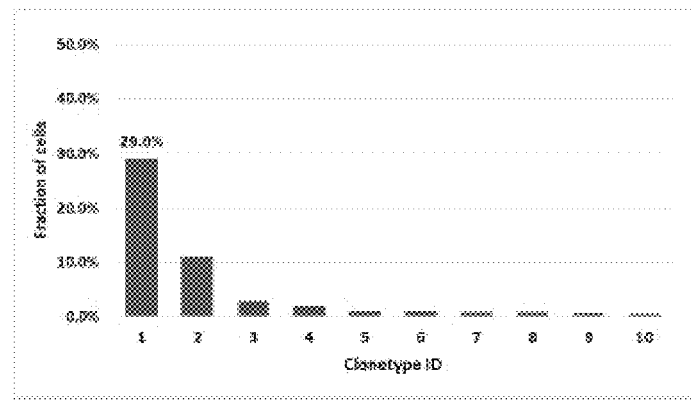
FIG. 55 shows the analysis result of TCR distribution frequency of cells cultured with stimulation by the universal DC cell vaccine against the HLA-B1301 coronavirus S protein in Example 11.
Figure 56:
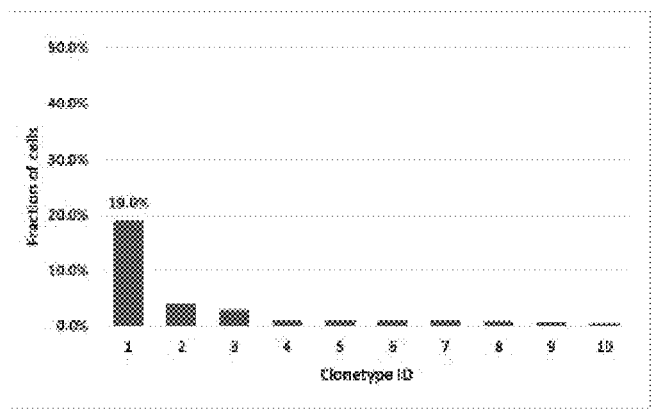
FIG. 56 shows the analysis result of TCR distribution frequency of cells cultured with stimulation by the universal DC cell vaccine against the HLA-B4001 coronavirus S protein in Example 11.
Figure 57:
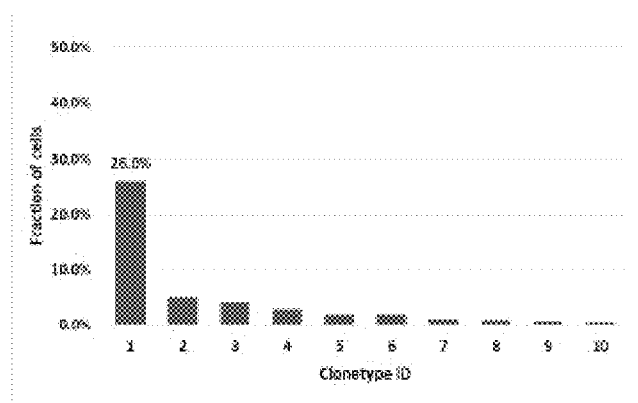
FIG. 57 shows the analysis result of TCR distribution frequency of cells cultured with stimulation by the universal DC cell vaccine against the HLA-C0102 coronavirus S protein in Example 11.
Figure 58:
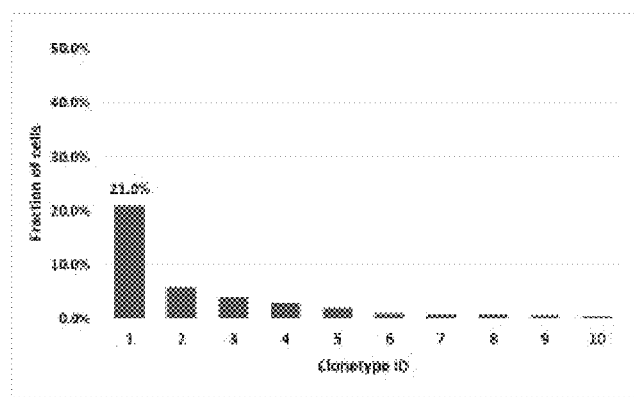
FIG. 58 shows the analysis result of TCR distribution frequency of cells cultured with stimulation by the universal DC cell vaccine against the HLA-C1502 coronavirus S protein in Example 11.

The CTLs were cultured with stimulation by the universal DC cell vaccine targeting the coronavirus S protein as constructed in Example 9, then added with the universal DC cells for secondary stimulation, and detected for the expression of CD137. The results were shown in FIGS. 45-51, wherein FIG. 45 showed the ratio of activated ones in cells cultured without stimulation by the universal DC cells, FIG. 46 showed the ratio of activated cells in the CTL cells cultured with stimulation by the constructed universal DC cell vaccine against the A0203 coronavirus S protein of Example 8, FIG. 47 showed the ratio of activated cells in the CTL cells cultured with stimulation by the constructed universal DC cell vaccine against the A2402 coronavirus S protein of Example 8, FIG. 48 showed the ratio of activated cells in the CTL cells cultured with stimulation by the constructed universal DC cell vaccine against the B1301 coronavirus S protein of Example 8, FIG. 49 showed the ratio of activated cells in the CTL cells cultured with stimulation by the constructed universal DC cell vaccine against the B4001 coronavirus S protein of Example 8, FIG. 50 showed the ratio of activated cells in the CTL cells cultured with stimulation by the constructed universal DC cell vaccine against the C0102 coronavirus S protein of Example 8, and FIG. 51 showed the ratio of activated cells in the CTL cells cultured with stimulation by the constructed universal DC cell vaccine against the C1502 coronavirus S protein of Example 8. The results showed that: among the CTL cells cultured with stimulation by the universal DC cell vaccine targeting the coronavirus S protein as constructed in Example 8, 4.81%, 5.37%, 1.61%, 2.49%, 1.2% and 1.32% of the cells were in the activated state (in the dotted box). Sequencing analysis of 10× transcriptomes and VDJ was conducted on the CTLs, and the analysis results were shown in FIGS. 52-58, wherein FIG. 52 showed the analysis result of TCR distribution frequency of cells cultured without stimulation by the universal DC cells, FIG. 53 showed the analysis result of TCR distribution frequency of cells cultured with stimulation by the universal DC cell vaccine against the A0203 targeted coronavirus S protein, FIG. 54 showed the analysis result of TCR distribution frequency of cells cultured with stimulation by the universal DC cell against A2402 of Example 8, FIG. 55 showed the analysis result of TCR distribution frequency of cells cultured with stimulation by the universal DC cell against B1301 of Example 8, FIG. 56 showed the analysis result of TCR distribution frequency of cells cultured with stimulation by the universal DC cell against B4001 of Example 8, FIG. 57 showed the analysis result of TCR distribution frequency of cells cultured with stimulation by the universal DC cell against C0102 of Example 8, and FIG. 58 showed the analysis result of TCR distribution frequency of cells cultured with stimulation by the universal DC cell against C1502 of Example 8. The results showed that: in the TCR distribution of CD137+ T cells among the CTLs cultured with stimulation by the universal DC cell vaccine targeting the coronavirus S protein as constructed in Example 9, there were 19%, 38%, 29%, 19%, 26% and 21% of high-frequency clones, compared with the cells cultured without stimulation by the universal DC cell vaccine having the highest TCR frequency of only 0.06%. Therefore, it could be proved that the universal DC vaccine could effectively stimulate specific T cells.

Example 12 Construction of Universal DC Cell Vaccine Targeting Coronavirus PLP Protein This example was the same as Example 3 except that the gene of coronavirus open reading frame protein in Example 3 was replaced with the gene encoding the coronavirus PLP protein, and the fused HLA genes were: A0301, A0101, B5502, B1502, and C0602; the nucleotide sequence of the gene of coronavirus PLP protein was as shown in SEQ ID NO.7, and was specifically:

```
ATGGAGGTGCGGACCATCAAGGTGTTCACCACAGTGGACAACATCAATCT
GCACACACAGGTGGTGGATATGTCCATGACCTACGGCCAGCAGTTTGGCC
CTACATATCTGGACGGCGCCGATGTGACCAAGATCAAGCCACACAACTCT
CACGAGGGCAAGACATTCTACGTGCTGCCCAATGACGATACCCTGAGGGT
GGAGGCCTTCGAGTACTATCACACCACAGACCCATCCTTTCTGGGCCGCT
ACATGTCTGCCCTGAACCACACAAAGAAGTGGAAGTATCCCCAAGTGAAT
GGCCTGACCTCTATCAAGTGGGCCGACAACAATTGCTACCTGGCCACAGC
CCTGCTGACCCTGCAGCAGATCGAGCTGAAGTTCAACCCCCCTGCCCTGC
AGGATGCATACTATAGGGCAAGAGCAGGAGAGGCAGCAAACTTTTGCGCA
CTGATCCTGGCCTACTGTAATAAGACAGTGGGAGAGCTGGGCGACGTGCG
GGAGACCATGAGCTATCTGTTCCAGCACGCCAACCTGGATTCCTGTAAGA
GGGTGCTGAATGTGGTGTGCAAGACATGTGGCCAGCAGCAGACCACACTG
AAGGGCGTGGAGGCCGTGATGTACATGGGCACCCTGAGCTATGAGCAGTT
TAAGAAGGGCGTGCAGATCCCTTGCACATGTGGCAAGCAGGCCACCAAGT
ACCTGGTGCAGCAGGAGTCTCCATTCGTGATGATGAGCGCCCCACCCGCC
CAGTATGAGCTGAAGCACGGCACCTTCACCTGCGCCTCTGAGTACACCGG
CAACTATCAGTGTGGCCACTACAAGCACATCACAAGCAAGGAGACCCTGT
ATTGCATCGACGGCGCCCTGCTGACAAAGAGCTCCGAGTACAAGGGCCCC
ATCACCGACGTGTTCTACAAGGAGAACAGCTATACCACAACCATCAAGCC
TGTGACC.
```

Example 13

The PLP-specific CTLs were cultured with the universal DC cell vaccine targeting the coronavirus PLP protein as constructed in Example 12 and used for killing the target cells that were of the corresponding HLA type and express an N antigen, and the results showed that: the universal DC cell vaccine targeting the coronavirus PLP protein had a specific killing effect on A0301, A0101, B5502, B1502, C0303 and C0602 target cells expressing the coronavirus N antigen, which indicated that the different molecules that can be introduced by genetic engineering means had the same function as the original C0303, could effectively stimulate the CTLs, and had a certain killing effect on the target cells. Therefore, universal DC cell vaccines suitable for more HLAs could be constructed by introducing other HLAs through a exogenous gene introduction method based on the universal DC cell vaccine.

Figure 59:
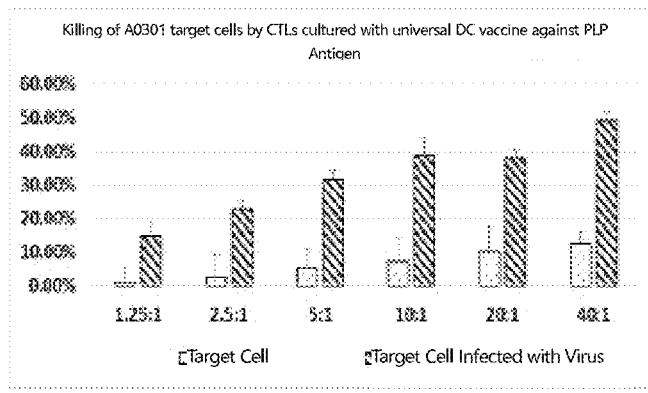
FIG. 59 shows the killing effect of CTLs cultured with the universal DC vaccine of Example 12 on HLA-A0301 target cells in Example 13.
Figure 60:
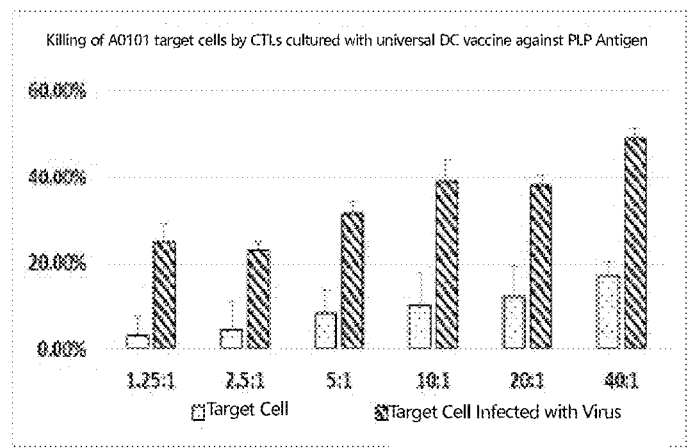
FIG. 60 shows the killing effect of CTLs cultured with the universal DC vaccine of Example 12 on HLA-A0101 target cells in Example 13.
Figure 61:
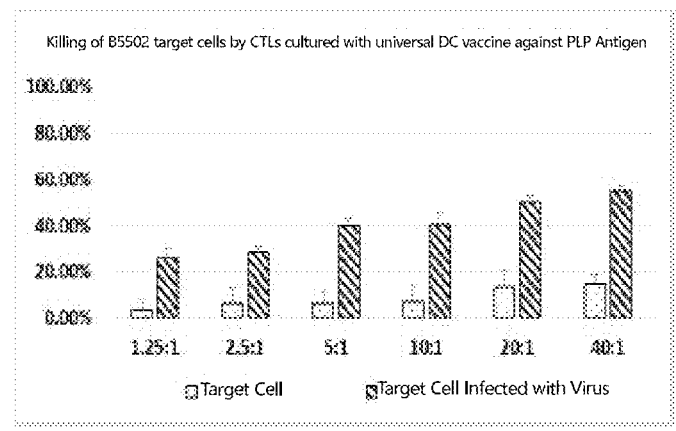
FIG. 61 shows the killing effect of CTLs cultured with the universal DC vaccine of Example 12 on HLA-B5502 target cells in Example 13.
Figure 62:
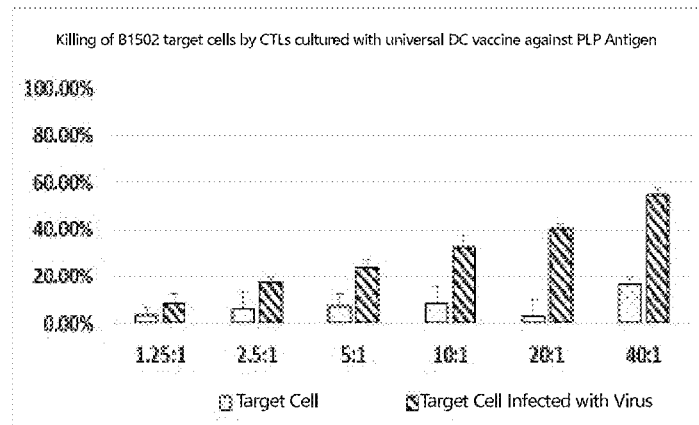
FIG. 62 shows the killing effect of CTLs cultured with the universal DC vaccine of Example 12 on HLA-B1502 target cells in Example 13.
Figure 63:
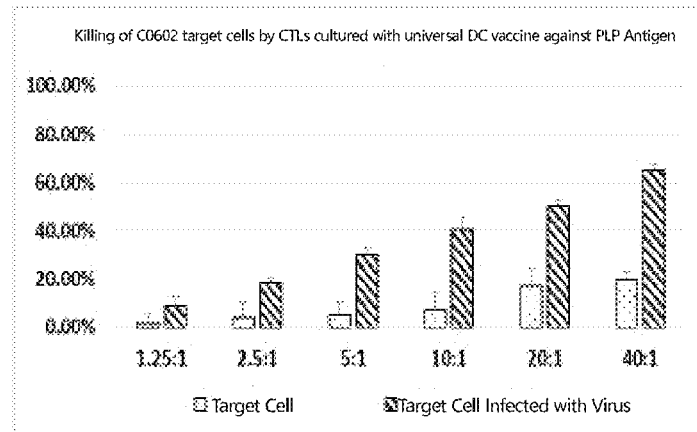
FIG. 63 shows the killing effect of CTLs cultured with the universal DC vaccine of Example 12 on HLA-C0602 target cells in Example 13.
Figure 64:
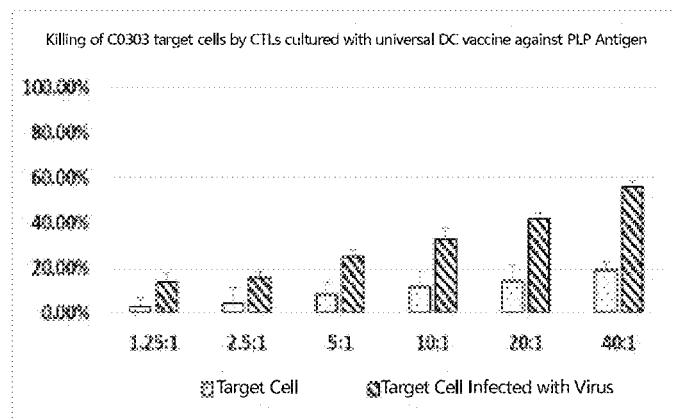
FIG. 64 shows the killing effect of CTLs cultured with the universal DC vaccine of Example 12 on HLA-C0303 target cells in Example 13.

The killing effect of the CTLs cultured with the universal DC vaccine of Example 12 on the HLA-A0301 target cells was shown in FIG. 59; the killing effect of the CTLs cultured with the universal DC vaccine of Example 12 on the HLA-A0101 target cells was shown in FIG. 60; the killing effect of the CTLs cultured with the universal DC vaccine of Example 12 on the HLA-B5502 target cells was shown in FIG. 61; the killing effect of the CTLs cultured with the universal DC vaccine of Example 12 on the HLA-B1502 target cells was shown in FIG. 62; the killing effect of the CTLs cultured with the universal DC vaccine of Example 12 on the HLA-C0602 target cells was shown in FIG. 63; and the killing effect of the CTLs cultured with the universal DC vaccine of Example 12 on the HLA-C0303 target cells was shown in FIG. 64.

Example 14

Figure 65:
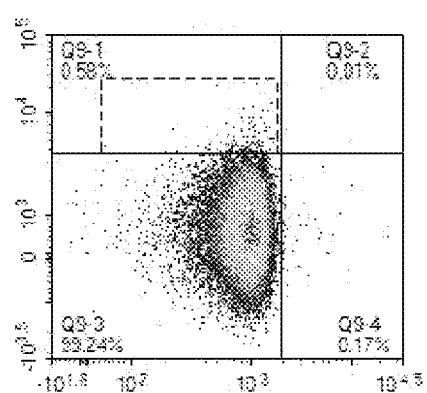
FIG. 65 shows the ratio of activated ones in cells cultured without stimulation by universal DC cells in Example 14.
Figure 66:
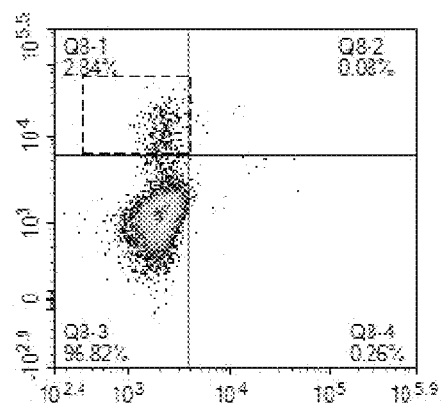
FIG. 66 shows the ratio of activated cells in CTLs cultured with stimulation by the universal DC cell vaccine against the HLA-A0301 coronavirus PLP protein in Example 14.
Figure 67:
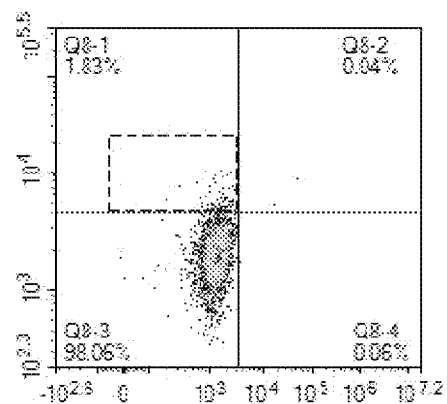
FIG. 67 shows the ratio of activated cells in CTLs cultured with stimulation by the universal DC cell vaccine against the HLA-A0101 coronavirus PLP protein in Example 14.
Figure 68:
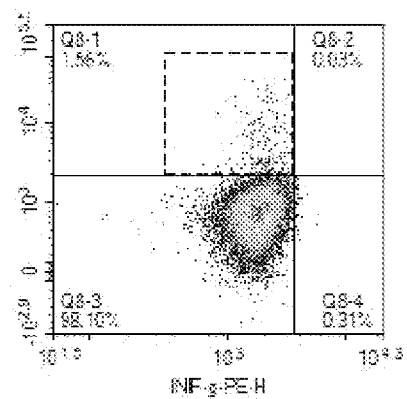
FIG. 68 shows the ratio of activated cells in CTLs cultured with stimulation by the universal DC cell vaccine against the HLA-B5502 coronavirus PLP protein in Example 14.
Figure 69:
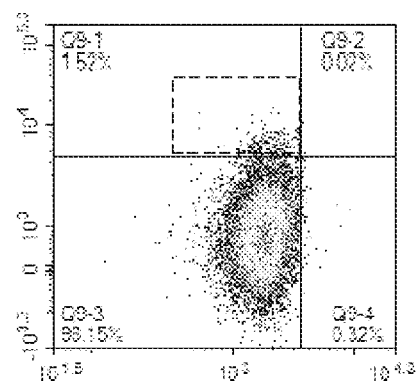
FIG. 69 shows the ratio of activated cells in CTLs cultured with stimulation by the universal DC cell vaccine against the HLA-B1502 coronavirus PLP protein in Example 14.
Figure 70:
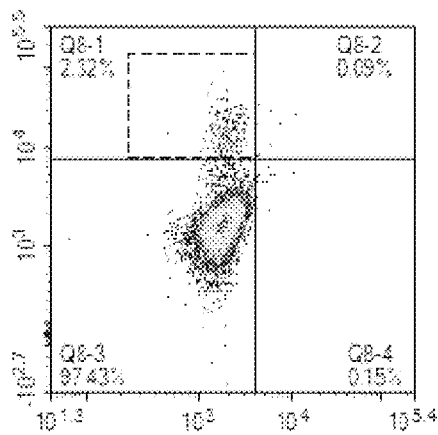
FIG. 70 shows the ratio of activated cells in CTLs cultured with stimulation by the universal DC cell vaccine against the HLA-C0602 coronavirus PLP protein in Example 14.
Figure 71:
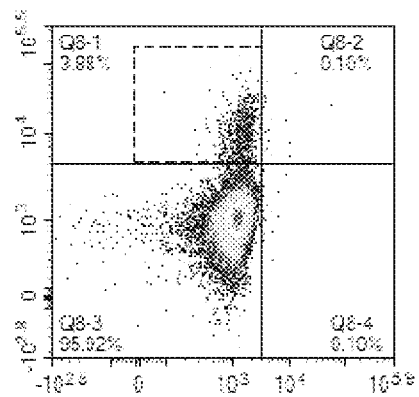
FIG. 71 shows the ratio of activated cells in CTLs cultured with stimulation by the universal DC cell vaccine against the HLA-C0303 PLP protein in Example 14.
Figure 72:
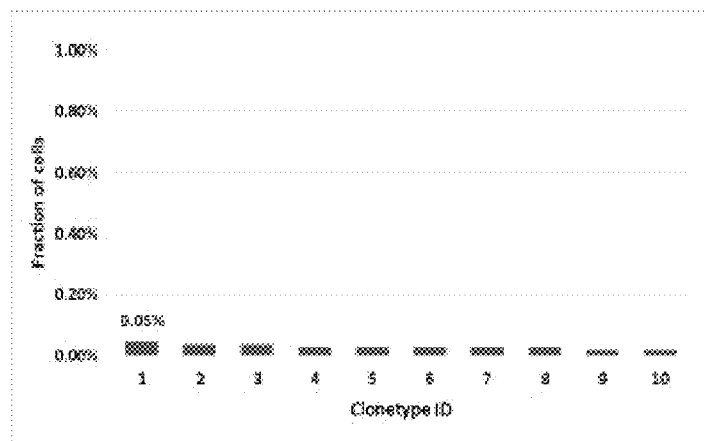
FIG. 72 shows the analysis result of TCR distribution frequency of cells cultured without stimulation by universal DC cells in Example 14.
Figure 73:
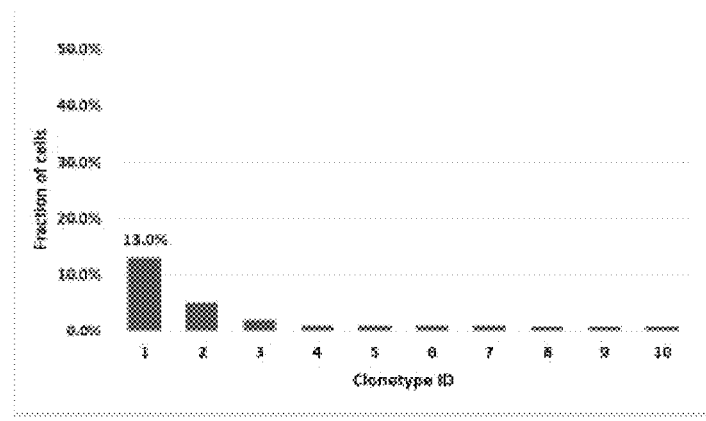
FIG. 73 shows the analysis result of TCR distribution frequency of CTLs cultured with stimulation by the universal DC cell vaccine against the HLA-A0301 coronavirus PLP protein in Example 14.
Figure 74:
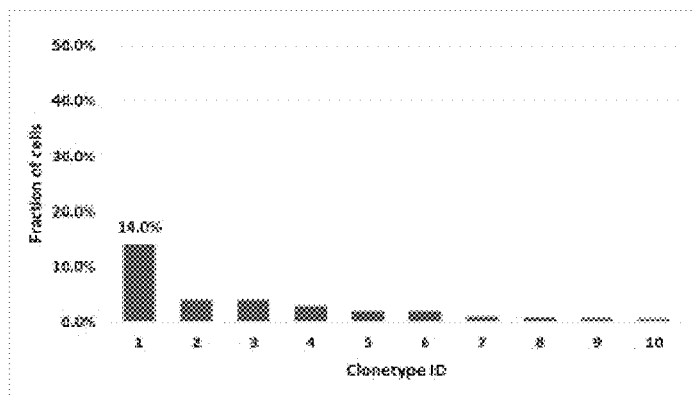
FIG. 74 shows the analysis result of TCR distribution frequency of CTLs cultured with stimulation by the universal DC cell vaccine against the HLA-A0101 coronavirus PLP protein in Example 14.
Figure 75:
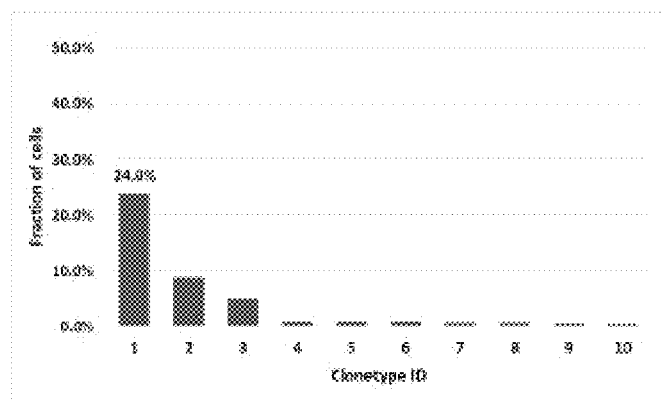
FIG. 75 shows the analysis result of TCR distribution frequency of CTLs cultured with stimulation by the universal DC cell vaccine against the HLA-B5502 coronavirus PLP protein in Example 14.
Figure 76:
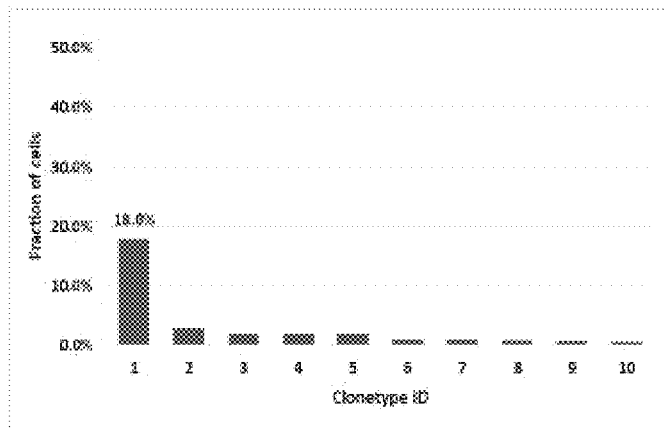
FIG. 76 shows the analysis result of TCR distribution frequency of CTLs cultured with stimulation by the universal DC cell vaccine against the HLA-B1502 coronavirus PLP protein in Example 14.
Figure 77:
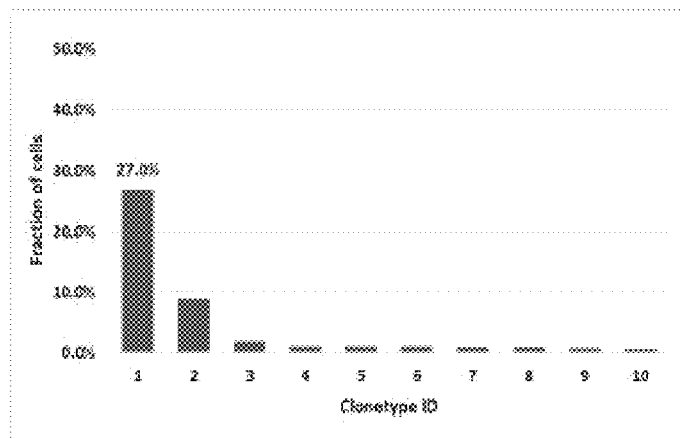
FIG. 77 shows the analysis result of TCR distribution frequency of CTLs cultured with stimulation by the universal DC cell vaccine against the HLA-C0602 coronavirus PLP protein in Example 14.
Figure 78:
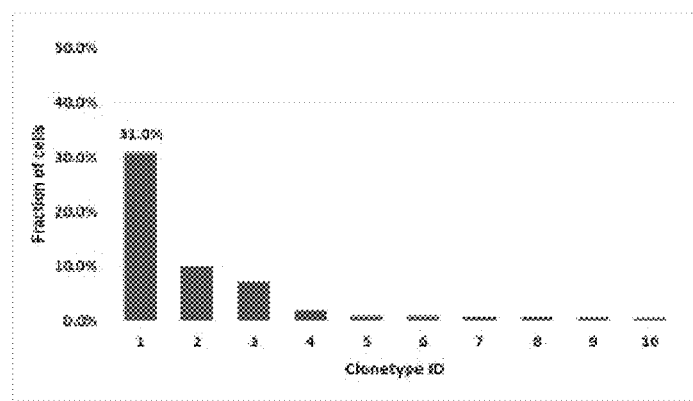
FIG. 78 shows the analysis result of TCR distribution frequency of CTLs cultured with stimulation by the universal DC cell vaccine against the HLA-C0303 coronavirus PLP protein in Example 14.

The CTLs were cultured with stimulation by the universal DC cell vaccine targeting the coronavirus PLP protein as constructed in Example 12, then added with the universal DC cell vaccine targeting the coronavirus PLP protein for secondary stimulation, and detected for the expression of CD137. The results were shown in FIGS. 65-71, wherein FIG. 65 showed the ratio of activated ones in cells cultured without stimulation by the universal DC cells, FIG. 66 showed the ratio of activated cells in the CTLs cultured with stimulation by the universal DC cell vaccine targeting the A0301 coronavirus PLP protein of Example 12, FIG. 67 showed the ratio of activated cells in CTLs cultured with stimulation by the universal DC cell against A0101 of Example 12, FIG. 68 showed the ratio of activated cells in CTLs cultured with stimulation by the universal DC cell against B5502 of Example 12, FIG. 69 showed the ratio of activated cells in CTLs cultured with stimulation by the universal DC cell against B1502 of Example 12, FIG. 70 showed the ratio of activated cells in CTLs cultured with stimulation by the universal DC cell against C0602 of Example 12, and FIG. 71 showed the ratio of activated cells in CTLs cultured with stimulation by the universal DC cell against C0303 of Example 12. The results showed that: among the CTLs cultured with stimulation by the universal DC cell vaccine targeting the coronavirus PLP protein, 2.84%, 1.83%, 1.56%, 1.52%, 2.32%, and 3.88% of the cells were in the activated state (in the dotted box). Sequencing analysis of 10xtranscriptomes and VDJ was conducted on the CTLs, and the results were shown in FIGS. 72-78, wherein FIG. 72 showed the analysis result of TCR distribution frequency of cells cultured without stimulation by the universal DC cells, FIG. 73 showed the analysis result of TCR distribution frequency of CTLs cultured with stimulation by the universal DC cell vaccine targeting the A0301 coronavirus PLP protein of Example 12, FIG. 74 showed the analysis result of TCR distribution frequency of CTL cells cultured with stimulation by the universal DC cells against A0101 of Example 12, FIG. 75 showed the analysis result of TCR distribution frequency of CTL cells cultured with stimulation by the universal DC cells against B5502 of Example 12, FIG. 76 showed the analysis result of TCR distribution frequency of CTL cells cultured with stimula- tion by the universal DC cells against B1502 of Example 12, FIG. 77 showed the analysis result of TCR distribution frequency of CTL cells cultured with stimulation by the universal DC cells against C0602 of Example 12, and FIG. 78 showed the analysis result of TCR distribution frequency of CTL cells cultured with stimulation by the universal DC cells against C0303 of Example 12. The results showed that: in the TCR distribution of CD137+ T cells among the CTLs cultured with stimulation by the universal DC cell vaccine targeting the coronavirus PLP protein, there were 13%, 14%, 24%, 18%, 27%, and 31% of high-frequency clones, com- pared with the cells cultured without stimulation by the universal DC cell vaccine having the highest TCR frequency of only 0.05%. Therefore, it could be proved that the universal DC vaccine could effectively stimulate specific T cells.

Example 15 Construction of Universal DC Cell Vaccine Targeting Coronavirus M Protein This example was the same as Example 3 except that the gene of coronavirus open reading frame protein in Example 3 was replaced with the gene encoding the coronavirus M protein, and the fused HLAs were: C0702, C0302, B3501, B5801, and B1302; the nucleotide sequence of the gene of coronavirus M protein was as shown in SEQ ID NO.8, and was specifically:

```
ATGGCAGATTCCAACGGTACTATTACCGTTGAAGAGCTTAAAAAGCTCCT
TGAACAATGGAACCTAGTAATAGGTTTCCTATTCCTTACATGGATTTGTC
TTCTACAATTTGCCTATGCCAACAGGAATAGGTTTTTGTATATAATTAAG
TTAATTTTCCTCTGGCTGTTATGGCCAGTAACTTTAGCTTGTTTTGTGCT
TGCTGCTGTTTACAGAATAAATTGGATCACCGGTGGAATTGCTATCGCAA
TGGCTTGTCTTGTAGGCTTGATGTGGCTCAGCTACTTCATTGCTTCTTTC
AGACTGTTTGCGCGTACGCGTTCCATGTGGTCATTCAATCCAGAAACTAA
CATTCTTCTCAACGTGCCACTCCATGGCACTATTCTGACCAGACCGCTTC
TAGAAAGTGAACTCGTAATCGGAGCTGTGATCCTTCGTGGACATCTTCGT
ATTGCTGGACACCATCTAGGACGCTGTGACATCAAGGACCTGCCTAAAGA
AATCACTGTTGCTACATCACGAACGCTTTCTTATTACAAATTGGGAGCTT
CGCAGCGTGTAGCAGGTGACTCAGGTTTTGCTGCATACAGTCGCTACAGG
ATTGGCAACTATAAATTAAACACAGACCATTCCAGTAGCAGTGACAATAT
TGCTTTGCTTGTACAG.
```

Example 16

The M-protein-specific CTLs were cultured with the universal DC cell vaccine targeting the coronavirus M protein as constructed in Example 15 and used for killing the target cells that were of the corresponding HLA type and express an N antigen, and the results showed that: the universal DC cell vaccine targeting the coronavirus M protein had a specific killing effect on target cells infected with the viruses of C0702, C0302, B3501, B5801, B1302, and B1511, which indicated that the different HLA mol- ecules that can be introduced by genetic engineering means had the same function as the original B1511, could effec- tively stimulate the CTLs, and had a certain killing effect on the target cells. Therefore, universal DC cell vaccines suitable for more HLAs could be constructed by introducing other HLAs through a exogenous gene introduction method based on the universal DC cell vaccine.

Figure 79:
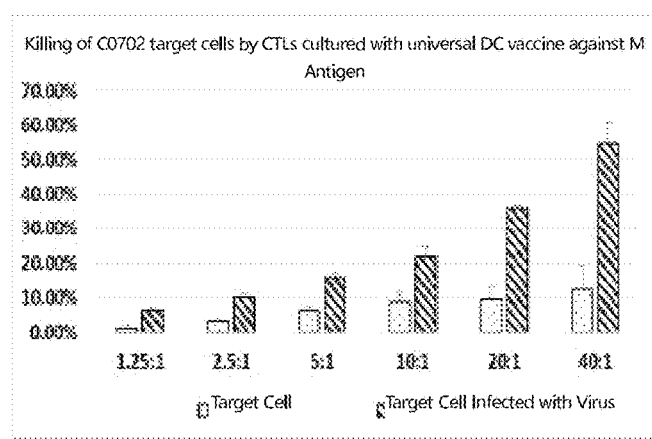
FIG. 79 shows the killing effect of CTLs cultured with the universal DC vaccine of Example on HLA-C0702 target cells in Example 16.
Figure 80:
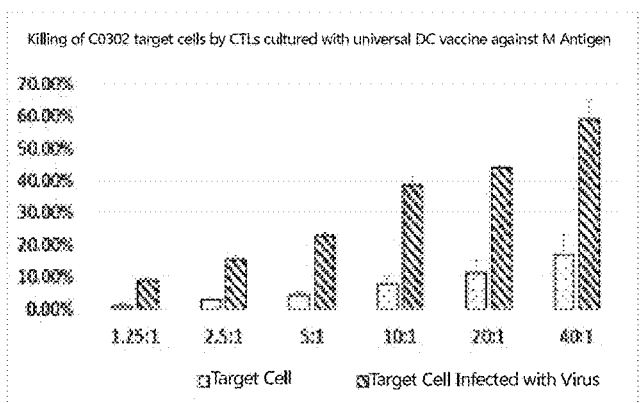
FIG. 80 shows the killing effect of CTLs cultured with the universal DC vaccine of Example on HLA-C0302 target cells in Example 16.
Figure 81:
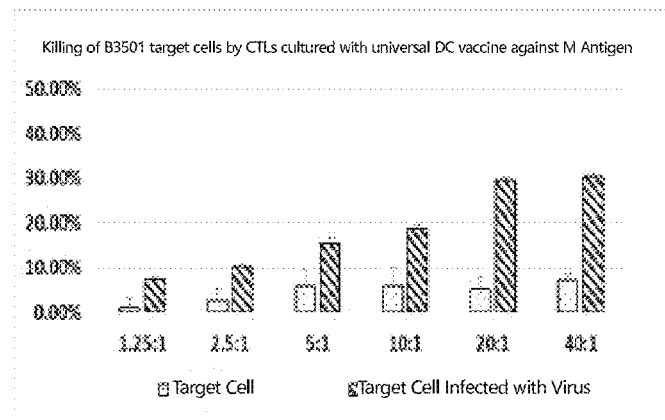
FIG. 81 shows the killing effect of CTLs cultured with the universal DC vaccine of Example on HLA-B3501 target cells in Example 16.
Figure 82:
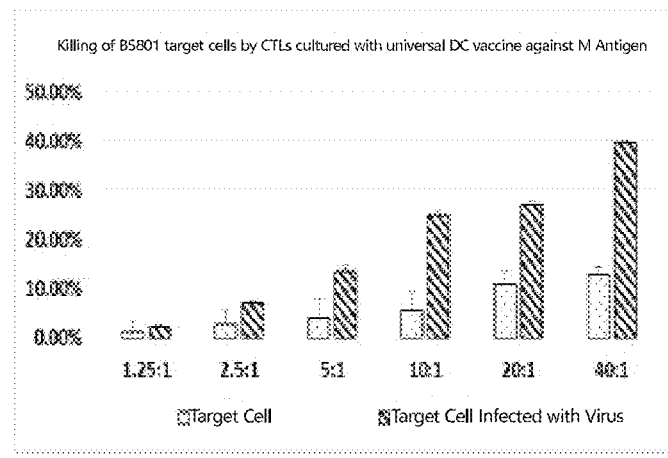
FIG. 82 shows the killing effect of CTLs cultured with the universal DC vaccine of Example on HLA-B5801 target cells in Example 16.
Figure 83:
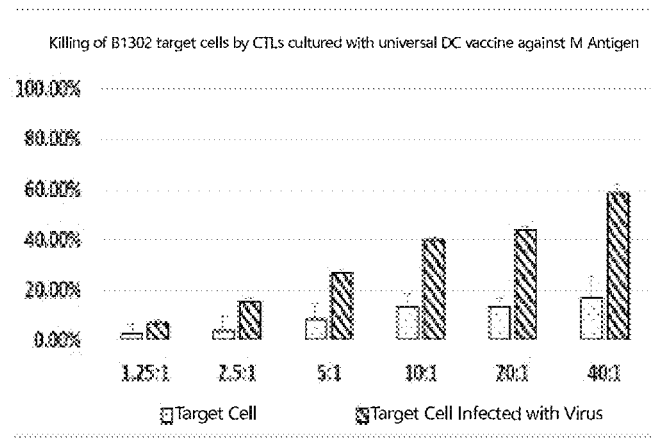
FIG. 83 is a diagram showing the killing effect of CTLs cultured with the universal DC vaccine of Example 15 on HLA-B1302 target cells in Example 16.
Figure 84:
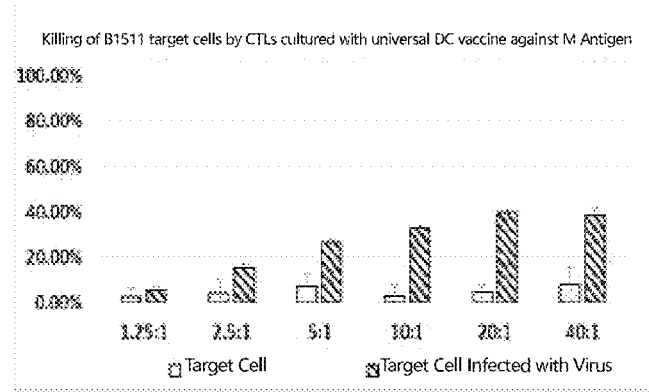
FIG. 84 shows the killing effect of CTLs cultured with the universal DC vaccine of Example on HLA-B1511 target cells in Example 16.

The killing effect of the CTLs cultured with the universal DC vaccine of Example 15 on the HLA-C0702 target cells was shown in FIG. 79; the killing effect of the CTLs cultured with the universal DC vaccine of Example 15 on the HLA-C0302 target cells was shown in FIG. 80; the killing effect of the CTLs cultured with the universal DC vaccine of Example 15 on the HLA-B3501 target cells was shown in FIG. 81; the killing effect of the CTLs cultured with the universal DC vaccine of Example 15 on the HLA-B5801 target cells was shown in FIG. 82; the killing effect of the CTLs cultured with the universal DC vaccine of Example 15 on the HLA-B1302 target cells was shown in FIG. 83; and the killing effect of the CTLs cultured with the universal DC vaccine of Example 15 on the HLA-B1511 target cells was shown in FIG. 84.

Example 17

Figure 85:
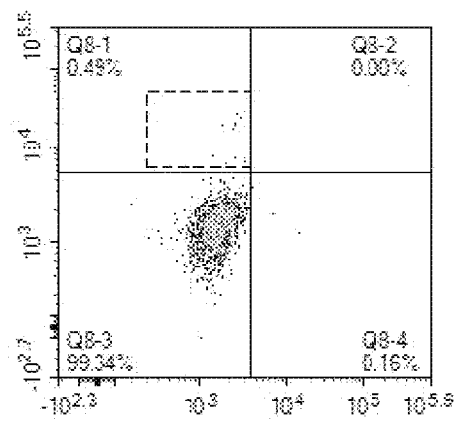
FIG. 85 shows the ratio of activated ones in cells cultured without stimulation by universal DC cells in Example 17.
Figure 86:
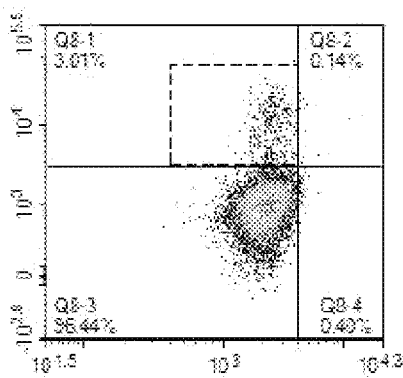
FIG. 86 shows the ratio of activated cells in CTLs cultured with stimulation by the universal DC cell vaccine against the HLA-C0702 targeted coronavirus M protein in Example 17.
Figure 87:
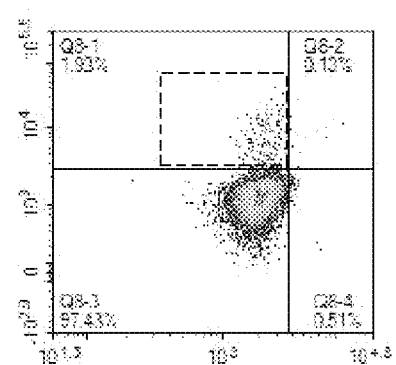
FIG. 87 shows the ratio of activated cells in CTLs cultured with stimulation by the universal DC cell vaccine against the HLA-C0302 targeted coronavirus M protein in Example 17.
Figure 88:
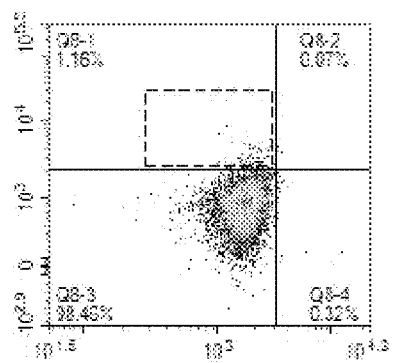
FIG. 88 shows the ratio of activated cells in CTLs cultured with stimulation by the universal DC cell vaccine against the HLA-B3501 targeted coronavirus M protein in Example 17.
Figure 89:
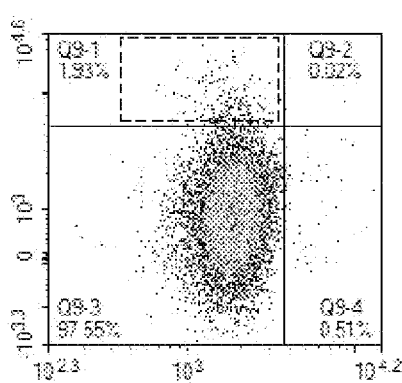
FIG. 89 shows the ratio of activated cells in CTLs cultured with stimulation by the universal DC cell vaccine against the HLA-B5801 targeted coronavirus M protein in Example 17.
Figure 90:
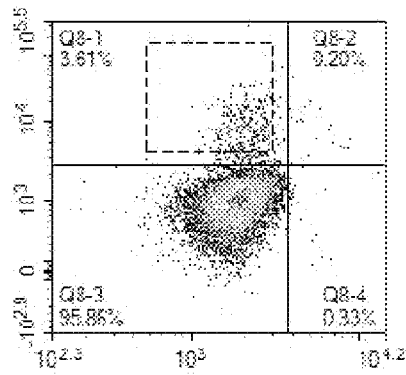
FIG. 90 shows the ratio of activated cells in CTLs cultured with stimulation by the universal DC cell vaccine against the HLA-B1302 targeted coronavirus M protein in Example 17.
Figure 91:
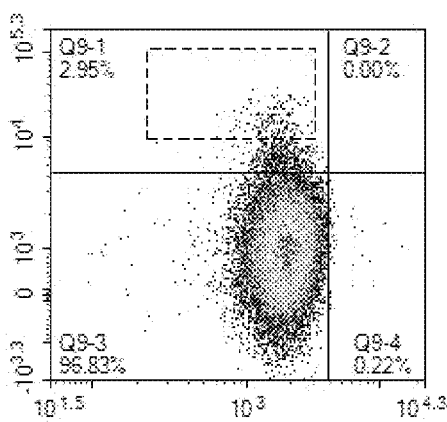
FIG. 91 shows the ratio of activated cells in CTLs cultured with stimulation by the universal DC cell vaccine against the HLA-B1511 targeted coronavirus M protein in Example 17.
Figure 92:
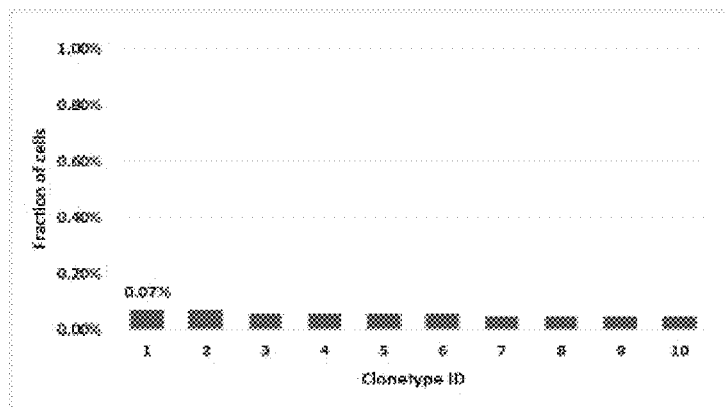
FIG. 92 shows the analysis result of TCR distribution frequency of cells cultured without stimulation by universal DC cells in Example 17.
Figure 93:
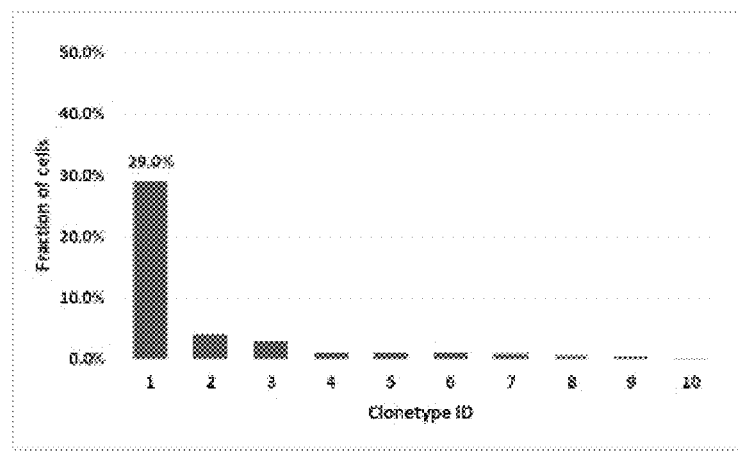
FIG. 93 shows the analysis result of TCR distribution frequency of CTLs cultured with stimulation by the universal DC cell vaccine against the HLA-C0702 targeted coronavirus M protein in Example 17.
Figure 94:
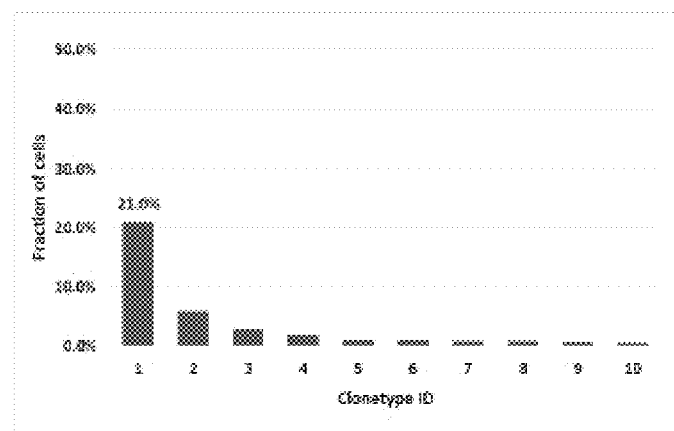
FIG. 94 shows the analysis result of TCR distribution frequency of CTLs cultured with stimulation by the universal DC cell vaccine against the HLA-C0302 targeted coronavirus M protein in Example 17.
Figure 95:
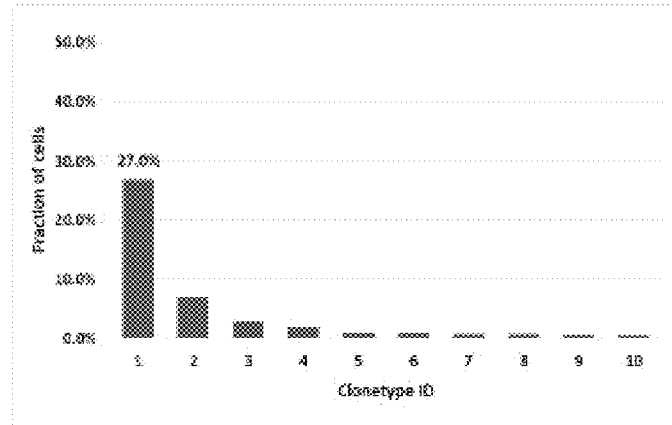
FIG. 95 shows the analysis result of TCR distribution frequency of CTLs cultured with stimulation by the universal DC cell vaccine against the HLA-B3501 targeted coronavirus M protein in Example 17.
Figure 96:
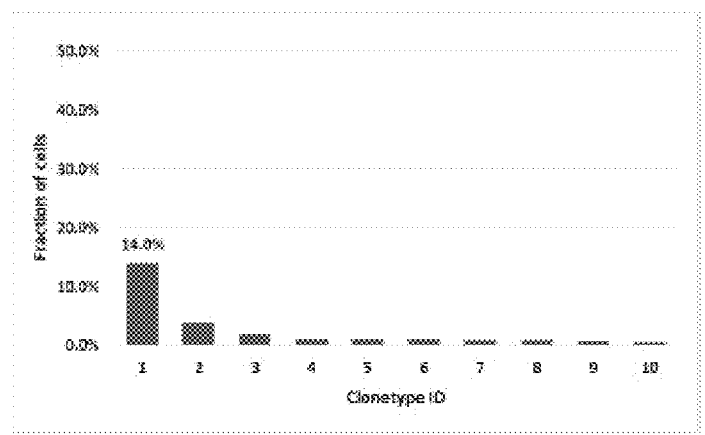
FIG. 96 shows the analysis result of TCR distribution frequency of CTLs cultured with stimulation by the universal DC cell vaccine against the HLA-B5801 targeted coronavirus M protein in Example 17.
Figure 97:
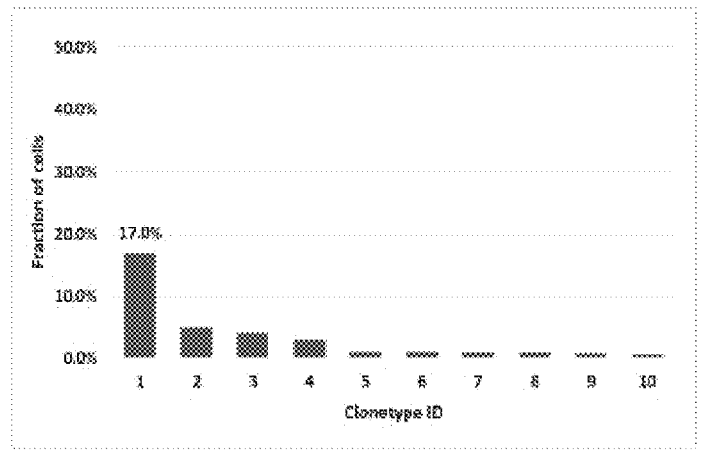
FIG. 97 shows the analysis result of TCR distribution frequency of CTLs cultured with stimulation by the universal DC cell vaccine against the HLA-B1302 targeted coronavirus M protein in Example 17.
Figure 98:
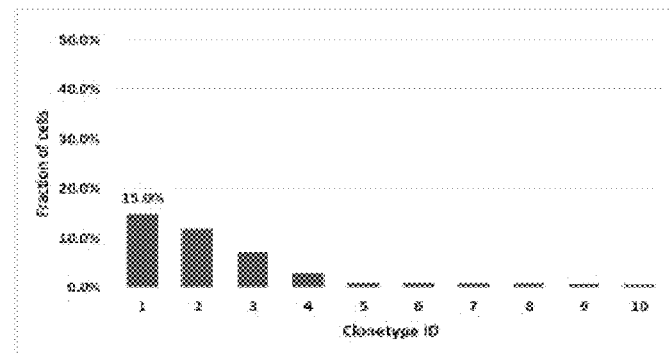
FIG. 98 shows the analysis result of TCR distribution frequency of CTLs cultured with stimulation by the universal DC cell vaccine against the HLA-B1511 targeted coronavirus M protein in Example 17.

The CTLs were cultured with stimulation by the universal DC cell vaccine targeting the coronavirus M protein as constructed in Example 15, then added with the universal DC cells for secondary stimulation, and detected for the expression of CD137. The results were shown in FIGS. 85-91, wherein FIG. 85 showed the ratio of activated ones in cells cultured without stimulation by the universal DC cells, FIG. 86 showed the ratio of activated cells in the CTLs cultured with stimulation by the universal DC cell vaccine targeting the HLA-C0702 coronavirus M protein, FIG. 87 showed the ratio of activated cells in the CTLs cultured with stimulation by the universal DC cells against C0302 of Example 15, FIG. 88 showed the ratio of activated cells in the CTLs cultured with stimulation by the universal DC cells against B3501 of Example 15, FIG. 89 showed the ratio of activated cells in the CTLs cultured with stimulation by the universal DC cells against B5801 of Example 15, FIG. 90 showed the ratio of activated cells in the CTLs cultured with stimulation by the universal DC cells against B1302 of Example 15, and FIG. 91 showed the ratio of activated cells in the CTLs cultured with stimulation by the universal DC cells against B1511 of Example 15. The results showed that: among the CTLs cultured with stimulation by the universal DC cell vaccine targeting the coronavirus M protein, 3.01%, 1.93%, 1.16%, 1.93%, 3.61% and 2.95% of the cells were in the activated state (in the dotted box). Sequencing analysis of 10× transcriptomes and VDJ was conducted on the CTLs, and the results were shown in FIGS. 92-98, wherein FIG. 92 showed the analysis result of TCR distribution frequency of cells cultured without stimulation by the universal DC cells, FIG. 93 showed the analysis result of TCR distribution frequency of CTL cells cultured with stimulation by the universal DC cell vaccine targeting the C0702 coronavirus M protein, FIG. 94 showed the analysis result of TCR distribution frequency of CTL cells cultured with stimulation by the universal DC cell against C0302 of Example 15, FIG. 95 showed the analysis result of TCR distribution frequency of CTL cells cultured with stimulation by the universal DC cell against B3501 of Example 15, FIG. 96 showed the analysis result of TCR distribution frequency of CTL cells cultured with stimulation by the universal DC cell against B5801 of Example 15, FIG. 97 showed the analysis result of TCR distribution frequency of CTL cells cultured with stimulation by the universal DC cell against B1302 of Example 15, and FIG. 98 showed the analysis result of TCR distribution frequency of CTL cells cultured with stimulation by the universal DC cell against B1511 of Example 15. The results showed that: in the TCR distribution of CD137+ T cells among the CTLs cultured with stimulation by the universal DC cell vaccine targeting the coronavirus M protein, there were 29%, 21%, 27%, 14%, 17%, and 15% of high-frequency clones, compared with the cells cultured without stimulation by the universal DC cell vaccine having the highest TCR frequency of only 0.07%. Therefore, it could be proved that the universal DC vaccine could effectively stimulate specific T cells.

Example 18 Construction of Universal DC Cell Vaccine Targeting Coronavirus N Protein This example was the same as Example 3 except that the gene of coronavirus open reading frame protein in Example 3 was replaced with the gene encoding the coronavirus N protein; and the nucleotide sequence of the gene of coronavirus N protein was as shown in SEQ ID NO.9, and was specifically:

```
ATGTCTGATAATGGACCCCAAAATCAGCGAAATGCACCCCGCATTACGTT
TGGTGGACCCTCAGATTCAACTGGCAGTAACCAGAATGGAGAACGCAGTG
GGGCGCGATCAAAACAACGTCGGCCCCAAGGTTTACCCAATAATACTGCG
TCTTGGTTCACCGCTCTCACTCAACATGGCAAGGAAGACCTTAAATTCCC
TCGAGGACAAGGCGTTCCAATTAACACCAATAGCAGTCCAGATGACCAAA
TTGGCTACTACCGAAGAGCTACCAGACGAATTCGTGGTGGTGACGGTAAA
ATGAAAGATCTCAGTCCAAGATGGTATTTCTACTACCTAGGAACTGGGCC
AGAAGCTGGACTTCCCTATGGTGCTAACAAAGACGGCATCATATGGGTTG
CAACTGAGGGAGCCTTGAATACACCAAAAGATCACATTGGCACCCGCAAT
CCTGCTAACAATGCTGCAATCGTGCTACAACTTCCTCAAGGAACAACATT
GCCAAAAGGCTTCTACGCAGAAGGGAGCAGAGGCGGCAGTCAAGCCTCTT
CTCGTTCCTCATCACGTAGTCGCAACAGTTCAAGAAATTCAACTCCAGGC
AGCAGTAGGGGAACTTCTCCTGCTAGAATGGCTGGCAATGGCGGTGATGC
TGCTCTTGCTTTGCTGCTGCTTGACAGATTGAACCAGCTTGAGAGCAAAA
TGTCTGGTAAAGGCCAACAACAACAAGGCCAAACTGTCACTAAGAAATCT
GCTGCTGAGGCTTCTAAGAAGCCTCGGCAAAAACGTACTGCCACTAAAGC
ATACAATGTAACACAAGCTTTCGGCAGACGTGGTCCAGAACAAACCCAAG
GAAATTTTGGGGACCAGGAACTAATCAGACAAGGAACTGATTACAAACAT
TGGCCGCAAATTGCACAATTTGCCCCCAGCGCTTCAGCGTTCTTCGGAAT
GTCGCGCATTGGCATGGAAGTCACACCTTCGGGAACGTGGTTGACCTACA
CAGGTGCCATCAAATTGGATGACAAAGATCCAAATTTCAAAGATCAAGTC
ATTTTGCTGAATAAGCATATTGACGCATACAAAACATTCCCACCAACAGA
GCCTAAAAAGGACAAAAAGAAGAAGGCTGATGAAACTCAAGCCTTACCGC
AGAGACAGAAGAAACAGCAAACTGTGACTCTTCTTCCTGCTGCAGATTTG
GATGATTTCTCCAAACAATTGCAACAATCCATGAGCAGTGCTGACTCAAC
TCAGGCC.
```

Example 19

The N-protein-specific CTLs were cultured with the universal DC cell vaccine targeting the coronavirus N protein as constructed in Example 18 and used for killing the target cells that were of the corresponding HLA type and express an N antigen. The results were shown in FIGS. 99-105, and the results showed that: the universal DC vaccine had a specific killing effect on A0206, A2601, B1505, C1402, C1202, and C1203 target cells expressing the coronavirus N antigen, which indicated that the different HLA molecules that can be introduced by genetic engineering means had the same function as the original B1505, could effectively stimulate the CTLs, and had a certain killing effect on the target cells. Therefore, universal DC cell vaccines suitable for more HLAs could be constructed by introducing other HLAs through a exogenous gene introduction method based on the universal DC cell vaccine.

Figure 99:
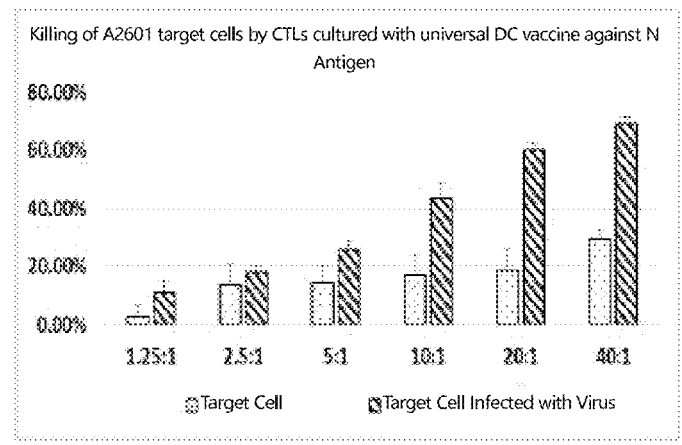
FIG. 99 shows the killing effect of CTLs cultured with the universal DC vaccine of Example 18 on HLA-A2601 target cells in Example 19.
Figure 100:
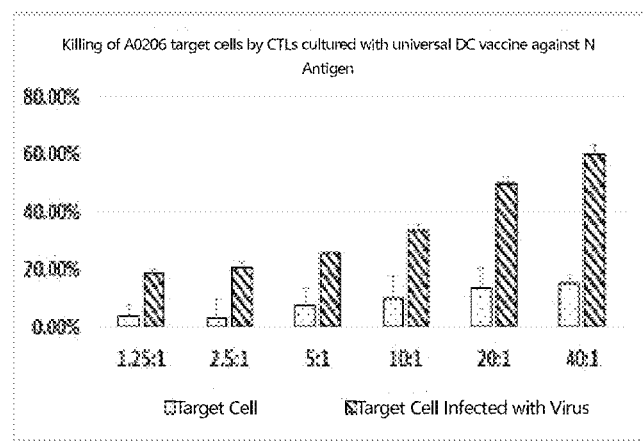
FIG. 100 shows the killing effect of CTLs cultured with the universal DC vaccine of Example 18 on HLA-A0206 target cells in Example 19.
Figure 101:
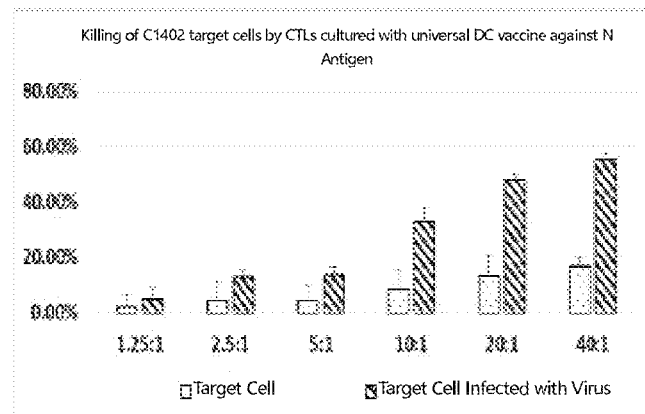
FIG. 101 shows the killing effect of CTLs cultured with the universal DC vaccine of Example 18 on HLA-C1402 target cells in Example 19.
Figure 102:
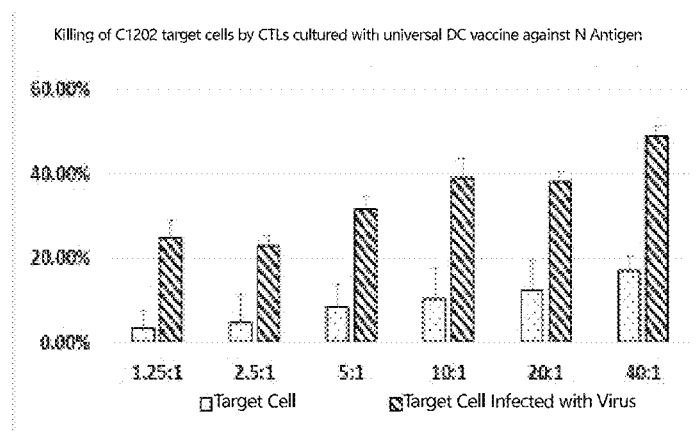
FIG. 102 shows the killing effect of CTLs cultured with the universal DC vaccine of Example 18 on HLA-C1202 target cells in Example 19.
Figure 103:
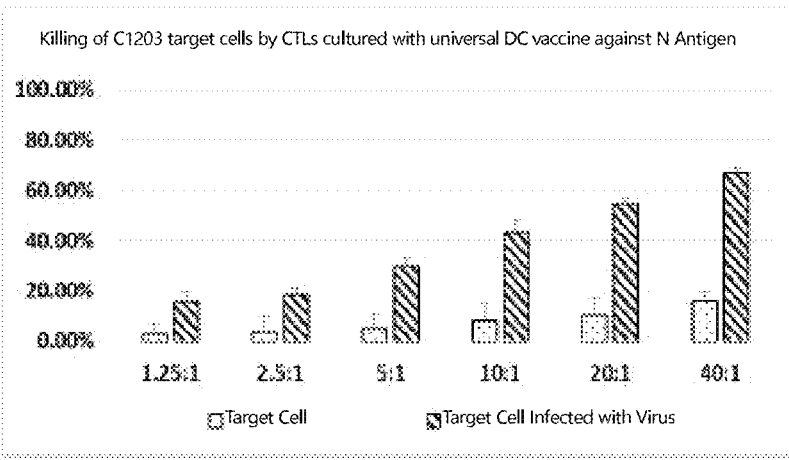
FIG. 103 shows the killing effect of CTLs cultured with the universal DC vaccine of Example 18 on HLA-C1203 target cells in Example 19.
Figure 104:
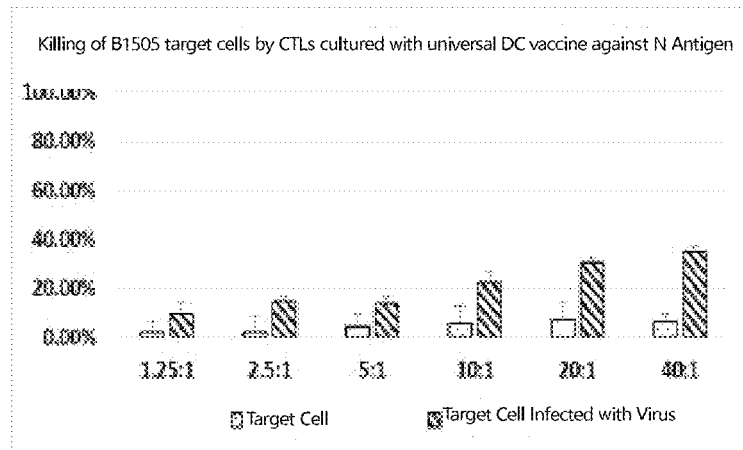
FIG. 104 shows the killing effect of CTLs cultured with the universal DC vaccine of Example 18 on HLA-B1505 target cells in Example 19.

The killing effect of the CTLs cultured with the universal DC vaccine of Example 18 on the HLA-A2601 target cells was shown in FIG. 99; the killing effect of the CTLs cultured with the universal DC vaccine of Example 18 on the HLA-A0206 target cells was shown in FIG. 100; the killing effect of the CTLs cultured with the universal DC vaccine of Example 18 on the HLA-C1402 target cells was shown in FIG. 101; the killing effect of the CTLs cultured with the universal DC vaccine of Example 18 on the HLA-C1202 target cells was shown in FIG. 102; the killing effect of the CTLs cultured with the universal DC vaccine of Example 18 on the HLA-C1203 target cells was shown in FIG. 103; and the killing effect of the CTLs cultured with the universal DC vaccine of Example 18 on the HLA-B1505 target cells was shown in FIG. 104.

Example 20

Figure 105:
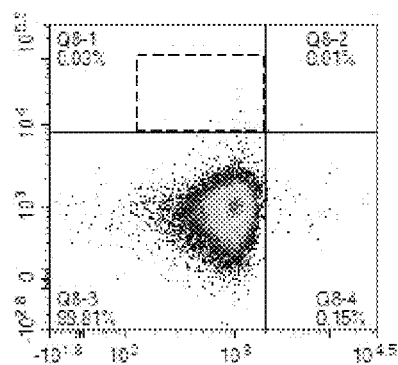
FIG. 105 shows the ratio of activated ones in cells cultured without stimulation by universal DC cells in Example 20.
Figure 106:
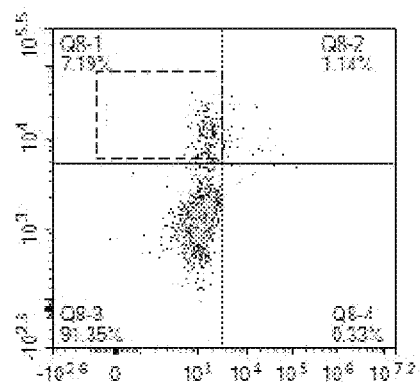
FIG. 106 shows CTLs cultured with stimulation by the universal DC cell vaccine against the HLA-A2601 targeted coronavirus N protein in Example 20.
Figure 107:
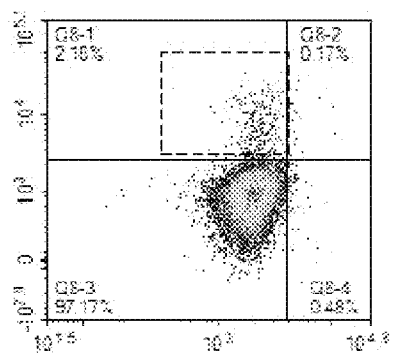
FIG. 107 shows CTLs cultured with stimulation by the universal DC cell vaccine against the HLA-A0206 targeted coronavirus N protein in Example 20.
Figure 108:
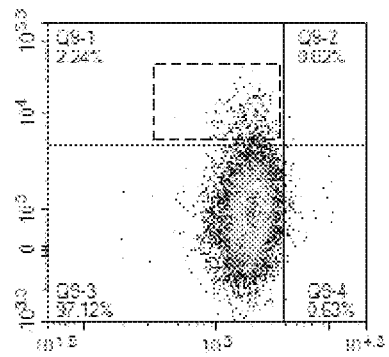
FIG. 108 shows CTLs cultured with stimulation by the universal DC cell vaccine against the HLA-C1402 targeted coronavirus N protein in Example 20.
Figure 109:
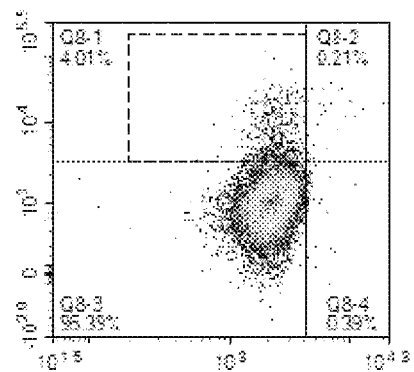
FIG. 109 shows CTLs cultured with stimulation by the universal DC cell vaccine against the HLA-C1202 targeted coronavirus N protein in Example 20.
Figure 110:
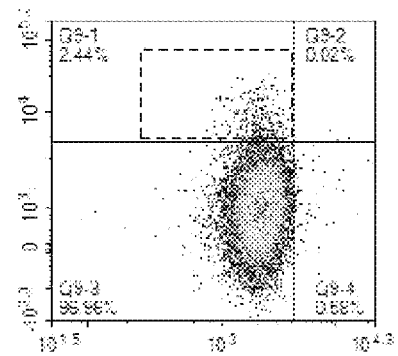
FIG. 110 shows CTLs cultured with stimulation by the universal DC cell vaccine against the HLA-C1203 targeted coronavirus N protein in Example 20.
Figure 111:
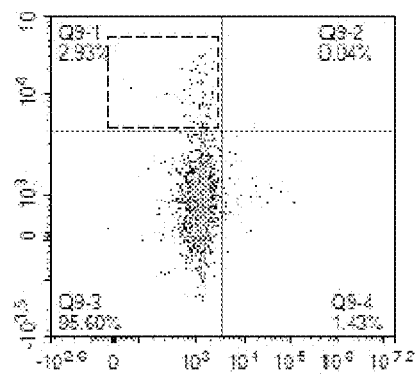
FIG. 111 shows CTLs cultured with stimulation by the universal DC cell vaccine against the HLA-B1505 targeted coronavirus N protein in Example 20.
Figure 112:
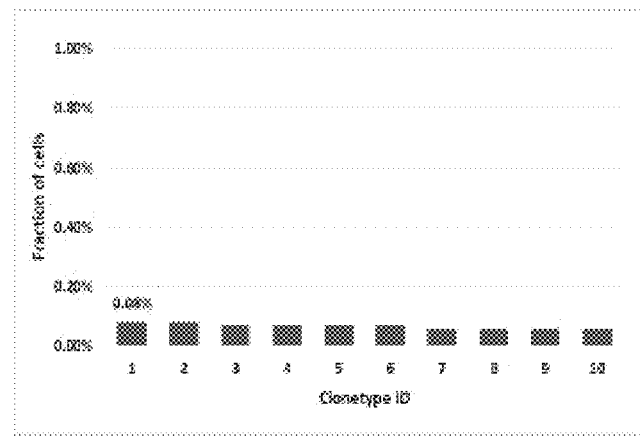
FIG. 112 shows the analysis result of TCR distribution frequency of cells cultured without stimulation by universal DC cells in Example 20.
Figure 113:
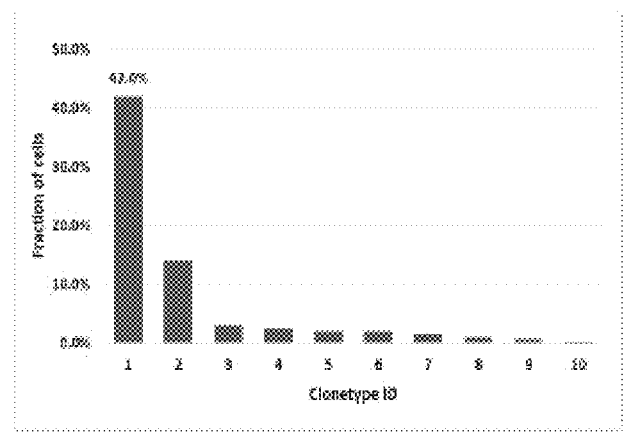
FIG. 113 shows the analysis result of TCR distribution frequency of CTL cells cultured with stimulation by the universal DC cell vaccine against the HLA-A2601 targeted coronavirus N protein in Example 20.
Figure 114:
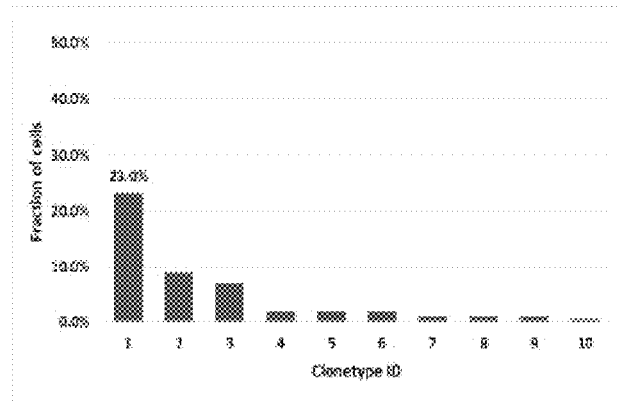
FIG. 114 shows the analysis result of TCR distribution frequency of CTL cells cultured with stimulation by the universal DC cell vaccine against the HLA-A0206 targeted coronavirus N protein in Example 20.
Figure 115:
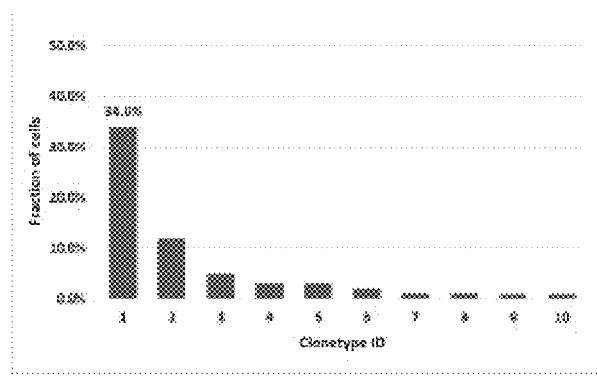
FIG. 115 shows the analysis result of TCR distribution frequency of CTL cells cultured with stimulation by the universal DC cell vaccine against the HLA-C1402 targeted coronavirus N protein in Example 20.
Figure 116:
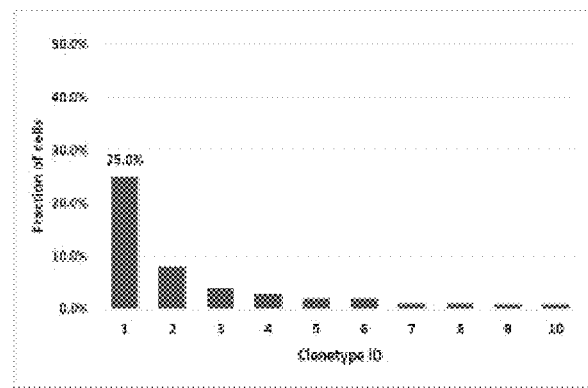
FIG. 116 shows the analysis result of TCR distribution frequency of CTL cells cultured with stimulation by the universal DC cell vaccine against the HLA-C1202 targeted coronavirus N protein in Example 20.
Figure 117:
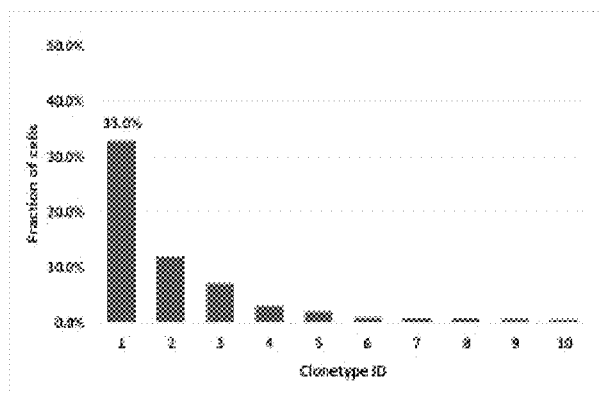
FIG. 117 shows the analysis result of TCR distribution frequency of CTL cells cultured with stimulation by the universal DC cell vaccine against the HLA-C1203 targeted coronavirus N protein in Example 20.
Figure 118:
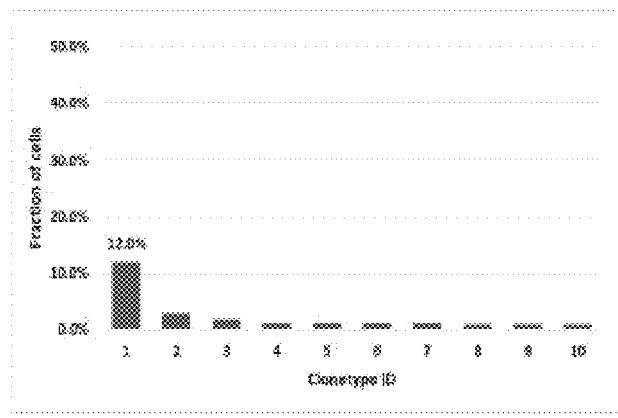
FIG. 118 shows the analysis result of TCR distribution frequency of CTL cells cultured with stimulation by the universal DC cell vaccine against the HLA-B1505 targeted coronavirus N protein in Example 20.

The CTLs were cultured with stimulation by the universal DC cell vaccine targeting the coronavirus N protein as constructed in Example 18, then added with the universal DC cells for secondary stimulation, and detected for the expression of CD137. The results were shown in FIGS. 105-111, wherein FIG. 105 showed the ratio of activated ones in cells cultured without stimulation by the universal DC cells, FIG. 106 showed the ratio of activated cells in the CTLs cultured with stimulation by the universal DC cell vaccine targeting the A2601 coronavirus N protein, FIG. 107 showed the ratio of activated cells in the CTLs cultured with stimulation by the universal DC cells against A0206 of Example 18, FIG. 108 showed the ratio of activated cells in the CTLs cultured with stimulation by the universal DC cells against C1402 of Example 18, FIG. 109 showed the ratio of activated cells in the CTLs cultured with stimulation by the universal DC cells against C1202 of Example 18, FIG. 110 showed the ratio of activated cells in the CTLs cultured with stimulation by the universal DC cells against C1203 of Example 18, and FIG. 111 showed the ratio of activated cells in the CTLs cultured with stimulation by the universal DC cells against B1505 of Example 18. The results showed that: among the CTLs cultured with stimulation by the universal DC cell vaccine targeting the coronavirus N protein, 7.19%, 2.18%, 2.24%, 4.01%, 2.44%, and 2.93% of the cells were in the activated state (in the dotted box). Sequencing analysis of 10× transcriptomes and VDJ was conducted on the CTLs, and the results were shown in FIGS. 112-118, wherein FIG. 112 showed the analysis result of TCR distribution frequency of cells cultured without stimulation by the universal DC cells, FIG. 113 showed the analysis result of TCR distribution frequency of CTL cells cultured with stimulation by the universal DC cell vaccine targeting the A2601 coronavirus N protein, FIG. 114 showed the analysis result of TCR distribution frequency of CTL cells cultured with stimulation by the universal DC cell against A0206 of Example 18, FIG. 115 showed the analysis result of TCR distribution frequency of CTL cells cultured with stimulation by the universal DC cell against C1402 of Example 18, FIG. 116 showed the analysis result of TCR distribution frequency of CTL cells cultured with stimulation by the universal DC cell against C1202 of Example 18, FIG. 117 showed the analysis result of TCR distribution frequency of CTL cells cultured with stimulation by the universal DC cell against C1203 of Example 18, and FIG. 118 showed the analysis result of TCR distribution frequency of CTL cells cultured with stimulation by the universal DC cell against B1505 of Example 18. The results showed that: in the TCR distribution of CD137+ T cells among the CTL cells cultured with stimulation by the universal DC cell vaccine targeting the coronavirus N protein, there were 42%, 23%, 34%, 25%, 33%, and 12% of high-frequency clones, compared with the cells cultured without stimulation by the universal DC cell vaccine having the highest TCR frequency of only 0.08%. Therefore, it could be proved that the universal DC vaccine could effectively stimulate specific T cells.

The above description is only preferred embodiments of the present invention. It should be pointed out that, for those of ordinary skills in the art, several improvements and modifications can be made without departing from the principle of the present invention. These improvements and modifications should also be considered as falling into the claimed scope of the present invention.

What is claimed is:

1. A method for preparing a coronavirus-targeting universal DC cell vaccine, comprising the following steps:

(1) ligating a fusion gene onto an expression vector to obtain a recombinant vector, wherein the fusion gene comprises a first fusion gene or a second fusion gene, the first fusion gene comprises an HLA gene and a gene of coronavirus open reading frame protein connected by a linker sequence, and the second fusion gene comprises an HLA gene and a gene of coronavirus structural protein connected by a linker sequence;

(2) transferring the recombinant vector of step (1) into antigen-presenting cells to be transfected, and using antibiotics to screen antigen-presenting cells into which the recombinant vector has been transferred[[ ]], so as to obtain the coronavirus-targeting universal DC cell vaccine;

wherein in step (1), the gene of coronavirus open reading frame protein is selected from one of ORF3a, ORF6, ORF7a and ORF8; the nucleotide sequence of ORF3a is SEQ ID NO: 1; the nucleotide sequence of ORF6 is SEQ ID NO: 2; the nucleotide sequence of ORF7a is SEQ ID NO: 3; and the nucleotide sequence of ORF8 is SEQ ID NO: 4;

wherein the gene of the coronavirus structural protein in step (1) is selected from one of a coronavirus E protein gene, a coronavirus S protein gene, a coronavirus PLP protein gene, a coronavirus M protein gene and a coronavirus N protein gene; the nucleotide sequence of coronavirus E protein gene is SEQ ID NO: 5; the nucleotide sequence of coronavirus S protein gene is SEQ ID NO: 6; the nucleotide sequence of coronavirus PLP protein gene is SEQ ID NO: 7; the nucleotide sequence of coronavirus M protein gene is SEQ ID NO: 8; and the nucleotide sequence of coronavirus N protein gene is SEQ ID NO: 9; and wherein the method for preparing the antigen-presenting cells to be transfected in step (2) comprises the following steps:

(a) ligating a fusion gene of TAX and ST40 connected by a linker sequence onto an expression vector to obtain a recombinant vector, wherein the nucleotide sequence of TAX is SEQ ID NO: 11, and the nucleotide sequence of ST40 is SEQ ID NO: 12;

(b) packaging a lentivirus with the recombinant vector of step (a) to obtain a packaged virus;
(c) infecting DC cells with the packaged virus of step (b) to obtain infected DC cells;
(d) inoculating trophoblast cells in an upper culture chamber of a cell incubator, inoculating the infected DC cells obtained in step (c) in a lower culture chamber of the cell incubator, conducting first culture for 4-6 weeks, conducting second culture for 1-2 weeks after removing CD3+ cells, then conducting third culture for more than 2 months after removing CD3+ cells to obtain the antigen-presenting cells to be transfected.

2. The preparation method according to claim 1, wherein the nucleotide sequence of the fusion gene of TAX and ST40 connected by the linker sequence in step (a) is SEQ ID NO: 13.

3. The preparation method according to claim 1, wherein the trophoblast cells in step (d) are prepared by the following method: culturing peripheral blood mononuclear cells in a RPMI 1640 medium containing fetal bovine serum for 9-14 h to obtain the trophoblast cells;
and the percentage mass content of the fetal bovine serum in the 1640 medium is 8%-12%.

4. The preparation method according to claim 2, wherein the inoculation amount of the trophoblast cells in step (d) is $0.5 \times 10^6$-$1.5 \times 10^6$ cells/well; and the inoculation amount of the infected DC cells is $0.5 \times 10^6$-$1.5 \times 10^6$ cells/well.

5. The preparation method according to claim 3, wherein the inoculation amount of the trophoblast cells in step (d) is $0.5 \times 10^6$-$1.5 \times 10^6$ cells/well; and the inoculation amount of the infected DC cells is $0.5 \times 10^6$-$1.5 \times 10^6$ cells/well.

* * * * *

SEQUENCE LISTING

```
<160> NUMBER OF SEQ ID NOS: 14

<210> SEQ ID NO 1
<211> LENGTH: 825
<212> TYPE: DNA
<213> ORGANISM: artificial sequence
<220> FEATURE:
<223> OTHER INFORMATION: the nucleotide sequence of the ORF3a

<400> SEQUENCE: 1
atggatttgt ttatgagaat cttcacaatt ggaactgtaa ctttgaagca aggtgaaatc      60
aaggatgcta ctccttcaga tttttgttcgc gctactgcaa cgataccgat acaagcctca     120 ctcccttcg gatggcttat tgttggcgtt gcacttcttg ctgtttttca gagcgcttcc      180
```

| | |
|---|---|
| aaaatcataa ccctcaaaaa gagatggcaa ctagcactct ccaagggtgt tcactttgtt | 240 |
| tgcaacttgc tgttgttgtt tgtaacagtt tactcacacc ttttgctcgt tgctgctggc | 300 |
| cttgaagccc cttttctcta tctttatgct ttagtctact tcttgcagag tataaacttt | 360 |
| gtaagaataa taatgaggct ttggctttgc tggaaatgcc gttccaaaaa cccattactt | 420 |
| tatgatgcca actattttct tgctggcat actaattgtt acgactattg tataccttac | 480 |
| aatagtgtaa cttcttcaat tgtcattact tcaggtgatg cacaacaag tcctatttct | 540 |
| gaacatgact accagattgg tggttatact gaaaaatggg aatctggagt aaaagactgt | 600 |
| gttgtattac acagttactt cacttcagac tattaccagc tgtactcaac tcaattgagt | 660 |
| acagacactg gtgttgaaca tgttaccttc ttcatctaca ataaaattgt tgatgagcct | 720 |
| gaagaacatg tccaaattca cacaatcgac ggttcatccg gagttgttaa tccagtaatg | 780 |
| gaaccaattt atgatgaacc gacgacgact actagcgtgc ctttg | 825 |

```
<210> SEQ ID NO 2
<211> LENGTH: 183
<212> TYPE: DNA
<213> ORGANISM: artificial sequence
<220> FEATURE:
<223> OTHER INFORMATION: the nucleotide sequence of the ORF6

<400> SEQUENCE: 2
```

| | |
|---|---|
| atgtttcatc tcgttgactt tcaggttact atagcagaga tattactaat tattatgagg | 60 |
| acttttaaag tttccatttg gaatcttgat tacatcataa acctcataat taaaaattta | 120 |
| tctaagtcac taactgagaa taaatattct caattagatg aagagcaacc aatggagatt | 180 |
| gat | 183 |

```
<210> SEQ ID NO 3
<211> LENGTH: 363
<212> TYPE: DNA
<213> ORGANISM: artificial sequence
<220> FEATURE:
<223> OTHER INFORMATION: the nucleotide sequence of the ORF7a

<400> SEQUENCE: 3
```

| | |
|---|---|
| atgaaaatta ttctttctctt ggcactgata acactcgcta cttgtgagct ttatcactac | 60 |
| caagagtgtg ttagaggtac aacagtactt ttaaaagaac cttgctcttc tggaacatac | 120 |
| gagggcaatt caccatttca tcctctagct gataacaaat ttgcactgac ttgctttagc | 180 |
| actcaatttg cttttgcttg tcctgacggc gtaaaacacg tctatcagtt acgtgccaga | 240 |
| tcagtttcac ctaaactgtt catcagacaa gaggaagttc aagaacttta ctctccaatt | 300 |
| tttcttattg ttgcggcaat agtgtttata acactttgct tcacactcaa agaaagaca | 360 |
| gaa | 363 |

```
<210> SEQ ID NO 4
<211> LENGTH: 363
<212> TYPE: DNA
<213> ORGANISM: artificial sequence
<220> FEATURE:
<223> OTHER INFORMATION: the nucleotide sequence of the ORF8

<400> SEQUENCE: 4
```

| | |
|---|---|
| atgaaatttc ttgttttctt aggaatcatc acaactgtag ctgcatttca ccaagaatgt | 60 |
| agtttacagt catgtactca acatcaacca tatgtagttg atgacccgtg tcctattcac | 120 |
| ttctattcta aatggtatat tagagtagga gctagaaaat cagcaccttt aattgaattg | 180 |

```
tgcgtggatg aggctggttc taaatcaccc attcagtaca tcgatatcgg taattataca    240
gtttcctgtt tacctttttac aattaattgc caggaaccta aattgggtag tcttgtagtg   300
cgttgttcgt tctatgaaga ctttttagag tatcatgacg ttcgtgttgt tttagatttc    360
atc                                                                  363

<210> SEQ ID NO 5
<211> LENGTH: 225
<212> TYPE: DNA
<213> ORGANISM: artificial sequence
<220> FEATURE:
<223> OTHER INFORMATION: the nucleotide sequence of the coronavirus E
      protein gene

<400> SEQUENCE: 5
atgtactcat tcgtttcgga agagacaggt acgttaatag ttaatagcgt acttcttttt    60
cttgctttcg tggtattctt gctagttaca ctagccatcc ttactgcgct tcgattgtgt   120
gcgtactgct gcaatattgt taacgtgagt cttgtaaaac cttctttta cgtttactct   180 cgtgttaaaa atctgaattc ttctagagtt cctgatcttc tggtc                   225

<210> SEQ ID NO 6
<211> LENGTH: 666
<212> TYPE: DNA
<213> ORGANISM: artificial sequence
<220> FEATURE:
<223> OTHER INFORMATION: the nucleotide sequence of the coronavirus S
      protein gene

<400> SEQUENCE: 6
atggcagatt ccaacggtac tattaccgtt gaagagctta aaaagctcct tgaacaatgg    60
aacctagtaa taggtttcct attccttaca tggatttgtc ttctacaatt tgcctatgcc   120
aacaggaata ggttttttgta tataattaag ttaattttcc tctggctgtt atggccagta  180
actttagctt gttttgtgct tgctgctgtt tacagaataa attggatcac cggtggaatt   240
gctatcgcaa tggcttgtct tgtaggcttg atgtggctca gctacttcat tgcttctttc   300
agactgtttg cgcgtacgcg ttccatgtgg tcattcaatc cagaaactaa cattcttctc   360
aacgtgccac tccatggcac tattctgacc agaccgcttc tagaaagtga actcgtaatc   420
ggagctgtga tccttcgtgg acatcttcgt attgctggac accatctagg acgctgtgac   480
atcaaggacc tgcctaaaga aatcactgtt gctacatcac gaacgctttc ttattacaaa   540
ttgggagctt cgcagcgtgt agcaggtgac tcaggttttg ctgcatacag tcgctacagg   600
attggcaact ataaattaaa cacagaccat tccagtagca gtgacaatat tgctttgctt   660
gtacag                                                               666

<210> SEQ ID NO 7
<211> LENGTH: 957
<212> TYPE: DNA
<213> ORGANISM: artificial sequence
<220> FEATURE:
<223> OTHER INFORMATION: the nucleotide sequence of the coronavirus PLP
      protein gene

<400> SEQUENCE: 7
atggaggtgc ggaccatcaa ggtgttcacc acagtggaca acatcaatct gcacacacag    60
gtggtggata tgtccatgac ctacggccag cagtttggcc ctacatatct ggacggcgcc   120
gatgtgacca agatcaagcc acacaactct cacgagggca agacattcta cgtgctgccc   180
```

| | | | |
|---|---|---|---|
| aatgacgata | ccctgagggt ggaggccttc gagtactatc acaccacaga | cccatccttt | 240 |
| ctgggccgct | acatgtctgc cctgaaccac acaaagaagt ggaagtatcc | ccaagtgaat | 300 |
| ggcctgacct | ctatcaagtg ggccgacaac aattgctacc tggccacagc | cctgctgacc | 360 |
| ctgcagcaga | tcgagctgaa gttcaacccc cctgccctgc aggatgcata | ctatagggca | 420 |
| agagcaggag | aggcagcaaa cttttgcgca ctgatcctgg cctactgtaa | taagacagtg | 480 |
| ggagagctgg | gcgacgtgcg ggagaccatg agctatctgt ccagcacgc | caacctggat | 540 |
| tcctgtaaga | gggtgctgaa tgtggtgtgc aagacatgtg ccagcagca | gaccacactg | 600 |
| aagggcgtgg | aggccgtgat gtacatgggc accctgagct atgagcagtt | taagaagggc | 660 |
| gtgcagatcc | cttgcacatg tggcaagcag gccaccaagt acctggtgca | gcaggagtct | 720 |
| ccattcgtga | tgatgagcgc cccacccgcc cagtatgagc tgaagcacgg | caccttcacc | 780 |
| tgcgcctctg | agtacaccgg caactatcag tgtggccact acaagcacat | cacaagcaag | 840 |
| gagaccctgt | attgcatcga cggcgccctg ctgacaaaga gctccgagta | caagggcccc | 900 |
| atcaccgacg | tgttctacaa ggagaacagc tataccacaa ccatcaagcc | tgtgacc | 957 |

<210> SEQ ID NO 8
<211> LENGTH: 666
<212> TYPE: DNA
<213> ORGANISM: artificial sequence
<220> FEATURE:
<223> OTHER INFORMATION: the nucleotide sequence of the coronavirus M
      protein gene

<400> SEQUENCE: 8

| | | | |
|---|---|---|---|
| atggcagatt | ccaacggtac tattaccgtt gaagagctta aaaagctcct | tgaacaatgg | 60 |
| aacctagtaa | taggtttcct attccttaca tggatttgtc ttctacaatt | tgcctatgcc | 120 |
| aacaggaata | ggttttttgta tataattaag ttaatttttcc tctggctgtt | atggccagta | 180 |
| actttagctt | gttttgtgct tgctgctgtt tacagaataa attggatcac | cggtggaatt | 240 |
| gctatcgcaa | tggcttgtct tgtaggcttg atgtggctca gctacttcat | tgcttctttc | 300 |
| agactgtttg | cgcgtacgcg ttccatgtgg tcattcaatc cagaaactaa | cattcttctc | 360 |
| aacgtgccac | tccatggcac tattctgacc agaccgcttc tagaaagtga | actcgtaatc | 420 |
| ggagctgtga | tccttcgtgg acatcttcgt attgctggac accatctagg | acgctgtgac | 480 |
| atcaaggacc | tgcctaaaga aatcactgtt gctacatcac gaacgctttc | ttattacaaa | 540 |
| ttgggagctt | cgcagcgtgt agcaggtgac tcaggttttg ctgcatacag | tcgctacagg | 600 |
| attggcaact | ataaattaaa cacagaccat tccagtagca gtgacaatat | tgctttgctt | 660 |
| gtacag | | | 666 |

<210> SEQ ID NO 9
<211> LENGTH: 1257
<212> TYPE: DNA
<213> ORGANISM: artificial sequence
<220> FEATURE:
<223> OTHER INFORMATION: the nucleotide sequence of the coronavirus N
      protein gene

<400> SEQUENCE: 9

| | | | |
|---|---|---|---|
| atgtctgata | tggacccca aaatcagcga atgcacccc gcattacgtt | tggtggaccc | 60 |
| tcagattcaa | ctggcagtaa ccagaatgga gaacgcagtg gggcgcgatc | aaaacaacgt | 120 |
| cggccccaag | gtttacccaa taatactgcg tcttggttca ccgctctcac | tcaacatggc | 180 |

| aaggaagacc | ttaaattccc | tcgaggacaa | ggcgttccaa | ttaacaccaa | tagcagtcca | 240 |
| gatgaccaaa | ttggctacta | ccgaagagct | accagacgaa | ttcgtggtgg | tgacggtaaa | 300 |
| atgaaagatc | tcagtccaag | atggtatttc | tactacctag | gaactgggcc | agaagctgga | 360 |
| cttccctatg | gtgctaacaa | agacggcatc | atatgggttg | caactgaggg | agccttgaat | 420 |
| acaccaaaag | atcacattgg | cacccgcaat | cctgctaaca | atgctgcaat | cgtgctacaa | 480 |
| cttcctcaag | gaacaacatt | gccaaaaggc | ttctacgcag | aagggagcag | aggcggcagt | 540 |
| caagcctctt | ctcgttcctc | atcacgtagt | cgcaacagtt | caagaaattc | aactccaggc | 600 |
| agcagtaggg | gaacttctcc | tgctagaatg | gctggcaatg | gcggtgatgc | tgctcttgct | 660 |
| ttgctgctgc | ttgacagatt | gaaccagctt | gagagcaaaa | tgtctggtaa | aggccaacaa | 720 |
| caacaaggcc | aaactgtcac | taagaaatct | gctgctgagg | cttctaagaa | gcctcggcaa | 780 |
| aaacgtactg | ccactaaagc | atacaatgta | acacaagctt | tcggcagacg | tggtccagaa | 840 |
| caaacccaag | gaaattttgg | ggaccaggaa | ctaatcagac | aaggaactga | ttacaaacat | 900 |
| tggccgcaaa | ttgcacaatt | tgcccccagc | gcttcagcgt | tcttcggaat | gtcgcgcatt | 960 |
| ggcatggaag | tcacaccttc | gggaacgtgg | ttgacctaca | caggtgccat | caaattggat | 1020 |
| gacaaagatc | caaatttcaa | agatcaagtc | attttgctga | ataagcatat | tgacgcatac | 1080 |
| aaaacattcc | caccaacaga | gcctaaaaag | gacaaaaaga | agaaggctga | tgaaactcaa | 1140 |
| gccttaccgc | agagacagaa | gaaacagcaa | actgtgactc | ttcttcctgc | tgcagatttg | 1200 |
| gatgatttct | ccaaacaatt | gcaacaatcc | atgagcagtg | ctgactcaac | tcaggcc | 1257 |

<210> SEQ ID NO 10
<211> LENGTH: 57
<212> TYPE: DNA
<213> ORGANISM: artificial sequence
<220> FEATURE:
<223> OTHER INFORMATION: the nucleotide sequence of the linker sequence

<400> SEQUENCE: 10

| gccacgaact | tctctctgtt | aaagcaagca | ggagatgttg | aagaaaaccc | cgggcct | 57 |

<210> SEQ ID NO 11
<211> LENGTH: 273
<212> TYPE: DNA
<213> ORGANISM: artificial sequence
<220> FEATURE:
<223> OTHER INFORMATION: the nucleotide sequence of the TAX

<400> SEQUENCE: 11

| atgaacatca | agacgaatg | gtactggggt | aagagtaagc | acgcggtgac | tgagctcaac | 60 |
| gcggagggat | ggatctttac | tctcccgcca | agtgacaact | acatcggacg | tcaccggttg | 120 |
| ccggacgtcc | gattcagcca | ggagctaccc | gacgggacgg | tctactggtc | ggtgaaccgg | 180 |
| aagaacttct | tccgccggga | cgacagcctc | ccctcgggat | gggtgcagcg | catctacccg | 240 |
| cgtgtagcta | ccagcttcag | gaccgcggaa | tga | | | 273 |

<210> SEQ ID NO 12
<211> LENGTH: 666
<212> TYPE: DNA
<213> ORGANISM: artificial sequence
<220> FEATURE:
<223> OTHER INFORMATION: the nucleotide sequence of the ST40

<400> SEQUENCE: 12

| gcccatttcc | caggatttgg | acagagcctc | ctatatggat | accccgtcta | cgtgtttggc | 60 |

```
gattgtgtac aggccgattg gtgtcccgtc tcaggtggtc tatgttccac ccgcctacat    120
cgacatgccc tcctggccac ctgtccagag caccaactca cctgggaccc catcgatgga    180
cgcgttgtca gctctcctct ccaatacctt atccctcgcc tcccctcctt ccccacccag    240
agaacctcaa ggaccctcaa ggtccttacc cctcccacca ctcctgtctc ccccaaggtt    300
ccacctgcct tctttcaatc aatgcgaaag cacacccccct accgaaatgg atgcctggaa    360
ccaaccctcg gggatcagct cccctccctc gccttccccg aacctggcct ccgtccccaa    420
aacatctaca ccacctgggg aaaaaccgta gtatgcctat acctatacca gctttcccca    480
cccatgacat ggccacttat accccatgtc atattctgcc accccagaca attaggagcc    540
ttcctcacca aggtgcctct aaaacgatta gaagaacttc tatacaaaat gttcctacac    600
acagggacag tcatagtcct cccggaggac gacctaccca ccacaatgtt ccaacccgtg    660
agggct                                                               666
```

<210> SEQ ID NO 13
<211> LENGTH: 996
<212> TYPE: DNA
<213> ORGANISM: artificial sequence
<220> FEATURE:
<223> OTHER INFORMATION: the nucleotide sequence of the fusion gene of
      TAX and ST40

<400> SEQUENCE: 13

```
atgaacatca agacgaatg gtactggggt aagagtaagc acgcggtgac tgagctcaac    60
gcggagggat ggatctttac tctcccgcca agtgacaact acatcggacg tcaccggttg    120
ccggacgtcc gattcagcca ggagctaccc gacgggacgg tctactggtc ggtgaaccgg    180
aagaacttct tccgccggga cgacagcctc ccctcgggat gggtgcagcg catctacccg    240
cgtgtagcta ccagcttcag gaccgcggaa tgagccacga acttctctct gttaaagcaa    300
gcaggagatg ttgaagaaaa ccccgggcct gcccatttcc caggatttgg acagagcctc    360
ctatatggat acccccgtcta cgtgtttggc gattgtgtac aggccgattg gtgtcccgtc    420
tcaggtggtc tatgttccac ccgcctacat cgacatgccc tcctggccac ctgtccagag    480
caccaactca cctgggaccc catcgatgga cgcgttgtca gctctcctct ccaatacctt    540
atccctcgcc tcccctcctt ccccacccag agaacctcaa ggaccctcaa ggtccttacc    600
cctcccacca ctcctgtctc ccccaaggtt ccacctgcct tctttcaatc aatgcgaaag    660
cacaccccct accgaaatgg atgcctggaa ccaaccctcg gggatcagct cccctccctc    720
gccttccccg aacctggcct ccgtccccaa aacatctaca ccacctgggg aaaaaccgta    780
gtatgcctat acctatacca gctttcccca cccatgacat ggccacttat accccatgtc    840
atattctgcc accccagaca attaggagcc ttcctcacca aggtgcctct aaaacgatta    900
gaagaacttc tatacaaaat gttcctacac acagggacag tcatagtcct cccggaggac    960
gacctaccca ccacaatgtt ccaacccgtg agggct                              996
```

<210> SEQ ID NO 14
<211> LENGTH: 1566
<212> TYPE: DNA
<213> ORGANISM: artificial sequence
<220> FEATURE:
<223> OTHER INFORMATION: the nucleotide sequence of the HLA-A0201

<400> SEQUENCE: 14

```
gctagcgcca ccatggccac catggccgtc atggcgcccc gaaccctcgt cctgctactc    60
```

-continued

```
tcggggctc tggccctgac ccagacctgg gcgggctctc actccatgag gtatttcttc    120
acatccgtgt cccggcccgg ccgcggggag ccccgcttca tcgcagtggg ctacgtggac    180
gacacgcagt tcgtgcggtt cgacagcgac gccgcgagcc agaggatgga gccgcgggcg    240
ccgtggatag agcaggaggg tccggagtat tgggacgggg agacacggaa agtgaaggcc    300
cactcacaga ctcaccgagt ggacctgggg accctgcgcg gctactacaa ccagagcgag    360
gccggttctc acaccgtcca gaggatgtat ggctgcgacg tggggtcgga ctggcgcttc    420
ctccgcgggt accaccagta cgcctacgac ggcaaggatt acatcgccct gaaagaggac    480
ctgcgctctt ggaccgcggc ggacatggca gctcagacca ccaagcacaa gtgggaggcg    540
gcccatgtgg cggagcagtt gagagcctac ctggagggca cgtgcgtgga gtggctccgc    600
agatacctgg agaacgggaa ggagacgctg cagcgcacgg acgccccaa aacgcatatg     660
actcaccacg ctgtctctga ccatgaagcc accctgaggt gctgggccct gagcttctac    720
cctgcggaga tcacactgac ctggcagcgg gatggggagg accagaccca ggacacggag    780
ctcgtggaga ccaggcctgc aggggatgga accttccaga agtgggcggc tgtggtggtg    840
ccttctggac aggagcagag atacacctgc catgtgcagc atgagggttt gcccaagccc    900
ctcaccctga gatgggagcc gtcttcccag cccaccatcc ccatcgtggg catcattgct    960
ggcctggttc tctttggagc tgtgatcact ggagctgtgg tcgctgctgt gatgtggagg   1020
aggaagagct cagatagaaa aggagggagc tactctcagg ctgcaagcag tgacagtgcc   1080
cagggctctg atgtgtctct cacagcttgt aaagtggatt acaaggatga cgacgataag   1140
gagggcagag gaagtcttct aacatgcggt gacgtggagg agaatcccgg ccctgccacc   1200
atgtctcgct ccgtggcctt agctgtgctc gcgctactct ctctttctgg cctgaggct    1260
atccagcgta ctccaaagat tcaggtttac tcacgtcatc cagcagagaa tggaaagtca   1320
aatttcctga attgctatgt gtctgggttt catccatccg acattgaagt tgacttactg   1380
aagaatggag agagaattga aaaagtggag cattcagact tgtctttcag caaggactgg   1440
tctttctatc tcttgtacta cactgaattc acccccactg aaaaagatga gtatgcctgc   1500
cgtgtgaacc atgtgacttt gtcacagccc aagatagtta agtgggatcg agacatgtaa   1560
ggatcc                                                              1566
```